US00RE43797E

(19) United States
(12) Reissued Patent
Oppenheimer et al.

(10) Patent Number: US RE43,797 E
(45) Date of Reissued Patent: *Nov. 6, 2012

(54) METHODS OF ADMINISTERING TETRAHYDROBIOPTERIN

(75) Inventors: Daniel I. Oppenheimer, Castro Valley, CA (US); Alejandro Dorenbaum, Mill Valley, CA (US); Augustus O. Okhamafe, Concord, CA (US)

(73) Assignee: Biomarin Pharmaceutical Inc., Novato, CA (US)

( * ) Notice: This patent is subject to a terminal disclaimer.

(21) Appl. No.: 13/299,499

(22) Filed: Nov. 18, 2011

Related U.S. Patent Documents

Reissue of:

(64) Patent No.: 7,947,681
Issued: May 24, 2011
Appl. No.: 12/577,509
Filed: Oct. 12, 2009

U.S. Applications:

(63) Continuation of application No. 12/329,838, filed on Dec. 8, 2008, now Pat. No. 7,612,073, which is a continuation of application No. PCT/US2008/060041, filed on Apr. 11, 2008.

(60) Provisional application No. 60/922,821, filed on Apr. 11, 2007, provisional application No. 61/019,753, filed on Jan. 8, 2008.

(51) Int. Cl.

| | |
|---|---|
| ***A01N 43/58*** | (2006.01) |
| ***A61K 31/50*** | (2006.01) |
| ***A01N 43/60*** | (2006.01) |
| ***A61K 31/495*** | (2006.01) |

(52) U.S. Cl. ..... 514/249

(58) Field of Classification Search ..... 514/249
See application file for complete search history.

(56) References Cited

U.S. PATENT DOCUMENTS

| | | | |
|---|---|---|---|
| 4,550,109 | A | 10/1985 | Folkers et al. |
| 4,778,794 | A | 10/1988 | Naruse et al. |
| 5,753,656 | A | 5/1998 | Sakai et al. |
| 6,288,067 | B1 | 9/2001 | Okamura et al. |
| 6,410,535 | B1 | 6/2002 | Kashiwagi et al. |
| 6,544,994 | B2 | 4/2003 | Rabelink et al. |
| 6,995,158 | B2 | 2/2006 | Rabelink et al. |
| 7,566,462 | B2 | 7/2009 | Jungles et al. |
| 7,566,714 | B2 | 7/2009 | Oppenheimer et al. |
| 7,727,987 | B2 | 6/2010 | Moser et al. |
| 2006/0035900 | A1 | 2/2006 | Moser et al. |
| 2006/0194808 | A1 | 8/2006 | Richardson et al. |
| 2006/0211701 | A1 | 9/2006 | Muntau-Heger et al. |
| 2008/0075666 | A1 | 3/2008 | Dudley et al. |
| 2008/0146577 | A1 | 6/2008 | Matalon et al. |
| 2008/0213239 | A1 | 9/2008 | Morris |

FOREIGN PATENT DOCUMENTS

| | | |
|---|---|---|
| EP | 1964566 | 12/2005 |
| EP | 1757293 | 2/2007 |
| WO | WO 2004/058268 | 7/2004 |
| WO | WO 2005/049000 | 6/2005 |

OTHER PUBLICATIONS

Belanger-Quintana, et al., Spanish BH4-responsive phenylalanine hydroxylase-deficient patients: Evolution of seven patients on long-term treatment with tetrahydrobiopterin, *Mol. Gen. Metab.,* 86:S61-S66 (2005).
Blau, et al., Optimizing the use of sapropterin (BH4) in the management of phenylketonuria, Mol. Gen. Metab., (2009), doi:10.1016/j.ymgme.2009.01.002.
Calbet, et al., Role of caloric content on gastric emptying in humans, J Physiol., 498.2: 553-559 (1997).
Fiege, et al., Plasma tetrahydrobiopterin and its pharmacokinetic following oral administration, *Mol. Gen. Metab.,* 81:45-51 (2004).
Fleisher et al., Drug, Meal and Formulation Interactions Influencing Drug Absorption After Oral Administration, Clin. Pharmacokinet., 37(3):233 (1999).
Gu et al., Predicting Effect of Food on Extent of Drug Absorption Based on Physicochemical Properties, Pharmaceutical Research, 24(6):1118 (2007).
Hennermann, et al., Long-term treatment with tetrahydrobiopterin increases phenylalanine tolerance in children with severe phenotype of phenylketonuria, *Mol. Gen. Metab.,* 86:S86-S90 (2005).
Kuvan™ [sapropterin dihydrochloride (BH4)] Tablets Product Information, pp. 1-17 (Dec. 2007).
Levy, et al., Efficacy of sapropterin dihydrochloride (tetrahydrobiopterin, 6R-BH4) for reduction of phenylalanine concentration in patients with phenylketonuria: a phase III randomised placebo-controlled study, *The Lancet,* 370:504-510 (2007).
Levy, et al., Recommendations for evaluation of responsiveness to tetrahydrobiopterin (BH4) in phenylketonuria and its use in treatment, *Mol. Gen. Metab.,* 92:287-291 (2007).
Musson et al., The bioavaillability of Kuvan™ (sapropterin dihydrochloride) from intact or dissolved tablets administered with or without food to healthy volunteers, Abstract 70, published on p. 259 of *Molecular Genetics and Metabolism,* vol. 93, pp. 221-268 (2008) (presented at The Society for Inherited Metabolic Disorders (SIMD) Annual Meeting, Mar. 2-5, 2008, Pacific Grove, California).
O'Brien and Haddard, US Pharmacist, 22:6: 62 (1997).
Ponzone, et al., Hyperphenylalaninemia and pterin metabolism in serum and erythrocytes, *Clinica Chim. Acta.,* 216:63-71 (1993).
Schaub et al., Archives of Disease in Childhood, vol. 53, pp. 674-683 (1978).
Schirck's Laboratories, Summary of Product Characteristics—Tetrahydrobiopterin 10 mg/50 mg Tablets, dated Jan. 7, 2004.
Schmidt, et al., Single dose oral tetrahydrobiopterin (BH4) leads to a prolonged increase in aortic BH4 levels in ApoE-KO mice, *Abstracts/Atherosclerosis,* 193:S1-S5 (2007).
Shintaku, et al., Long-Term Treatment and Diagnosis of Tetrahydrobiopterin-Responsive Hyperphenylalaninemia with a Mutant Phenylalanine Hydroxylase Gene, *Ped. Res.,* 55(3):425-430 (2004).

(Continued)

*Primary Examiner* — Yong Chong
(74) *Attorney, Agent, or Firm* — Marshall, Gerstein & Borun LLP

(57) ABSTRACT

The present invention is directed to treatment methods of administering tetrahydrobiopterin, including in oral dosage forms, in intravenous formulations, and with food. Also disclosed herein are biopterin assays for measuring the amount of biopterin and metabolites of biopterin in a sample.

28 Claims, 38 Drawing Sheets

OTHER PUBLICATIONS

Shintaku, et al., Plasma biopterin levels and tetrahydrobiopterin responsiveness, *Mol. Gen. Metab.,* 86:S104-S106 (2005).

Steinfeld, et al., A hypothesis on the biochemical mechanism of BH4-responsiveness in phenylalanine hydroxylase deficiency, *Amino Acids,* 25:63-68 (2003).

Trefz, et al., Efficacy of Sapropterin Dihydrochloride in Increasing Phenylalanine Tolerance in Children with Phenylketonuria: A Phase III, Randomized Double-Blind, Placebo-Controlled Study, J. Pediatr, (2008), doi:10.1016/j,peds.2008.11.040).

USPTO, final Office Action, U.S. Appl. No. 12/329,838, dated May 14, 2009, pp. 1-13.

USPTO, Office Action, U.S. Appl. No. 12/329,838, dated Feb. 25, 2009, pp. 1-12.

Zurfluh, et al., Pharmacokinetics of orally administered tetrahydrobiopterin in patients with phenylalanine hydroxylase deficiency, *J. Inherit. Metab. Dis.,* 29:725-731 (2006).

FIGURE 16 - Flow chart of biopterin measurement
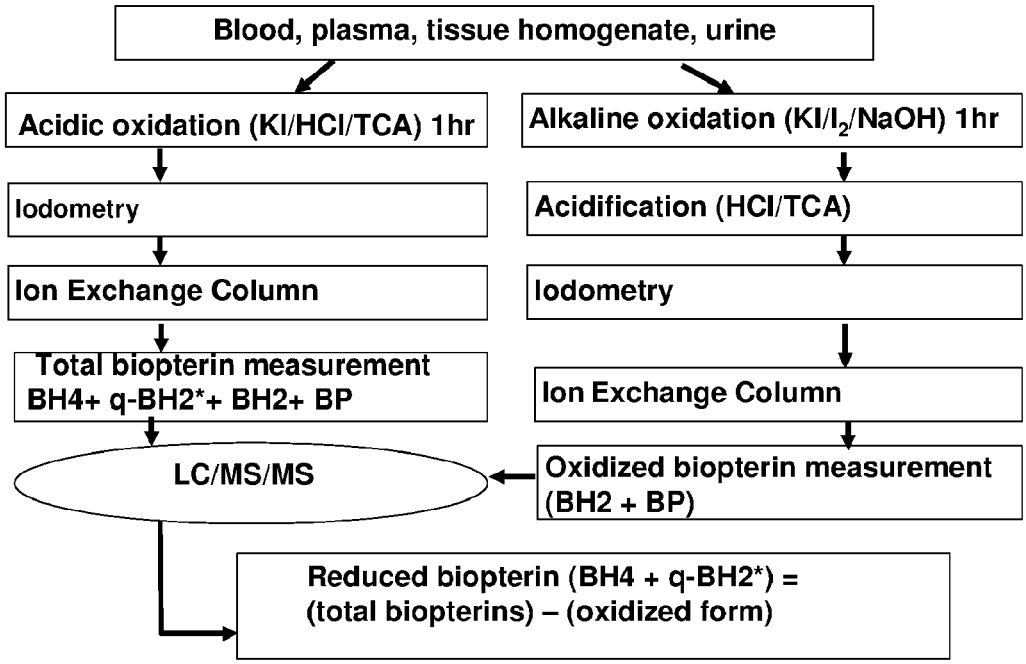
*q-BH2 is immediately reduced *in vivo* to BH4 so the measured reduced biopterin is based mainly upon BH4.

Figure 17

| Assay | LC/MS/MS Determination of BH4 in human plasma | HPLC Determination of biopterin in human plasma |
|---|---|---|
| **Analyte Name** | **Tetrahydrobiopterin (BH4)** | **Biopterin** |
| Analyte Name (oxidation product) | **L-biopterin** | Biopterin |
| Internal Standard | **Irbesartan** | Biopterin |
| **Analytical Method Type** | **LC/MS/MS** | **HPLC (Ex 365 nm/Em 473 nm)** |
| Extraction Method | Protein Precipitation | Protein Precipitation |
| QC Concentrations | 5, 15, 150, and 800 ng/mL BH4 | 1, 10, and 40 ng/mL biopterin |
| Standard Curve Concentrations | 5, 15, 50, 100, 300, 500, and 1000 ng/mL | 0.5, 1, 2.5, 5, 10, 25, and 50 ng/mL |
| **Lower Limit of Quantitation** | **5 ng/mL** | **(5 ng/mL biopterin)** |
| **Upper Limit of Quantitiation** | **1000 ng/mL** | **(50 ng/mL biopterin)** |
| Average Recovery of Drug | 65.3% | ?? |
| Average Recovery of Internal Standard | 94% | 74 -94% |
| QC Intraday Precision Range | 4.7 to 14.5 %CV | 0.8 to 13 |
| QC Intraday Accuracy Range | -7.1 to 7.4 %Diff | 2.8 to 6.1 |
| QC Interday Precision Range | 7.4 to 16.4 %CV | 0.6 to 4.9 |
| QC Interday Accuracy Range | -8.3 to 3.7 %Diff | ?? |
| Stock Solution Solvent | MeOH:DMSO/50:50 (v:v) | Ammonium phosphate buffer |
| Benchtop Stability in human Plasma | 4.5 hrs at RT | ?? |
| Freeze/thaw Stability in human plasma | 4 cycles at -70 C | 2 cycles at -20 C |
| **Conversion Ratio from BH4 to L-Biopterin** | **47% (at 12 weeks)** | **??** |
| Long-term stability in K2 EDTA plasma | 38 days at -70 C | ?? (7 days at -20 C) |
| Dilution Integrity | 1500 ng/mL diluted 10-times | ?? |
| **Selectivity** | **BH4** | **Total biopterin** |

Plasma Biopterin Concentration And Reduced-Form Ratio After Single-Dose Administration Of Sapropterin to Rats

Figure 19

Pharmacokinetic Parameters of Total Biopterins in Plasma after a Single Oral Administration of Sapropterin to Rats

| Dose (mg/kg) | Administration Route | Cendo[1] (ng/ml) | Cmax (ng/ml) | ΔCmax2[2] (ng/ml) | Tmax (hr) | ΔAUC[3] (ng·hr/ml) | $T_{1/2}$ (h) | F[4] (%) |
|---|---|---|---|---|---|---|---|---|
| 100 | p.o. | 38.2 | 1227 | 1189 | 1.0 | 4571 | 1.1(2-6 h) | 11.8 |
| 10 | p.o. | 33.5 | 108 | 75 | 2.0 | 265 | 1.1(2-6h) | 6.8 |
| 10 | i.v. | 33.5 | – | – | – | 3881 | 0.6(0.5–3h) | |
| 1 | i.v. | 33.5 | – | – | – | 529 | 0.3(0.5–3h) | |

[1] Endogenous total biopterin concentration

[2] Cmax – Cendo

[3] Computed based on trapezoidal rule, by using the value (ΔC) obtained by subtracting Cendo from the actually measured value (C) of plasma concentration.

[4] Bioavailability (F) was computed by using ΔAUC at the time of 10-mg/kg intravenous injection:

F = [ΔAUCpo] / [DOSEpo] / [ΔAUCiv] / 10 × 100 (%)

Sapropterin Lot #s:8886202, 8885Y05

(mean values of 2 to 5 animals)

Plasma Biopterin Concentration and Reduced-Form Ratio After a Single-Dose Administration of Sapropterin in Monkeys

FIGURE 21

Pharmacodynamic Parameters of Total Biopterins in Plasma after Single-Dose Administration of Sapropterin to Monkeys

| Dose (mg/kg) | Administration Route | Cendo[1] (ng/ml) | Cmax (ng/ml) | ΔCmax2[2] (ng/ml) | Tmax (hr) | ΔAUC[3] (ng·hr/ml) | $T_{1/2}$ (hr) | F[4] (%) |
|---|---|---|---|---|---|---|---|---|
| 10 | p.o. | 17.4±1.3 | 344±149 | 344±148.5 | 2.9±0.2 | 1301±144 | 1.42±0.17 | 9.0 |
| 1 | i.v. | 17.1±2.1 | | | | 1449±68.4 | 0.82±0.14 | |

[1] Endogenous total biopterin concentration

[2] Cmax – Cendo

[3] Computed based on trapezoid rule, by using the value (ΔC) obtained by subtracting Cendo from the actually measured value (C) of plasma concentration.

[4] Bioavailability (F) was computed by using ΔAUC at the time of 1-mg/kg intravenous injection.

F = [ΔAUCpo] / [DOSEpo] / [ΔAUCiv] / 1 × 100 (%)

Sapropterin Lot #s:8886202, 8885Y05

(mean value ± standard error, n = 3)

Figure 22: Schedule of Events

| | Open-Label Treatment | | | | | Follow-up |
|---|---|---|---|---|---|---|
| **Visit** | **Screening** | **Wk 1** | **Wk 2** | **Wk 3** | **Wk 4** | **Wk 5** |
| Informed consent | X | | | | | |
| Weight | X | X[5] | | | | X |
| Vital signs | X | X | X | X | X | X |
| Physical examination | X | | | | | X |
| Clinical laboratory tests[1] | X | | | | | X |
| Pregnancy test[4] | X | X | | | X | X |
| Urine Drugs of Abuse Screen[2] | X | X | X | X | X | X |
| Concomitant medications | X | X | X | X | X | X |
| Adverse events | | X | X | X | X | X |
| Blood PK sampling[3] | | X | X | X | X | X |
| Dispense study drug | | X | X | X | X | |

[1] Clinical laboratory tests included hematology, chemistry, urinalysis, Hepatitis B & C, and HIV at screening. Hematology, chemistry and urinalysis only were repeated at study discharge. Approximately 20 mL of blood was collected at visits that included clinical laboratory tests.

[2] Urine drugs screen to include testing for amphetamines, benzodiazepines, barbiturates, cocaine, cannabinoids, and opiates.

[3] Pharmacokinetic samples were taken at the following timepoints during each treatment period: pre-dose, 0.5, 1.0, 1.5, 2.0, 2.5, 3.0, 3.5, 4.0, 5.0, 6.0, 8.0, 10.0, 12.0, 18.0, and 24.0 hours post dose. Approximately 80 mL of blood was drawn during each treatment period (5 mL per timepoint) for the PK analysis.

[4] Additional urine pregnancy tests were performed at any visit at which pregnancy status was in question, and serum pregnancy tests were performed in the event of any positive or equivocal urine pregnancy test results.

[5] Weight at the Week 1 treatment period was used to calculate dose.

Mean Plasma Concentrations of $BH_4$ after Oral Administration of 10 mg/kg of Phenoptin as Dissolved and Intact Tablets under Fasted Conditions and Intact Tablets under Fed Conditions to Healthy Volunteers – Linear Axes

Mean Plasma Concentrations of $BH_4$ after Oral Administration of 10 mg/kg of Phenoptin as Dissolved and Intact Tablets under Fasted Conditions and Intact Tablets under Fed Conditions to Healthy Volunteers – Semi-Logarithmic Axes

FIGURE 25

Summary of Pharmacokinetic Parameters for $BH_4$ after Oral Administration of 10 mg/kg of Phenoptin as Dissolved and Intact Tablets under Fasted Conditions and Intact Tablets under Fed Conditions to Healthy Volunteers

| Parameter[1] | Dissolved Tablet Fasted | Intact Tablet Fasted | Intact Tablet Fed |
|---|---|---|---|
| Cmax (ng/mL) | 80.3 ± 63.3 [30]<br>(69.4) | 91.2 ± 36.3 [30]<br>(84.0) | 121 ± 33.6 [30]<br>(116) |
| Tmax (h) | 4.00 [30]<br>(2 - 6) | 3.50 [30]<br>(1 - 5) | 4.00 [30]<br>(1 - 5) |
| AUC(0-t) (h•ng/mL) | 479 ± 292 [30]<br>(420) | 550 ± 214 [30]<br>(505) | 709 ± 221 [30]<br>(675) |
| AUC(inf) (h•ng/mL) | 597 ± 336 [22]<br>(528) | 704 ± 202 [19]<br>(670) | 825 ± 256 [23]<br>(784) |
| $\lambda z$ ($h^{-1}$) | 0.2101 ± 0.1326 [22] | 0.2099 ± 0.0942 [19] | 0.2104 ± 0.0918 [23] |
| t½ (h) | 5.31 ± 4.42 [22] | 4.47 ± 3.37 [19] | 4.28 ± 2.79 [23] |

[1]Mean ± standard deviation except for Tmax for which the median is reported. Numbers in square brackets are the number of subjects for which the parameter could be estimated and numbers in parentheses are the geometric means for Cmax, AUC(0-t), and AUC(inf) and the ranges for Tmax.

FIGURE 26

Statistical Comparison of Pharmacokinetic Parameters for $BH_4$ after Oral Administration of 10 mg/kg of Phenoptin as Dissolved and Intact Tablets under Fasted Conditions and Intact Tablets under Fed Conditions to Healthy Volunteers

| Parameter | Geometric Mean Ratio (%)[1] | | | |
|---|---|---|---|---|
| | Estimate | 90% Confidence Interval | | |
| Intact vs. Dissolved Tablet (Fasted) | | | | |
| Cmax | 120.98 | 104.21 | → | 140.44 |
| AUC(0-t) | 120.33 | 104.12 | → | 139.06 |
| AUC(inf) | 118.04 | 98.16 | → | 141.96 |
| Intact Tablet — Fed vs. Fasted | | | | |
| Cmax | 138.63 | 119.42 | → | 160.93 |
| AUC(0-t) | 133.69 | 115.68 | → | 154.50 |
| AUC(inf) | 125.61 | 104.29 | → | 151.30 |

[1]Based on analysis of natural log-transformed data.

Stability of BH4 (1 mg/mL) in 5% mannitol aqueous solution

Dissolution Profile GMO Capsule Prototype

Dissolution Profile of Bioadhesive Tablet Prototype (80 mg BH4)

Dissolution Profile of Sustained Release Prototype (80 mg SAP-2HCl) with 20% HPMC of various viscosity grade Dissolution Profile of Sustained Release Prototypes (80 mg BH4) containing 20% to 40% Methocel K100M CR Schematic Diagram of Floating Dosage Form Dissolution Profile of Floating System Prototype (80 mg BH4) with Varying Levels of PEG Coating Schematic Diagram of Gas Generating Dosage Form Stability of BH4 in pH 4 Buffer in the Presence and Absence of Antioxidants and Sparging with Argon Stability of BH4 in pH 7 Buffer in the Presence and Absence of Antioxidants and Sparging with Argon Stability of BH4 Remaining in pH 4 Buffer Solution with Time as a Function of Concentration

METHODS OF ADMINISTERING TETRAHYDROBIOPTERIN

Matter enclosed in heavy brackets [ ] appears in the original patent but forms no part of this reissue specification; matter printed in italics indicates the additions made by reissue.

CROSS REFERENCE TO RELATED APPLICATIONS

This application is a continuation of U.S. patent application Ser. No. 12/329,828 filed Dec. 8, 2008, which in turn is a continuation of International Application No. PCT/US08/060,041, filed Apr. 11, 2008, which claims priority to U.S. Provisional Application Nos. 60/922,821, filed Apr. 11, 2007, and 61/019,753, filed Jan. 8, 2008, the disclosures of which are incorporated herein by reference in their entirety.

BACKGROUND

1. Field

The present invention is generally directed to compositions and methods for treating BH4-responsive disorders, and methods and compositions for detecting and quantitating biopterins.

2. Background of the Related Technology

Tetrahydrobiopterin (referred to herein as BH4) is a biogenic amine of the naturally-occurring pterin family that is a cofactor for a number of different enzymes, including phenylalanine hydroxylase (PAH), tyrosine hydroxylase, tryptophan hydroxylase and nitric oxide synthase. Pterins are present in physiological fluids and tissues in reduced and oxidized forms, however, only the 5,6,7,8, tetrahydrobiopterin is biologically active. It is a chiral molecule and the 6R enantiomer of the cofactor is known to be the biologically active enantiomer. For a detailed review of the synthesis and disorders of BH4 see Blau et al., 2001 (Disorders of tetrahydrobiopterin and related biogenic amines. In: Scriver C R, Beaudet A L, Sly W S, Valle D, Childs B, Vogelstein B, eds. The Metabolic and Molecular Bases of Inherited Disease. 8th ed. New York: McGraw-Hill, 2001: 1275-1776).

Fiege, et al., Molecular Genetics and Metabolism 81:45-51 (2004) studied pharmacokinetics of orally administered tetrahydrobiopterin (BH4) and suggested a "rather large variability of orally administered BH4, probably due to different absorption in the gut and/or to the first passage effect."

Use of tetrahydrobiopterin has been proposed for treating a variety of different disease states, and there exists a need for alternative and improved methods of administering this drug.

SUMMARY OF THE INVENTION

The present invention relates to methods of administering 6R-(L-erythro)-5,6,7,8-tetrahydrobiopterin (BH4), or a pharmaceutically acceptable salt thereof, in a manner that improves or maximizes its oral bioavailability and/or improves or optimizes the consistency of oral bioavailability from one administration to the next. Such methods can be applied in the treatment of any BH4-responsive disorder, including metabolic diseases, cardiovascular diseases, anemia, and neuropsychiatric disorders. The methods of the invention advantageously allow better control of clinical symptoms, e.g. reduced fluctuation in plasma phenylalanine levels, blood pressure, neurotransmitter levels, or other clinical parameters.

As used herein, BH4 refers to 6R-(L-erythro)-5,6,7,8-tetrahydrobiopterin. The term BH4 as used herein is also to be understood to optionally mean a pharmaceutically acceptable salt of 6R-(L-erythro)-5,6,7,8-tetrahydrobiopterin, unless the context dictates otherwise.

In a first aspect, the invention provides methods of orally administering to a patient in need thereof a purified preparation of BH4.

In an exemplary embodiment, the methods comprise the step of informing the patient that absorption of tetrahydrobiopterin is increased when it is ingested with food compared to when ingested without food. In some embodiments, the patient is informed that ingestion shortly following a meal, for example, a high-fat, high-calorie meal, results in an increase in any one, two, three or all of the following parameters: mean plasma concentration, Cmax, AUC, AUC(0-t) and/or AUC(inf). In exemplary embodiments, the patient is informed that administration of BH4 with a high-fat meal increases Cmax and AUC compared to administration of BH4 without food (in a fasting condition). In some embodiments, the relative increase can be at least 20% or 30% or more.

In alternative embodiments or in addition to the preceding embodiments, the method of administering tetrahydrobiopterin comprises informing the patient that absorption of tetrahydrobiopterin is increased when ingested as an intact tablet compared to when ingested after being dissolved in liquid. In some embodiments, the patient is informed that ingestion of intact tablets results in an increase in any of the following parameters: mean plasma concentration, Cmax, AUC, AUC (0-t) or AUC(inf). In exemplary embodiments, the patient is informed that administration of BH4 as an intact tablet increases Cmax and AUC compared to administration of BH4 after being dissolved in a liquid. In some embodiments, the relative increase can be at least 20% or more.

Any of the preceding methods may be carried out by providing or administering tetrahydrobiopterin in a container containing printed labeling informing the patient of the change in absorption parameters described above.

Optionally, the methods of the invention also comprise the step of providing to the patient in need thereof a therapeutically effective amount of tetrahydrobiopterin. The therapeutically effective amount will vary depending on the condition to be treated, and can be readily determined by the treating physician based on improvement in desired clinical symptoms.

In one exemplary embodiment, such methods involve administering BH4 in a dissolved form, wherein the formulation is dissolved in a liquid including but not limited to water, orange juice and apple juice. In one exemplary embodiment, dissolved BH4 is administered to the patient in a fasted condition, i.e., on an empty stomach. The invention further contemplates that the dissolved BH4, is administered at a specified time including but not limited to morning, day, night, same time of the day, on an empty stomach, one or more times a day. In exemplary embodiments, the composition is administered to the patient when the stomach is empty, for example, at least 30 minutes, 45 minutes, or at least one hour before, and/or at least 90 minutes, or two hours, or 2.5 hours, or three hours after a meal. Thus, BH4 may be ingested as a liquid product or pre-dissolved from a solid or semisolid dosage form prior to ingestion. In a further embodiment, BH4 may also be dissolved in the oral cavity from a solid or semisolid dosage form prior to swallowing the dissolved solution.

In another exemplary embodiment, such methods involve administering BH4 in a solid dosage form including but not limited to tablets, capsules, candies, lozenges, powders, and granules, or semisolid form, including but not limited to oral sprinkle into jelly, that is swallowed without dissolving in a liquid including but not limited to water, orange juice and apple juice, before swallowing. In one embodiment, swallowed BH4 is administered to the patient in a fasted condition, i.e. on an empty stomach. The invention further contemplates that the BH4 swallowed as a solid or semisolid dosage form, is administered at a specified time including but not limited to morning, day, night, same time of the day, on an empty stomach, one or more times a day. In exemplary embodiments, the composition is administered to the patient when the stomach is empty, for example, at least 30 minutes, 45 minutes, or at least one hour before, and/or at least 90 minutes, or two hours, or 2.5 hours, or three hours after a meal.

In another embodiment, such methods involve administering BH4, whether swallowed as a solid or semisolid dosage form, or dissolved in a liquid, with food, e.g. a high-fat food or a high-fat and/or high-calorie meal. The invention further contemplates that BH4, whether swallowed or dissolved, is administered at a specified time including but not limited to morning, day, night, same time of the day, with food, e.g. a high-fat food or a high-fat and/or high-calorie meal, one or more times a day. In an exemplary embodiment, BH4 is ingested once daily as a solid dosage form just after meals. In a preferred embodiment the solid dosage form is a formulated tablet or capsule. In more exemplary embodiments, BH4 is ingested within approximately 0 to 30 minutes, or 5 to 20 minutes, of eating a meal. Regardless of whether it is ingested as a solid dosage form, liquid dosage form or as a dissolved solution, the in vivo exposure (or bioavailability) of BH4 is higher when ingested just after meals compared to fasting controls.

The BH4 and the food may be ingested at approximately the same time, or the BH4 may be ingested before or after the food. The period of time between consuming the food and taking BH4, either swallowed or dissolved, may be at least 5 minutes. For example, BH4 may be administered 60 minutes, 30 minutes, 25 minutes, 20 minutes, 15 minutes, 10 minutes, or 5 minutes before or after a meal.

In another embodiment, for some patients, e.g. adults, or some disease states, e.g. cardiovascular diseases or other diseases associated with NOS dysfunction, the methods of the invention involve administering an intact tablet rather than dissolving the tablet in a liquid, in order to improve bioavailability.

In a second aspect, the invention contemplates a method of stabilizing BH4 in a patient's intestinal tract by decreasing intestinal pH, e.g. using proton exchange polymers. Corresponding products comprising BH4 and acidifying excipients, such as proton exchange polymers, are also contemplated.

A third aspect of the invention contemplates a method of increasing gut residence time for BH4, including but not limited to slowing of gut motility using an agent which slows gut motility, such as a fatty acid and/or a glycerol fatty acid ester. Such hydrophobic agents can increase the length of time that BH4 remains in the gut and can increase the amount of BH4 that gets absorbed. The length of time that BH4 remains in the gut, when formulated with such agent(s), can be at least one and a half times, at least two times, at least three times, at least four times, or at least five times longer than a BH4 formulation not having such an agent. Suitable fatty acids include oleic acid, stearic acid, arachidic acid, palmitic acid, archidoic acid, linoleic acid, linolenic acid, erucidic acid, myristic acid, lauric acid, myristolic acid, and palmitolic acid. Also contemplated to increase gut residence time for BH4 is inducement of gastric retention using alginic acid, and bioadhesion using polycarbophil. Corresponding products comprising BH4 and agents that slow gut motility are contemplated.

A fourth aspect of the invention contemplates a method of modifying the release of BH4 using a sustained release formulation such as HPMC, carbomer, etc. Corresponding products that are sustained release formulations are contemplated.

In a fifth aspect, the invention contemplates administering BH4 in sterile liquid or sterile solid dosage form via routes other than oral administration including but not limited to topical, intravenous, subcutaneous, intramuscular, intrathecal, ophthalmic, and inhalational routes of administration. Corresponding compositions and kits suitable for such routes of administration, and methods of making the same, are contemplated. For example, a transdermal or buccal patch for transdermal or buccal administration, respectively, comprising BH4 is contemplated. Sublingual tablets comprising BH4 are also contemplated. Suitable kits are contemplated, including an inhaler device comprising BH4, or a kit comprising BH4 and a dropper or sprayer.

One embodiment includes a liquid formulation of tetrahydrobiopterin (BH4) or a pharmaceutically acceptable salt thereof, including an aqueous solution of BH4 or pharmaceutically acceptable salt thereof, an antioxidant, and a pH buffer.

Another embodiment includes a method of making a liquid formulation of tetrahydrobiopterin (BH4) or a pharmaceutically acceptable salt thereof, including providing an aqueous solution containing BH4 or pharmaceutically acceptable salt thereof, adding an antioxidant and a pH buffer to the solution containing BH4 or pharmaceutically acceptable salt thereof, sparging the aqueous solution containing BH4 or pharmaceutically acceptable salt thereof, before or after addition of antioxidant and pH buffer, with an inert gas or carbon dioxide, and sealing the sparged solution containing BH4 or pharmaceutically acceptable salt thereof, antioxidant, and pH buffer in a container.

In a sixth aspect, the invention contemplates an improved method of measuring BH4 by utilizing tandem mass spectrometry and calculating the amount of reduced biopterin. Such methods can provide detection of BH4 to a sensitivity for BH4 in the range of 5-1000 ng/mL, with an accuracy and precision as exemplified by a coefficient of variation (CV) % below 15% (20% at the lower limit of quantitation, LLOQ). In an exemplary embodiment, a method of measuring BH4 using HPLC (RP) coupled with tandem mass spectrometry (LC/MS/MS) comprises the steps of: (1) subjecting samples of blood, plasma, tissue homogenates, or urine to oxidation; (2) subjecting the oxidized samples to iodometry; (3) passing said oxidized samples through an ion exchange column; (4) measuring total and oxized biopterin in said samples using HPLC and tandem mass spectrometry; and calculating the amount of reduced biopterin as the difference between said total biopterins less said oxidized form. In one embodiment, samples are treated with acidic oxidation, wherein the method comprises the steps of (1) treating said samples with KCl, HCl or TCA; (2) subjecting said acid-oxidized samples to iodometry; (3) running said oxidized samples through an ion exchange column; (4) measuring total biopterin comprising 6R-BH4, R-q-DHBP (which is immediately reduced in vivo to 6R-BH4 such that the measured reduced biopterin is based mainly upon 6R-BH4), DHBP, and BP in said samples using HPLC and tandem mass spectrometry. In another embodiment, samples are treated by alkaline oxidation, wherein the method comprises: (1) treating said samples with KI, I or NaOH; (2) subjecting said alkaline oxidized samples to acidification with HCl or TCA; (3) subjecting said oxidized samples iodometry; (4) running said samples through an ion exchange column; (5) measuring oxidized biopterin comprising DHBP and BP using HPLC and tandem mass spectrometry; and (6) calculating the amount of reduced biopterin (6R-BH4+R-q-DHBP) as the difference between total biopterins less the oxidized form.

Another aspect of the invention is a mobile phase solution for reverse-phase HPLC separation of dihydrobiopterin, biopterin, and analogs thereof, including an aqueous solution including methanol, sodium acetate, citric acid, EDTA, and 1,4-dithioerythritol. Similarly contemplated is a method of separating dihydrobiopterin and biopterin, or analogs thereof, from a mixture containing both base and dihydro forms, including performing reverse phase HPLC using a mobile phase comprising an aqueous solution including methanol, sodium acetate, citric acid, EDTA, and 1,4-dithioerythritol, on a mixture containing dihydrobiopterin and biopterin, or an analog of dihydrobiopterin and an analog of biopterin.

Another aspect of the invention is a method of quantitating biopterins in a mixture of biopterin species, including providing a mixture comprising biopterin and at least one of dihydrobiopterin and tetrahydrobiopterin, or analogs of biopterin and at least one of dihydrobiopterin and tetrahydrobiopterin, separating the biopterin species in the mixture by reverse phase HPLC, and in the case of tetrahydrobiopterin and analogs thereof, performing electrochemical detection by oxidizing the tetrahydrobiopterin and analogs thereof present by a first electrode to quinonoid dihydrobiopterin forms, followed by reducing the quinonoid forms back to tetrahydrobiopterin and analogs thereof present at a second electrode, and measuring current generated by the reduction reaction to determine the concentration of species, and/or in the case of dihydrobiopterin, analogs thereof, biopterin, or analogs thereof, measuring such species by fluorescence detection following post-column oxidation of dihydrobiopterin species to biopterin.

For the compositions and methods described herein, preferred components, and compositional ranges thereof, can be selected from the various examples provided herein.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

FIG. 16 is a flow chart for the measurement of biopterin.

FIG. 17 is a summary of the validation of the biopterin assay.

FIG. 19 shows plasma biopterin concentration and reduced-form ratio after single-dose administration of sapropterin (BH4) to rats.

FIG. 21 is a table showing pharmacodynamic parameters of total biopterins in plasma after single-dose administration of sapropterin (BH4) to monkeys.

FIG. 22 shows the schedule of events for the evaluation of safety.

FIG. 25 shows a table summarizing the pharmacokinetic parameters for $BH_4$ after oral administration of 10 mg/kg of BH4 as dissolved and intact tablets under fasted conditions and intact tablets under fed conditions to healthy volunteers.

FIG. 26 shows a statistical comparison of pharmacokinetic parameters for $BH_4$ after oral administration of 10 mg/kg of BH4 as dissolved and intact tablets under fasted conditions and intact tablets under fed conditions to healthy volunteers.

DESCRIPTION OF THE PREFERRED EMBODIMENTS

Figure 1:
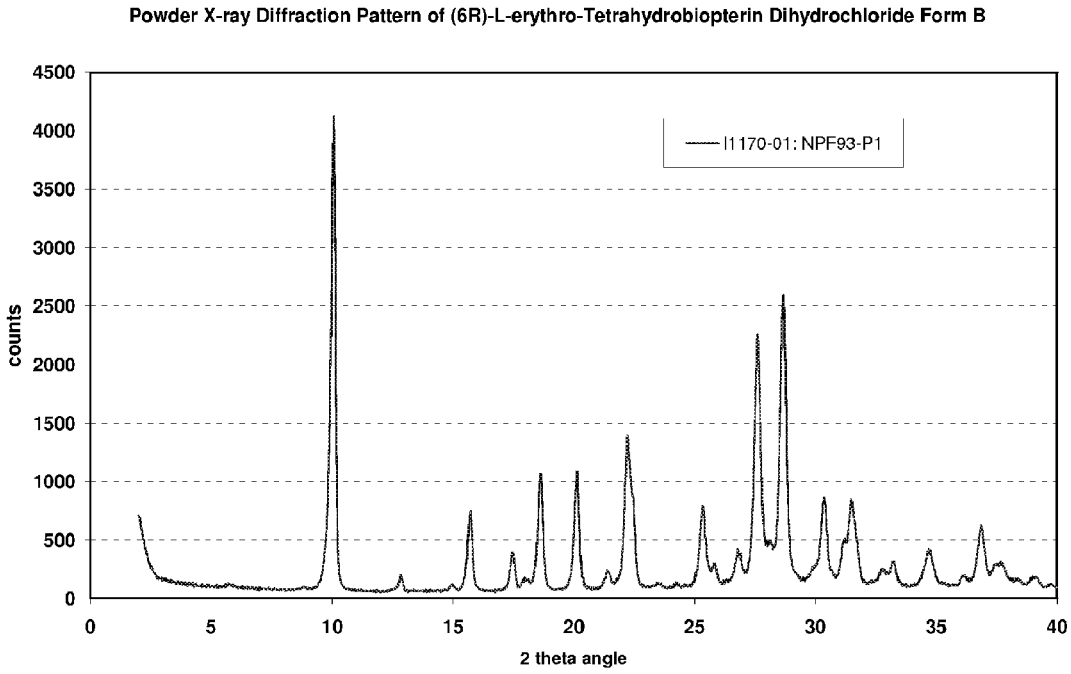
FIG. 1 shows a powder X-ray diffraction pattern characteristic of crystal polymorph form B of 6R-(L-erythro)-5,6,7,8-tetrahydrobiopterin.

The invention provides improved methods of orally administering a purified preparation of 6R-(L-erythro)-5,6,7,8-tetrahydrobiopterin, including a pharmaceutically acceptable salt thereof. The invention is based on the finding that orally administered tetrahydrobiopterin (BH4) has low gastrointestinal absorption, which is a major contributing factor to the low bioavailability of BH4.

The chemical structure of 6R-(L-erythro)-5,6,7,8-tetrahydrobiopterin (BH4) is shown below:

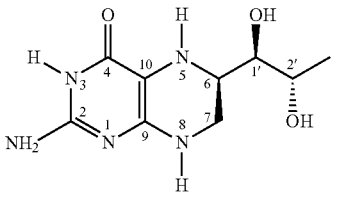

Tetrahydrobiopterin is a water soluble organic compound with low lipid solubility. Based on an in silico experimental analysis using BioLoom software (version 1.5 from Biobyte Corp in Claremont Calif), the octanol-water partition coefficient of BH4 was determined to be −1.17. Optimal penetration of biological membranes as approximated by the octanol/water partition coefficient occurs at around a log P of 2 or 100-× fold higher lipid solubility. Although a low ClogP allows this substrate to solubilize readily under physiological conditions, the ability of the substrate to penetrate bilipid layers within biological membranes is restricted, which may limit oral availability.

In vivo studies in rats and monkeys described herein showed that only 8-11% of BH4 is absorbed in the gut with the majority being excreted in the feces when compared to intravenous administration of BH4 at similar doses. Such variability in absorption of BH4 was also shown in a study described herein on the effect of food on the bioavailability of BH4 in healthy humans. Although the administration of BH4 in water and orange juice under fasted conditions resulted in comparable mean plasma concentrations and mean values for Cmax and AUC(0-t), the administration of BH4 concurrent with a high fat, high caloric meal resulted in a significant increase in the mean plasma concentrations and mean values for Cmax and AUC(0-t) when BH4 was administered in water.

Although there is ample literature describing increased bioavailability in fed conditions, this food effect is typically seen with lipophilic (i.e., lipid soluble) water-insoluble drugs and not usually with high water soluble active substance such as BH4. The usual explanation for increases in bioavailability under fed conditions for lipophilic compounds is that high fat meals help solubilize the drug since "like dissolves like" and this makes it available for absorption. Another possible explanation is that high fat meals stimulate the secretion of bile acids which are natural bio-surfactants that help solubilize and emulsify the fats we eat to aid their digestion. These bile acids are also thought to solubilize water-insoluble compounds thereby making them available for absorption. However, BH4 does not need solubilization to be absorbed since its solubility is greater than 1000 mg/mL and the compound is one of the most soluble drugs known. Therefore the enhancement of its bioavailability by high fat, high-energy meals is not consistent with such known mechanism.

However, administration as a solid or semi-solid dosage form and/or with a high-fat meal may maximize bioavailability by increasing the residence time of BH4 in the acidic milieu of the stomach and upper gastrointestinal tract (GIT) where BH4 is chemically stable. The stability of BH4 decreases with increasing pH and its half-life in pH 6.8 buffer solution, which is roughly the pH of the small intestine, is about 15 minutes. At pH 3.1, which is within realm of the typical pH of the stomach in normal volunteers, the stability of BH4 at a concentration of 1 mg/mL is over 3 hours. The chemical stability of BH4 may further increase when the pH of the stomach drops below pH 3.1. Therefore prolonged stomach residence time provides intact drug to the stomach wall for absorption, whereas rapid emptying into the intestine degrades BH4 and is thus not available to be absorbed.

Thus, to maximize oral bioavailability of BH4 at each administration, BH4 should be taken with food, e.g., a high fat food or a high fat and/or high calorie meal. Alternatively, to maximize consistency of oral bioavailability between administrations, BH4 should be taken on an empty stomach (e.g., 1 hour before or 2 hours after a meal).

As used herein, the term "bioavailability" refers to the fraction of an administered dose of a drug entering systemic circulation. If the drug were administered intravenously, then its bioavailability theoretically would be 100%. However, if the drug were administered via other routes (such as orally), then its bioavailability would be less than 100% as a result of, for example, incomplete absorption in the GI tract, degradation or metabolism prior to absorption, and/or hepatic first pass effect.

The term "high fat meal" refers generally to a meal of at least about 700 kcal and at least about 45% fat (relative percentage of kcal which are fat), or alternatively at least about 900 kcal and at least about 50% fat. The term "high fat food" refers generally to a food comprising at least 20 g of fat, or at least 25, 30, 35, 40, 45, or 50 g of fat, and/or at least about 45% or 50% fat. One FDA Guidance defines a "high-fat meal" as approximately 50% of total caloric content of the meal, whereas a "high-calorie meal" is approximately 800 to 1000 calories. The FDA recommends a high-fat and high-calorie meal as a test meal for food-effect bioavailability and fed bioequivalence studies. This test meal should derive approximately 150, 250, and 500-600 calories from protein, carbohydrate and fat, respectively. An example test meal consists of two eggs fried in butter, two strips of bacon, four ounces of hash brown potatoes and eight ounces of whole milk. Substitution is possible if a similar amount of calories from protein, carbohydrate, and fat has comparable meal volume and viscosity (Guidance for Industry, Food-Effect Bioavailability and Fed Bioequivalence Studies, U.S. Department of Health and Human Services, Food and Drug Administration, Center for Drug Evaluation and Research (CDER), December 2002).

In a first aspect, the invention provides methods of orally administering a purified preparation of 6R-(L-erythro)-5,6,7,8-tetrahydrobiopterin (BH4), including a pharmaceutically acceptable salt thereof.

In some embodiments, the methods involve informing the patient that administration of tetrahydrobiopterin with food has an effect on pharmacokinetics. In an exemplary embodiment, the methods comprise the step of informing the patient that absorption of tetrahydrobiopterin is increased when it is ingested with food compared to when ingested without food. In some embodiments, the patient is informed that ingestion shortly following a meal, for example, a high-fat, high-calorie meal, results in an increase in any one, two, three or all of the following parameters: mean plasma concentration, Cmax, AUC, AUC(0-t) and/or AUC(inf). In exemplary embodiments, the patient is informed that administration of BH4 with a high-fat meal increases Cmax and AUC compared to administration of BH4 without food (in a fasting condition). In some embodiments, the relative increase can be at least 20% or 30% or more.

In alternative embodiments or in addition to the preceding embodiments, the method of administering tetrahydrobiopterin comprises informing the patient that absorption of tetrahydrobiopterin is increased when ingested as an intact tablet compared to when ingested after being dissolved in liquid. In some embodiments, the patient is informed that ingestion of intact tablets results in an increase in any of the following parameters: mean plasma concentration, Cmax, AUC, AUC (0-t) or AUC(inf). In exemplary embodiments, the patient is informed that administration of BH4 as an intact tablet increases Cmax and AUC compared to administration of BH4 after being dissolved in a liquid. In some embodiments, the relative increase can be at least 20% or more.

Any of the preceding methods may be carried out by providing or administering tetrahydrobiopterin in a container containing printed labeling informing the patient of the change in absorption parameters described above.

Optionally, the methods of the invention also comprise the step of providing to the patient in need thereof a therapeutically effective amount of tetrahydrobiopterin. The therapeutically effective amount will vary depending on the condition to be treated, and can be readily determined by the treating physician based on improvement in desired clinical symptoms.

In one exemplary embodiment, such methods involve administering BH4 in a dissolved form, wherein the formulation is dissolved in a liquid including but not limited to water, orange juice and apple juice. In one embodiment, dissolved BH4 is administered to the patient in a fasting condition, i.e., on an empty stomach. The invention further contemplates that the dissolved BH4, is administered at a specified time including but not limited to morning, day, night, same time of the day, on an empty stomach, one or more times a day. In exemplary embodiments, the composition is administered to the patient when the stomach is empty, for example, at least 30 minutes, 45 minutes, or at least one hour before, and/or at least 90 minutes, or two hours, or 2.5 hours, or three hours after a meal. Thus, BH4 may be ingested as a liquid product or pre-dissolved from a solid or semisolid dosage form prior to ingestion. In a further embodiment, BH4 may also be dissolved in the oral cavity from a solid or semisolid dosage form prior to swallowing the dissolved solution.

These approaches maximize absorption rate and bioavailability by ensuring that BH4 is fully dissolved in solution or biologic fluids before it is delivered to its absorption sites, which are primarily the stomach and the intestine. Dissolution of active pharmaceutical ingredients or drug in solution is a prerequisite to absorption into the systemic (blood and lymphatic) circulation. When solid dosage forms such as tablets and capsules are administered orally, they go through a sequential series of steps such as disintegration into granules, de-aggregation into powders and dissolution prior to absorption into the systemic circulation. These series of steps are bypassed by administering liquid, semisolid and fast dissolving solid dosage forms. Thus the active substance is available earlier for absorption, and because there is no guarantee that a solid dosage form will release all the active substance contained within it before it transits through the absorptive sites, the formulations in which the active substance is present in dissolved form before it reaches the absorptive sites usually exhibits the greater bioavailability.

These dosage forms reduce variability in blood levels because the variability is dosage form disintegration and dissolution in vivo in the human is obviated. The rate of in vivo disintegration and dissolution of a sold dosage form of BH4 targeted for immediate-release in the stomach depends on the human-to-human variability in the pH of the gastric fluid—fed and unfed (fasting)—and the strength of the agitation intensity of the stomach as determined by the strength of gastric motility and gastric emptying rates into the small intestine. Since liquid, semisolid, lozenge/candy and fast dissolving solid dosage forms do not have to be subjected to disintegration and dissolution, their blood levels are less variable than when BH4 is given as immediate release solid dosage forms (tablets and capsules).

In another exemplary embodiment, such methods involve administering BH4 in a solid dosage form including but not limited to tablets, capsules, candies, lozenges, powders, and granules, or semisolid form, including but not limited to oral sprinkle into jelly, that is chewed or swallowed without dissolving in a liquid including but not limited to water, orange juice and apple juice, before swallowing. In one embodiment, swallowed BH4 is administered to the patient in a fasting condition, i.e., on an empty stomach. The invention further contemplates that the BH4 swallowed as a solid or semisolid dosage form, is administered at a specified time including but not limited to morning, day, night, same time of the day, on an empty stomach, one or more times a day. In exemplary embodiments, the composition is administered to the patient when the stomach is empty, for example, at least 30 minutes, 45 minutes, or at least one hour before, and/or at least 90 minutes, or two hours, 2.5 hours, or three hours after a meal.

In another embodiment, such methods involve administering BH4, whether swallowed as a solid or semisolid dosage form, or dissolved in a liquid, with food, e.g. a high-fat food or a high-fat and/or high-calorie meal. The invention further contemplates that BH4, whether swallowed or dissolved, is administered at a specified time including but not limited to morning, day, night, same time of the day, with food, e.g. a high-fat food or a high-fat and/or high-calorie meal, one or more times a day. In an exemplary embodiment, BH4 is ingested once daily as a solid dosage form just after meals. In a preferred embodiment the solid dosage form is a formulated tablet or capsule. In more exemplary embodiments, BH4 is ingested within approximately 0 to 60 minutes, approximately 0 to 30, or 5 to 20 minutes of eating a meal. Regardless of whether it is ingested as a solid dosage form, liquid dosage form or as a dissolved solution, the in vivo exposure (or bioavailability) of BH4 is higher when ingested just after meals compared to fasting controls.

The BH4 and the food may be ingested at approximately the same time, or the BH4 may be ingested before or after the food. The period of time between consuming food, e.g., a high-fat food or a high-fat and/or high-calorie meal and taking BH4 either swallowed or dissolved may be at least 5 minutes. BH4 may be administered 60 minutes, 30 minutes, 25 minutes, 20 minutes, 15 minutes, 10 minutes, or 5 minutes after ingestion of a meal.

In another embodiment, for some patients, e.g. adults, or some disease states, e.g. cardiovascular diseases or other diseases associated with NOS dysfunction, the methods of the invention involve administering an intact tablet rather than dissolving the tablet in a liquid, in order to improve bioavailability.

Administration of BH4 according to the methods of the invention results in mean plasma concentrations and/or rate of gastrointestinal absorption and/or mean values for Cmax and/or AUC(0-t) and/or AUC (inf) that exceeds the values when BH4 is administered under fasted conditions.

Administration of an intact tablet under fasted conditions resulted in an average 20% increase in Cmax and AUC relative to dissolved tablets. Administration of a dissolved tablet in either water or orange juice or an intact tablet after a high fat/high calorie meal resulted in increases in Cmax and AUC that ranged from approximately 30% (intact tablet) to 80% (water). Administration of BH4 as an intact tablet following a high fat and high calorie meal resulted in an approximate 30% increase in the extent of absorption compared to administration without food. Administration of BH4 as an intact tablet resulted in an approximate 20% increase in the extent of absorption compared to administration of dissolved tablets.

"Mean plasma concentration" means the average of readings of concentration in a series of plasma samples.

"Cmax" means the maximum observed plasma concentration.

"AUC" means the area under the plasma concentration-time curve.

"$AUC_{0-t}$" means the area under the plasma concentration-time curve from time 0 to the time of the last measurable concentration.

"$AUC_{(inf)}$" means the calculated area under the plasma concentration-time curve from time 0 to infinity.

The "rate of gastrointestinal absorption" of BH4 is estimated from the area under the plasma total biopterin concentration increase (ΔCp)-time curve (ΔAUC) after the administration of BH4 using the following formula:

$$\text{Absorption rate}(\%)=(\Delta\text{AUC after p.o. dose}/\Delta\text{AUC after i.v. dose})\times(\text{i.v. dose/p.o. dose}\times 100)$$

Preferably at least 99.5% pure 6R-BH4 is used. Any salt, including the dihydrochloride salt, and any crystalline form of BH4 may be utilized according to the methods and compositions of the invention. A variety of salts and crystalline forms are described in U.S. Patent Publication No. 2006/0040946, incorporated herein by reference in its entirety, and/or the stable solid formulation described in Int'l Publication No. WO 06/55511, also incorporated herein by reference in its entirety. The various crystalline forms may conveniently be formed into a tablet, powder or other solid for oral administration.

In a second aspect, the invention contemplates a method of stabilizing BH4 by decreasing intestinal pH using proton exchange polymers. BH4 is administered orally daily as a solid or liquid dosage form comprising inactive ingredients that enhance the stability of BH4 beyond the stomach by lowering the pH of the intestine and thus preserving BH4 from being oxidized rapidly. Since BH4 is more stable in acidic media than in basic media, acidifying excipients/inactive ingredients are included in solid dosage (tablets, capsules, etc) formulations of BH4 to lower the pH of the intestinal fluids and thereby enhance the chemical stability. The larger area or window of the gastrointestinal tract (GIT) available for absorption optimizes the consistency of absorption by expanding the current limited window of absorption believed to be limited to the stomach and the duodenum to the intestine. Such dosage forms include but are not limited to effervescent tablets, powders and granules (to be resuspended in liquid before administration) and acidifier materials. Unlike small molecule acids, bulky polymeric acids remain in the GIT longer and are not absorbed by the GIT, but donate their protons to the GIT fluids to lower the environmental pH. Examples of excipients/inactive ingredients that comprise the formulation are carboxylic acid small molecules such as maleic, fumaric and citric acids or inorganic small molecules such phosphoric acid, acetic acid and their salt forms. Other examples are pharmaceutically acceptable acids such as polymeric carboxylic acid classes including polymethacrylic acids, carbomers, polycarbophil, Eudragits, acid forms of crosscarmelose and starch glycolic acid, etc. The formulations also contain additional excipients to enhance stability such as anti-oxidants (e.g., thiols such cysteine, N-acetyl cysteine, etc; ascorbic acid; methionine; etc.) and other excipients known in the trade to enable manufacturability and enhance the quality and performance attributes of the formulation.

A third aspect of the invention contemplates a method of increasing gut residence time for BH4, including but not limited to slowing of gut motility using an agent which is capable of slowing gut motility of BH4, such as a fatty acid and/or a glycerol fatty acid ester. Fatty acids can include oleic acid, stearic acid, arachidic acid, palmitic acid, archidoic acid, linoleic acid, linolenic acid, erucidic acid, myristic acid, lauric acid, myristolic acid, and palmitolic acid. Also contemplated for increasing gut residence time of BH4 are the inducement of gastric retention using alginic acid and bioadhesion using polycarbophil. In one embodiment, dosage forms of BH4 are administered as oral buoyant formulations that float and release BH4 in a defined fashion in the gastric fluid and are retained longer in the stomach because they are more resistant to gastric emptying from the stomach than formulations that are non-buoyant or dissolve rapidly in the stomach. This design approach is based on gastro-retention of the dosage form via the use of a gas-generating excipient within the dosage form, low-density excipients that render the dosage form buoyant in GIT fluids or a combination of a gas and low-density materials in a dosage form to enable the floating of the dosage form in the fluid contents of the GIT. Prolonged retention and release of the dosage form in the stomach milieu wherein BH4 is more stable in its acidic fluids will enhance both residence time of the dosage form in the stomach and the stability of BH4 and thus make BH4 available for a longer period absorption in the stomach and duodenum than standard tablet and capsule dosage forms. Formulations of BH4 will comprise of one or more antioxidants, excipients known in the field to enable manufacturing and disintegration/dissolution of the solid dosage form and additional excipients that generate a gas or mixture of gases (e.g., carbon dioxide) upon contact of the formulation with aqueous media and or GIT fluids. Water-soluble antioxidants are preferred, for example, ascorbic acid, methionine, and thiols (cysteine, N-acetyl cysteine and glutathione) or anti-oxidants that are converted to a soluble antioxidant in the GIT, e.g., ascorbyl palmitate which is converted to ascorbic acid in the GIT. Excipients added to the formulation include carbonates and bicarbonates that react directly with BH4 to form carbon dioxide and small and polymeric acids described previously to react with the carbonates and bicarbonates to produce additional carbon dioxide as needed.

In another embodiment, dosage forms of BH4 are administered that adhere for a prolonged time to the mucous surfaces of the GIT (i.e., bioadhesive formulation), preferably in, but by no means limited to the stomach where due to the acidity of gastric fluids, BH4 is more stable than in the intestine. BH4 is released in a controlled manner from the bioadhesive dosage form. The solid dosage form is designed to contain BH4, one or more antioxidants, excipients known in the field to enable the manufacturing of quality dosage forms and control the disintegration/dissolution of the dosage form and a bioadhesive additive such as polycarbophil in its free acid form or as a salt form. Other polymeric acids such as polymethacrylic acids, carbomers and cellulose derivatives, e.g., HPMC, HPC, etc. may be combined with or substituted for polycarbophil. The antioxidants are preferably soluble, for example, ascorbic acid, methionine, cysteine, N-acetyl cysteine and glutathione or can be converted to a soluble antioxidant such as ascorbic acid in the GIT, e.g., ascorbyl palmitate. In one embodiment, the components of the formulation are blended together and manufactured as a solid dosage form, e.g., tablets or capsules. The solid dosage form may be enteric coated to deliver BH4 past the stomach into the intestine or not enteric coated designed to release BH4 in the stomach. In another embodiment, the components of the solid dosage form may be subdivided into different portions and the various portions are blended separately before they are processed to form multilayered dosage forms. The multilayered dosage form may contain the bioadhesive and a few excipients in the outermost layer of a tablet, wrapped around other layers that contain BH4 (i.e., active region inside a bioadhesive envelope) or as a wrap-around cylindrical plug filled into a capsule wherein one or more other layers are assembled beneath or within the bioadhesive envelope. Alternatively, the bioadhesive and other layers in the tablet or capsule plugs may be layered in a parallel bi- or multilayer configuration. These designs allow the bioadhesive to interact with the GI membrane or GI membrane mucus to anchor the dosage form to the membrane slowing down its transit through the GI tract and thus increasing residence time. Such dosage forms may also be enteric coated. Yet another embodiment of the method used with BH4 is to employ polymeric inactive ingredients (excipients) with functional groups that bind to GIT mucus to delay the transit of the dosage form through the GIT. Dosage forms of BH4 are formulated with thiolated polymer excipients (polymer-SH) such as polycarbophil-cysteine, polypolymethacrylic acid-cysteine, carboxymethyl cellulose-cysteine, chitosan derivatives-cysteine, etc. These thiolated polymers confer both bioadhesive and anti-oxidant properties on BH4 considerably enhancing absorption. Other excipients included in these formulations are antioxidants and performance and manufacture-aiding excipients.

In yet another embodiment, oral dosage forms containing inactive excipients or active ingredients are used to slow gastric motility. Slowing down the transit of BH4 dosage form through the GIT tract will increase the residence time of the molecule and thus enable a larger fraction of the administered dose to be absorbed. Generally regarded as safe (GRAS) excipients employed in oral formulations to delay gastric emptying and/or delay intestinal motility preferably comprise dietary fats such as fatty acids, glycerides of fatty acids, and derivatives of fatty acids and glycerides such as Cremophor™ (polyoxyl castor oil derivatives), etc. Active excipients include agents that slow gut motility such as general or selective ($M_3$) antimuscarinic or anticholinergic agents.

A fourth aspect of the invention contemplates a method of modifying the release of BH4 using a sustained release formulation such as HPMC, carbomer, etc. This concept comprises delivering BH4 dosage forms to the GI tract by modifying or altering the release of BH4 from immediate-release to slow, prolonged, controlled and or timed release. Slow, prolonged and controlled release is achieved using excipients known in the art and BH4 is protected within the delivery system from chemical degradation by the presence of stability enhancers such as anti-oxidants. Such methods can maximize bioavailability since BH4 is stabilized within the formulation and in the environment surrounding the formulation to enable the active molecule to absorbed intact into the systemic circulation as the formulation transits the entire length of the GIT. This approach provides a larger window of the GIT for absorption and does so by preventing the degradation of BH4 in the higher pH milieu so that BH4 is available to be absorbed. Antioxidants will be included in the formulation to protect the drug from degrading in intestinal fluids due to near neutral pH of the intestinal fluids. Slow, prolonged and controlled delivery will also deliver BH4 to low oxygen tension regions of the GIT. Timed release is achieved using excipients known in the art such as pH sensitive polymers that dissolve only when the pH reaches a value wherein the polymer is soluble.

In another embodiment, the invention contemplates enteric coating of the BH4 dosage form to ascertain whether including acidic excipients in a formulation of BH4 does indeed increase absorption of BH4 by lowering the pH of the intestine and thus stabilizing BH4 in the intestine to be available for absorption. Thus, enteric coating will be used to keep the excipients and drug together at the site where the excipient is expected to protect BH4. If the BH4 dosage form were allowed to disintegrate in the stomach, the acidic excipients may not empty together into the stomach and may not provide protection.

Enteric coating protects compounds susceptible to acid-catalyzed degradation in the stomach from getting degraded by the acid in the stomach. Enteric coating materials prevent the tablet or capsule from releasing the active compound in the stomach because the enteric coating materials are insoluble in acid. Once the enteric-coated dosage form reaches the intestine where the pH value varies from pH 5-8, the materials become soluble and release the active substance in the intestine. In contrast, sustained release formulations are designed to release medicaments over as long a length/area of the GIT as possible. Coating a sustained release formulation to release just past the stomach may be necessary only if the medicaments contained in it are acid-labile.

In a fifth aspect, the invention contemplates administering BH4 in sterile liquid or sterile solid dosage form via routes other than oral administration including but not limited to topical, intravenous, subcutaneous, intramuscular, intrathecal, ophthalmic, and inhalational routes of administration. BH4 is formulated as a sterile liquid or solid dosage form at the appropriate concentration desired.

The advantages of a sterile liquid dosage form of BH4 for intravenous administration may include: (1) more predictable kinetics, with the potential for higher serum levels; (2) no requirement of a functional gastrointestinal tract; (3) no requirement for patient participation; and (4) absence of a noncompliance concern. Intravenous formulations of BH4 may be particularly beneficial in managing conditions requiring expedited delivery of fluids and medications throughout the body or to body compartments normally difficult to access via oral or other forms of administration, including but not limited to rabies, meningitis, organ transplantation/preservation, sub-arachnoidal hemorrhages, brain trauma, stroke, coronary artery bypass surgery, cerebrovascular vasospasm, blood transfusion/preservation, pulmonary hypertension, sickle cell disease, pre-eclampsia, and post-chemotherapy vascular disease.

BH4 is highly susceptible to oxidation in aqueous solution and in physiologic aqueous pH solutions (Davis, et al., Eur. J. Biochem. 173, 345-351 (1988); Kirsch, et al., J. Biol. Chem. 278, 24481-24490 (2003)). Most determinations of BH4 stability have been carried out in neutral to mildly alkaline pH 7.4 solutions to mimic the likely stability behavior of BH4 under physiologic plasma pH condition. Although European Patent Application No. 1 757 293 A discloses liquid or syrup formulations, such formulations consist of solid state powder blends or granulations that require reconstitution with water prior to oral ingestion. The present aspect of invention contemplates liquid formulations not limited to powders or granulations for constitution. The invention also contemplates compounded liquid formulations able to remain stable at ambient temperature for a sufficient period of time to allow processing in sterile product fill/finish facilities to be filled into ampoules, bottles or vials as a liquid product or filled into vials to be freeze-dried into lyophilized products.

The liquid and lyophilized formulations for reconstitution can also be delivered via the nasal, ophthalmic and ear canal for therapeutic effects. The formulation of a lyophilized product requires prior dissolution of BH4 in a liquid, preferably aqueous, and the processing of the liquid product in a sterile facility (i.e. compounding, sterile filtration and filling of the sterile-filtered liquid into vials prior to the loading of the filled vials into a lyophilizer for lyophilization). Maintaining the stability of solubilized BH4 during sterile processing and preventing its degradation are key prerequisites to manufacturing lyophilized product that satisfies impurities specification for the fill-finished product. Therefore the composition of the lyophilized product contains appropriate stabilizers that minimize or obviate BH4 degradation during the fill finish process. The formulations described herein would stabilize BH4 solutions during sterile fill/finish manufacturing, a process that takes a minimum of six hours, and also provide commercially stable product.

The formulations include BH4, preferably in concentration in a range of 0.1 mg/mL to 10 mg/mL. Due to the high solubility of BH4, formulations with concentrations up to about 100 mg/mL, for example, can also be prepared. The general relative compositional makeup and methods described herein are applicable for making highly concentrated solutions.

Liquid formulations of BH4 preferably are formulated in pH 1 to 8 buffer solutions, preferably in pH 2 to 7 buffer solutions. The pH buffers chosen are buffer compounds capable of providing substantial buffering capacity at a particular pH desired, as judged by how close the buffer ionization constant or constants are to the desired pH of the liquid formulation. Thus any buffer compounds may be employed as long as one or more of the compound's ionization constants are close to the desired pH of the formulation. Examples of buffers that may be employed in the pH 1-8 range comprise various acids/bases and their respective conjugate acids/bases or salt forms, including but not limited to: hydrochloric acid (pH 1-2), maleic acid (pH 1-3), phosphoric acid (pH 1-3), citric acid (pH 3-6), acetic acid (pH 4.7±1.0), sodium phosphate dibasic (pH 6-8), tromethamine (TRIS, pH 8.3±1.0), and the like.

Intravenous Formulations

Intravenous formulations are stabilized using an anti-oxidant or a combination of 2 or more antioxidants. Combinations of anti-oxidants can be synergistic in obviating instability of the formulation. Sparging with inert gases and or carbon dioxide to remove dissolved oxygen from solution is optional, but is preferred when low concentrations of antioxidants are used, and further preferably when both low concentrations of BH4 and antioxidants are used. Stabilization of BH4 in aqueous solution is influenced by the interactions of the concentration of BH4 with the antioxidant and pH. Thus, for example, high concentrations of BH4 require less antioxidant concentrations than low concentrations of BH4. Furthermore, BH4 is more stable at low pH than at high pH. Therefore desired high pH formulations preferably have higher antioxidant concentrations, more preferably a combination of 2, 3, or more antioxidants, and still further preferably sparging with non-oxidizing gas (e.g., inert gas or carbon dioxide) followed by hermetically or near-hermetically sealing the primary container in an atmosphere of a non-oxidizing gas (e.g., inert gas or carbon dioxide) to further enhance the stability of the drug product.

Example ranges for BH4 liquid formulations are given in Tables 1 and 2. Formulated or compounded solutions are optionally sparged with an inert gas (e.g., argon or nitrogen) or carbon dioxide in the compounding tank and primary containers preferably are sealed in a blanket of inert gas or carbon dioxide to remove oxygen from the container headspace. The formulation can be scaled up to any volume by multiplying the component amounts by an appropriate scale up factor.

TABLE 1

General examples of composition ranges in a low pH (e.g., pH 4.0) formulation

| Components | Amount (mg) | % Weight/ Volume | Function |
|---|---|---|---|
| BH4 | 0.10-100 | 0.01-10.00 | Active substance |
| L-Cysteine | 0.00-50.00 | 0.00-5.00 | Antioxidant |
| Ascorbic Acid | 0.00-500.00 | 0.00-50.00 | Antioxidant |
| Sodium Metabisulfite | 0.00-300.00 | 0.00-30.00 | Antioxidant |
| Citric Acid | 0.26-19.87 | 0.03-1.99 | Buffering agent |
| Sodium Citrate, Dihydrate | 2.57-192.75 | 0.26-19.27 | Buffering agent |
| Water for Injection qs | 1.00 mL | 1.00 mL | Diluent |

TABLE 2

General examples of composition ranges of a neutral pH (e.g., pH 7.0) formulation

| Components | Amount (mg) | % Weight/ Volume | Function |
|---|---|---|---|
| BH4 | 0.10-100 | 0.01-10.00 | Active substance |
| L-Cysteine | 0.00-50.00 | 0.00-5.00 | Antioxidant |
| Ascorbic Acid | 0.00-500.00 | 0.00-50.00 | Antioxidant |
| Sodium Metabisulfite | 0.00-300.00 | 0.00-30.00 | Antioxidant |
| Sodium Monobasic Phosphate, Monohydrate | 0.50-11.02 | 0.05-1.02 | Buffering agent |
| Sodium Dibasic Phosphate | 0.44-17.80 | 0.04-1.78 | Buffering agent |
| Water for Injection qs | 1.00 mL | 1.00 mL | Diluent |

The antioxidants employed for liquid formulations preferably are selected from one or more of thiol-based (e.g., L-cysteine), ascorbic acid and sulfite-based (e.g. sodium metabisulfite) compounds. Solutions preferably are sparged with inert gases or carbon dioxide to expel oxygen from the BH4 solutions and then hermetically sealed in ampoules or hermetically capped vials and bottles using metallic beverage beer-type caps in a blanket of inert gases (e.g., argon, nitrogen) or non-inert gas such as carbon dioxide to keep the sparged gases in the container head spaces from escaping. Oral liquid formulations preferably additionally contain sweeteners and flavorants improve the palatability of the formulations.

In one embodiment, as a liquid dosage form, BH4 is stabilized by anti-oxidants and/or by sparging with non-oxidizing, preferably sterilized, gases, such as inert gasses (e.g., nitrogen, argon, helium, etc.) and/or a non-inert gas such as carbon dioxide to remove molecular oxygen from the formulation. The product is preferably filled under a blanket of inert gasses to minimize or prevent molecular oxygen from redissolving in the formulation. The liquid is filled into a container (e.g., vials, ampoules, etc.) and hermetically sealed to prevent oxygen from entering the container. In another embodiment, as a sterile solid dosage form for parenteral administration, a solution of BH4 is lyophilized and reconstituted in the clinic prior to administration. In yet another embodiment, sterile powder drug substance of BH4 is directly packaged into sterile containers (e.g., vials, bags, bottles or ampoules) in a sterile dry powder fill facility. Thus, another aspect of the invention is a dry powder formulation of tetrahydrobiopterin (BH4) or a pharmaceutically acceptable salt thereof for constitution into an aqueous solution, including a dry powder mixture of BH4 or pharmaceutically acceptable salt thereof, an antioxidant, and a pH buffer.

Oral Liquid Formulation Compositions

Oral liquid formulations comprise in addition to the components employed in the general liquid and intravenous formulations, sweeteners and flavoring agents. Sweeteners and flavors are added in quantities sufficient to yield acceptable sweetness and flavor. Oral liquid formulations contain one or more stabilizers. Optionally, they contain antimicrobial preservatives. They are preferentially buffered at low pH e.g., pH 1-4 and the buffering agents are selected to match the flavoring agent thus enhancing the organoleptic properties of the oral liquid formulation. Examples of preferred buffers (acid and conjugate bases) are: citric acid, tartaric acid, malic acid in combination with their conjugate bases or salt forms.

Examples of sweeteners include sugars (e.g., sucrose, glucose, sorbitol, mannitol, fructose, etc.), intense non-sugar sweeteners (e.g., aspartame, acesulfame K, cyclamate, saccharin, sucralose, glycyrrhizin, alitame, neotame, neohesperidine DC, thaumatin, monellin, and the like).

In a further embodiment, for nasal, ophthalmic and otic administrations, BH4 is formulated as discussed for parenteral dosage forms and is optionally a sterile product. These dosage forms can be provided in a kit package presentation with several days of supplies. Each unit within the kit can be comprised of one vial or ampoule and one sprayer (for nasal dosage form) or one dropper (in the case of ophthalmic and otic dosage forms). Once the vial or ampoule is opened, the sprayer or dropper is screwed onto the vial or ampoule and the previous cap is discarded. The dosage form product is used within a prescribed expiration period and discarded and a new vial or ampoule is opened for use. Another embodiment is to fill the solutions in hermetic plastic single-use disposable sterile containers produced by a form-fill-and-seal manufacturing process. These packages are opened and the solutions delivered using the desired route of administration by squeezing out the liquid contained within them. These dosage forms are administered once daily and are given via the nostrils (nasal product), or via the eyes (ophthalmic) or droplets are instilled into the auditory canal (otic product). With respect to medication packaged in form, a fill and seal package, the medication is squeezed out onto the route of administration.

In a further embodiment, BH4 is administered via buccal and transdermal routes using formulated strips, patches or films or as topical products that placed on the site of delivery. Sublingual tablets are placed beneath the tongue. These dosage forms are administered once daily and are either attached to the delivery site membrane (buccal and transdermal route) or placed as a solid or semi-dosage form in the sublingual site. To prevent irritation of the delivery site, a basic compound such as sodium carbonate or bicarbonate is coated and mixed with BH4 to prevent interaction with BH4 that would render it unstable. Alternatively the basic compound is added just before use to raise the pH of BH4, which is quite low. Adding the basic excipient at the time of manufacturing without coating the alkaline particles to prevent interaction with BH4, will lead to instability of BH4. Another embodiment is to coat a core sublingual tablet of BH4 with a coating solution containing a basic or alkaline substance. In the sublingual compartment, the basic compound dissolves first, and interacts with BH4 to raise the pH of the medium.

Primary Container Packaging for BH4 Liquid Formulations

The primary packaging containers for BH4 liquid formulations are preferably impermeable to oxygen, carbon dioxide, nitrogen and inert gases. Following filling of sparged liquid formulations of BH4 into the primary container, preferably under a blanket of nitrogen, the containers are preferably hermetically sealed to keep the sparging gas in the liquid and container headspace and prevent the loss of the sparging gas and ingress of oxygen into the container.

The preferred primary containers are hermetically sealed ampoules as well as bottles and vials sealed hermetically with metallic cap such as those employed in sealing soda and beer beverage bottles. During use, the ampoules are cut opened and used within a few hours, e.g., about 12 hours. Ampoules can be used for intravenous and sterile products for injections. Sterile injectable liquids and lyophilized products can also be packaged in rubber closure-sealed vials which are secured with crimped aluminum cap. The antioxidants in the formulations protect the liquid and lyophilized products from the imperceptibly slow loss of sparged gas or oxygen ingress into the vial for the shelf life of the product.

BH4 liquid formulations filled into bottles or vials for oral, ophthalmic or otic use preferably are hermetically secured with a beverage metallic cap or a rubber stopper secured with crimped aluminum seal. The flutes of the bottles or vials can be grooved to accept a screw cap. When the hermetic seal is removed, it is replaced with a screw cap with or without a dropper. The presence of antioxidants in the formulation can enable the screw-capped formulation to be stable for use for at least two weeks, for example, after the hermetic seal is broken.

I. Synthesis of Tetrahydrobiopterin

A variety of methods are known in the art for synthesis of tetrahydrobiopterins, precursors, derivatives and analogs. U.S. Pat. Nos. 5,698,408; 2,601,215; 3,505,329; 4,540,783; 4,550,109; 4,587,340; 4,595,752; 4,649,197; 4,665,182; 4,701,455; 4,713,454; 4,937,342; 5,037,981; 5,198,547; 5,350,851; 5,401,844; 5,698,408, Canadian application CA 2420374, European application nos. EP 079 574, EP 191 335 and Suntory Japanese patent publications JP 4-082888, JP 59-021685 and JP 9-157270, as well as Sugimoto and Matsuura, Bull. Chem. Soc. Japan, 48(12):3767-3768 (1975), Sugimoto and Matsuura, Bull. Chem. Soc. Japan, 52(1):181-183 (1979), Matsuura et al., Chem. Lett. (Japan), 735-738 (1984), Matsuura et al., Heterocycles, Vol. 23, No. 12, 3115-3120, 1985 and Whiteley et al., Anal Biochem. 137(2):394-6 (1984) (each incorporated herein by reference) each describe methods of making dihydrobiopterins, BH4 and derivatives thereof that may be used as compositions for the present invention.

Int'l Publication No. WO2005049614, U.S. Pat. No. 4,540,783, Japanese Patent No. 59-021685, Schircks et al., Helv. Chim. Acta, 60: 211 (1977), Sugimoto et al., Bull. Chem. Soc. Jp, 52(1):181 (1979), Sugimoto et al., Bull. Chem. Soc. Jp, 48(12):3767 (1975), Visontini et al., Helv. Chim. Acta, 52:1225 (1969), and Matsuura et al., Chem. Lett., p 735 (1984), incorporated herein by reference in their entireties, describe methods of synthesizing BH4.

II. Crystalline Forms Of 6R-tetrahydrobiopterin Hydrochloride Salt (6R)-L-erythro-tetrahydrobiopterin dihydrochloride exists in different crystalline forms, including polymorphic forms and solvates, some of which are more stable than others.

Crystal Polymorph Forms of (6R) L-Tetrahydrobiopterin Dihydrochloride Salt

Polymorph Form B

The crystal polymorph that has been found to be the most stable is referred to herein as "form B," or alternatively as "polymorph B." Results obtained during investigation and development of (6R)-L-erythro-tetrahydrobiopterin dihydrochloride development revealed that there are several known crystalline solids have been prepared, but none have recognized the polymorphism and its effect on the stability of the BH4 crystals.

Polymorph B is a slightly hygroscopic anhydrate with the highest thermodynamic stability above about 20° C. Furthermore, form B can be easily processed and handled due to its thermal stability, possibility for preparation by targeted conditions, its suitable morphology and particle size. Melting point is near 260° C. ($\Delta Hf>140$ J/g), but no clear melting point can be detected due to decomposition prior and during melting. These outstanding properties render polymorph form B especially feasible for pharmaceutical application, which are prepared at elevated temperatures. Polymorph B can be obtained as a fine powder with a particle size that may range from 0.2 μm to 500 μm.

Form B exhibits an X-ray powder diffraction pattern, expressed in d-values (Å) at: 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), 2.44 (w). FIG. 1 is a graph of the characteristic X-ray diffraction pattern exhibited by form B of (6R)-L-erythro-tetrahydrobiopterin dihydrochloride.

As used herein, the following the abbreviations in brackets mean: (vs)=very strong intensity; (s)=strong intensity; (m)=medium intensity; (w)=weak intensity; and (vw)=very weak intensity. A characteristic X-ray powder diffraction pattern is exhibited in FIG. 1.

It has been found that other polymorphs of BH4 have a satisfactory chemical and physical stability for a safe handling during manufacture and formulation as well as providing a high storage stability in its pure form or in formulations. In addition, it has been found that form B, and other polymorphs of BH4 can be prepared in very large quantities (e.g., 100 kilo scale) and stored over an extended period of time.

All crystal forms (polymorphs, hydrates and solvates), inclusive of crystal form B, can be used for the preparation of the most stable polymorph B. Polymorph B may be obtained by phase equilibration of suspensions of amorphous or other forms than polymorph form B, such as polymorph A, in suitable polar and non aqueous solvents. Thus, the pharmaceutical preparations described herein refer to a preparation of polymorph form B of (6R)-L-erythro-tetrahydrobiopterin dihydrochloride.

Other forms of BH4 can be converted for form B by dispersing the other form of BH4 in a solvent at room temperature, stirring the suspension at ambient temperatures for a time sufficient to produce polymorph form B, thereafter isolating crystalline form B and removing the solvent from the isolated form B. Ambient temperatures, as used herein, mean temperatures in a range from 0° C. to 60° C., preferably 15° C. to 40° C. The applied temperature may be changed during treatment and stirring by decreasing the temperature stepwise or continuously. Suitable solvents for the conversion of other forms to form B include but are not limited to, methanol, ethanol, isopropanol, other C3- and C4-alcohols, acetic acid, acetonitrile, tetrahydrofurane, methyl-t-butyl ether, 1,4-dioxane, ethyl acetate, isopropyl acetate, other C3-C6-acetates, methyl ethyl ketone and other methyl-C3-C5 alkyl-ketones. The time to complete phase equilibration may be up to 30 hours and preferably up to 20 hours or less than 20 hours.

Polymorph B may also be obtained by crystallization from solvent mixtures containing up to about 5% water, especially from mixtures of ethanol, acetic acid and water. It has been found that polymorph form B of (6R)-L-erythro-tetrahydrobiopterin dihydrochloride can be prepared by dissolution, optionally at elevated temperatures, preferably of a solid lower energy form than form B or of form B of (6R)-L-erythro-tetrahydrobiopterin dihydrochloride in a solvent mixture comprising ethanol, acetic acid and water, addition of seeds to the solution, cooling the obtained suspension and isolation of the formed crystals. Dissolution may be carried out at room temperature or up to 70° C., preferably up to 50° C. There may be used the final solvent mixture for dissolution or the starting material may be first dissolved in water and the other solvents may than be added both or one after the other solvent. The composition of the solvent mixture may comprise a volume ratio of water:acetic acid:tetrahydrofuran of 1:3:2 to 1:9:4 and preferably 1:5:4. The solution is preferably stirred. Cooling may mean temperatures down to −40° C. to 0° C., preferably down to 10° C. to 30° C. Suitable seeds are polymorph form B from another batch or crystals having a similar or identical morphology. After isolation, the crystalline form B can be washed with a non-solvent such as acetone or tetrahydrofurane and dried in usual manner.

Polymorph B may also be obtained by crystallization from aqueous solutions through the addition of non-solvents such as methanol, ethanol and acetic acid. The crystallization and isolation procedure can be advantageously carried out at room temperature without cooling the solution. This process is therefore very suitable to be carried out at an industrial scale.

In one embodiment of the compositions and methods described herein, a composition including polymorph form B of (6R)-L-erythro-tetrahydrobiopterin dihydrochloride is prepared by dissolution of a solid form other than form B or of form B of (6R)-L-erythro-tetrahydrobiopterin dihydrochloride in water at ambient temperatures, adding a non-solvent in an amount sufficient to form a suspension, optionally stirring the suspension for a certain time, and thereafter isolation of the formed crystals. The composition is further modified into a pharmaceutical composition as described below.

The concentration of (6R)-L-erythro-tetrahydrobiopterin dihydrochloride in the aqueous solution may be from 10 to 80 percent by weight, more preferably from 20 to 60 percent by weight, by reference to the solution. Preferred non-solvents (i.e., solvents useful in preparing suspensions of BH4) are methanol, ethanol and acetic acid. The non-solvent may be added to the aqueous solution. More preferably, the aqueous solution is added to the non-solvent. The stirring time after formation of the suspension may be up to 30 hours and preferably up to 20 hours or less than 20 hours. Isolation by filtration and drying is carried out in known manner as described above.

Polymorph form B is a very stable crystalline form, that can be easily filtered off, dried and ground to particle sizes desired for pharmaceutical formulations. These outstanding properties render polymorph form B especially feasible for pharmaceutical application.

Polymorph Form A

It has been found that another crystal polymorph of (6R)-L-erythro-tetrahydrobiopterin dihydrochloride is a stable preferred form of BH4 for use in a pharmaceutical preparation described herein, which shall be referred to herein as "form A," or "polymorph A." Polymorph A is slightly hygroscopic and adsorbs water to a content of about 3 percent by weight, which is continuously released between 50° C. and 200° C., when heated at a rate of 10° C./minute. The polymorph A is a hygroscopic anhydrate, which is a meta-stable form with respect to form B; however, it is stable over several months at ambient conditions if kept in a tightly sealed container. Form A is especially suitable as intermediate and starting material to produce stable polymorph forms. Polymorph form A can be prepared as a solid powder with desired medium particle size range which is typically ranging from 1 μm to about 500 μm.

Figure 2:
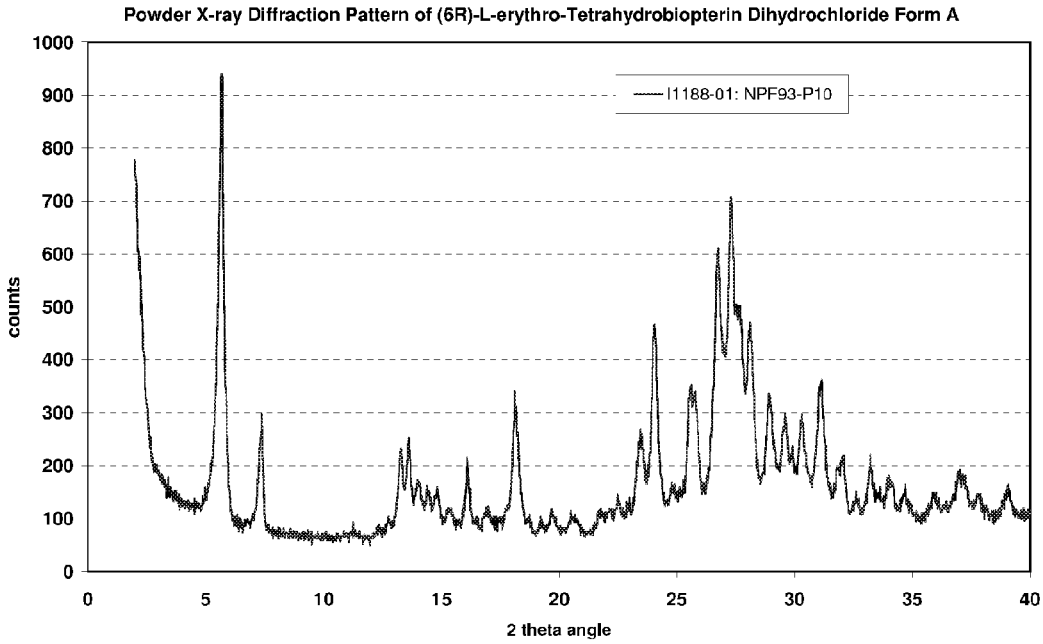
FIG. 2 is a graph of the characteristic X-ray diffraction pattern exhibited by form A of (6R)-L-erythro-tetrahydrobiopterin dihydrochloride.

Polymorph A which exhibits a characteristic X-ray powder diffraction pattern with characteristic peaks expressed in d-values (Å) of: 15.5 (vs.), 12.0 (m), 6.7 (m), 6.5 (m), 6.3 (w), 6.1 (w), 5.96 (w), 5.49 (m), 4.89 (m), 3.79 (m), 3.70 (s), 3.48 (m), 3.45 (m), 3.33 (s), 3.26 (s), 3.22 (m), 3.18 (m), 3.08 (m), 3.02 (w), 2.95 (w), 2.87 (m), 2.79 (w), 2.70 (w). FIG. 2 is a graph of the characteristic X-ray diffraction pattern exhibited by form A of (6R)-L-erythro-tetrahydrobiopterin dihydrochloride.

Polymorph A exhibits a characteristic Raman spectra bands, expressed in wave numbers (cm-1) at: 2934 (w), 2880 (w), 1692 (s), 1683 (m), 1577 (w), 1462 (m), 1360 (w), 1237 (w), 1108 (w), 1005 (vw), 881 (vw), 813 (vw), 717 (m), 687 (m), 673 (m), 659 (m), 550 (w), 530 (w), 492 (m), 371 (m), 258 (w), 207 (w), 101 (s), 87 (s) cm-1.

Polymorph form A may be obtained by freeze-drying or water removal of solutions of (6R)-L-erythro-tetrahydrobiopterin dihydrochloride in water. Polymorph form A of (6R)-L-erythro-tetrahydrobiopterin dihydrochloride can be prepared by dissolving (6R)-L-erythro-tetrahydrobiopterin dihydrochloride at ambient temperatures in water, (1) cooling the solution to low temperatures for solidifying the solution, and removing water under reduced pressure, or (2) removing water from said aqueous solution.

The crystalline form A can be isolated by filtration and then dried to evaporate absorbed water from the product. Drying conditions and methods are known and drying of the isolated product or water removal pursuant to variant (2) described herein may be carried out in applying elevated temperatures, for example up to 80° C., preferably in the range from 30° C. to 80° C., under vacuum or elevated temperatures and vacuum. Prior to isolation of a precipitate obtained in variant (2), the suspension may be stirred for a certain time for phase equilibration. The concentration of (6R)-L-erythro-tetrahydrobiopterin dihydrochloride in the aqueous solution may be from 5 to 40 percent by weight, by reference to the solution.

A fast cooling is preferred to obtain solid solutions as starting material. A reduced pressure is applied until the solvent is completely removed. Freeze drying is a technology well known in the art. The time to complete solvent removal is dependent on the applied vacuum, which may be from 0.01 to 1 mbar, the solvent used and the freezing temperature.

Polymorph form A is stable at room temperature or below room temperature under substantially water free conditions, which is demonstrated with phase equilibration tests of suspensions in tetrahydrofuran or tertiary-butyl methyl ether stirred for five days and 18 hours respectively under nitrogen at room temperature. Filtration and air-drying at room temperature yields unchanged polymorph form A.

Polymorph Form F

It has been found that another crystal polymorph of (6R)-L-erythro-tetrahydrobiopterin dihydrochloride is a stable preferred form of BH4 for use in a pharmaceutical preparation described herein, which shall be referred to herein as "form F," or "polymorph F." Polymorph F is slightly hygroscopic and adsorbs water to a content of about 3 percent by weight, which is continuously released between 50° C. and 200° C., when heated at a rate of 10° C./minute. The polymorph F is a meta-stable form and a hygroscopic anhydrate, which is more stable than form A at ambient lower temperatures and less stable than form B at higher temperatures and form F is especially suitable as intermediate and starting material to produce stable polymorph forms. Polymorph form F can be prepared as a solid powder with desired medium particle size range which is typically ranging from 1 μm to about 500 μm.

Figure 3:
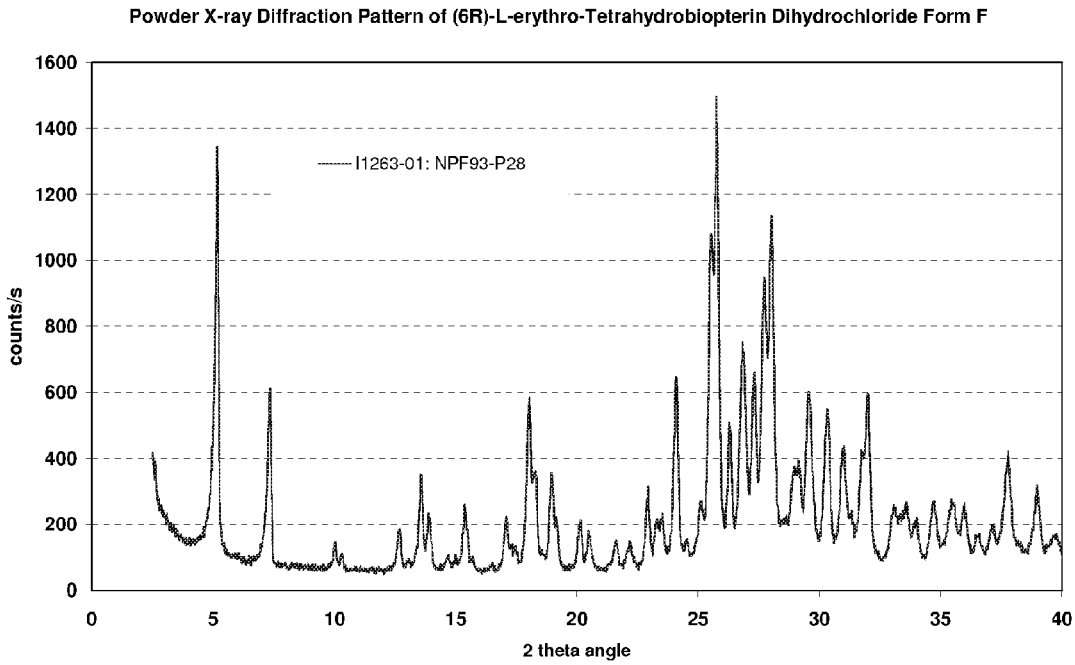
FIG. 3 is a graph of the characteristic X-ray diffraction pattern exhibited by form F of (6R)-L-erythro-tetrahydrobiopterin dihydrochloride.

Polymorph F exhibits a characteristic X-ray powder diffraction pattern with characteristic peaks expressed in d-values (Å) at: 17.1 (vs.), 12.1 (w), 8.6 (w), 7.0 (w), 6.5 (w), 6.4 (w), 5.92 (w), 5.72 (w), 5.11 (w), 4.92 (m), 4.86 (w), 4.68 (m), 4.41 (w), 4.12 (w), 3.88 (w), 3.83 (w), 3.70 (m), 3.64 (w), 3.55 (m), 3.49 (s), 3.46 (vs), 3.39 (s), 3.33 (m), 3.31 (m), 3.27 (m), 3.21 (m), 3.19 (m), 3.09 (m), 3.02 (m), and 296 (m). FIG. 3 is a graph of the characteristic X-ray diffraction pattern exhibited by form F of (6R)-L-erythro-tetrahydrobiopterin dihydrochloride.

Polymorph F may be obtained by phase equilibration of suspensions of polymorph form A in suitable polar and non-aqueous solvents, which scarcely dissolve said lower energy forms, especially alcohols such as methanol, ethanol, propanol and isopropanol. Polymorph form F of (6R)-L-erythro-tetrahydrobiopterin dihydrochloride can also be prepared by dispersing particles of solid form A of (6R)-L-erythro-tetrahydrobiopterin dihydrochloride in a non-aqueous solvent that scarcely dissolves said (6R)-L-erythro-tetrahydrobiopterin dihydrochloride below room temperature, stirring the suspension at said temperatures for a time sufficient to produce polymorph form F, thereafter isolating crystalline form F and removing the solvent from the isolated form F. Removing of solvent and drying may be carried out under air, dry air or a dry protection gas such as nitrogen or noble gases and at or below room temperature, for example down to 0° C. The temperature during phase equilibration is preferably from 5 to 15° C. and most preferably about 10° C.

Polymorph Form J

It has been found that another crystal polymorph of (6R)-L-erythro-tetrahydrobiopterin dihydrochloride is a stable preferred form of BH4 for use in a pharmaceutical preparation described herein, which shall be referred to herein as "form J," or "polymorph J." The polymorph J is slightly hygroscopic and adsorbs water when handled at air humidity. The polymorph J is a meta-stable form and a hygroscopic anhydrate, and it can be transformed back into form E described below, from which it is obtained upon exposure to high relative humidity conditions such as above 75% relative humidity. Form J is especially suitable as intermediate and starting material to produce stable polymorph forms. Polymorph form J can be prepared as a solid powder with desired medium particle size range which is typically ranging from 1 μm to about 500 μm.

Figure 4:
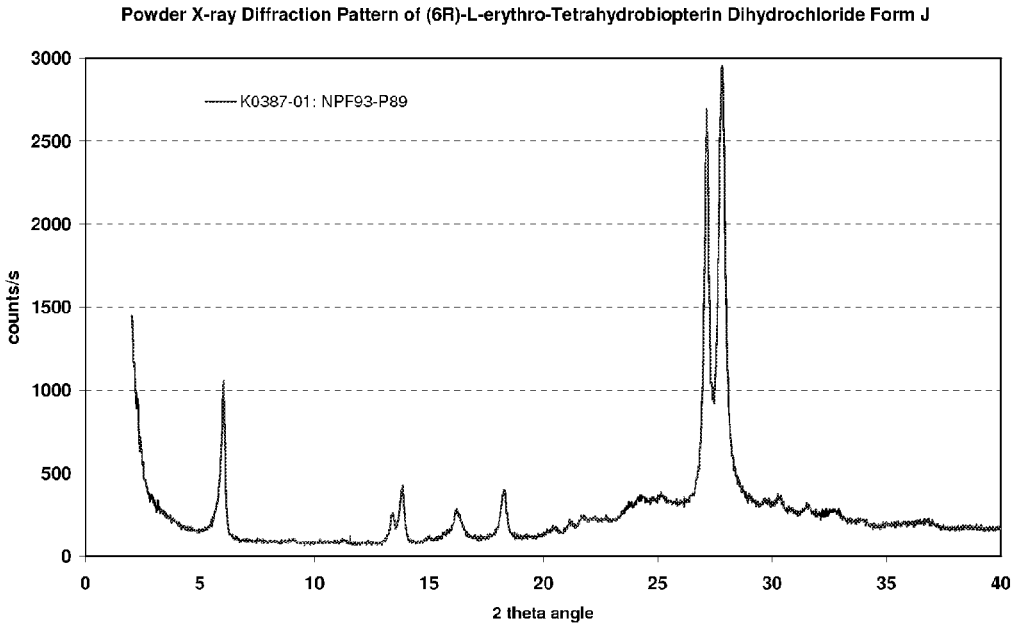
FIG. 4 is a graph of the characteristic X-ray diffraction pattern exhibited by form J of (6R)-L-erythro-tetrahydrobiopterin dihydrochloride.

Form J exhibits a characteristic X-ray powder diffraction pattern with characteristic peaks expressed in d-values (Å) at: 14.6 (m), 6.6 (w), 6.4 (w), 5.47 (w), 4.84 (w), 3.29 (vs), and 3.21 (vs). FIG. 4 is a graph of the characteristic X-ray diffraction pattern exhibited by form J of (6R)-L-erythro-tetrahydrobiopterin dihydrochloride.

Polymorph J may be obtained by dehydration of form E at moderate temperatures under vacuum. In particular, polymorph form J of (6R)-L-erythro-tetrahydrobiopterin dihydrochloride can be prepared by taking form E and removing the water from form E by treating form E in a vacuum drier to obtain form J at moderate temperatures, which may mean a temperature in the range of 25 to 70° C., and most preferably 30 to 50° C.

Polymorph Form K

It has been found that another crystal polymorph of (6R)-L-erythro-tetrahydrobiopterin dihydrochloride is a stable preferred form of BH4 for use in a pharmaceutical preparation described herein, which shall be referred to herein as "form K," or "polymorph K." Polymorph K is slightly hygroscopic and adsorbs water to a content of about 2.0 percent by weight, which is continuously released between 50° C. and 100° C., when heated at a rate of 10° C./minute. The polymorph K is a meta-stable form and a hygroscopic anhydrate, which is less stable than form B at higher temperatures and form K is especially suitable as intermediate and starting material to produce stable polymorph forms, in particular form B. Polymorph form K can be prepared as a solid powder with desired medium particle size range which is typically ranging from 1 μm to about 500 μm.

Figure 5:
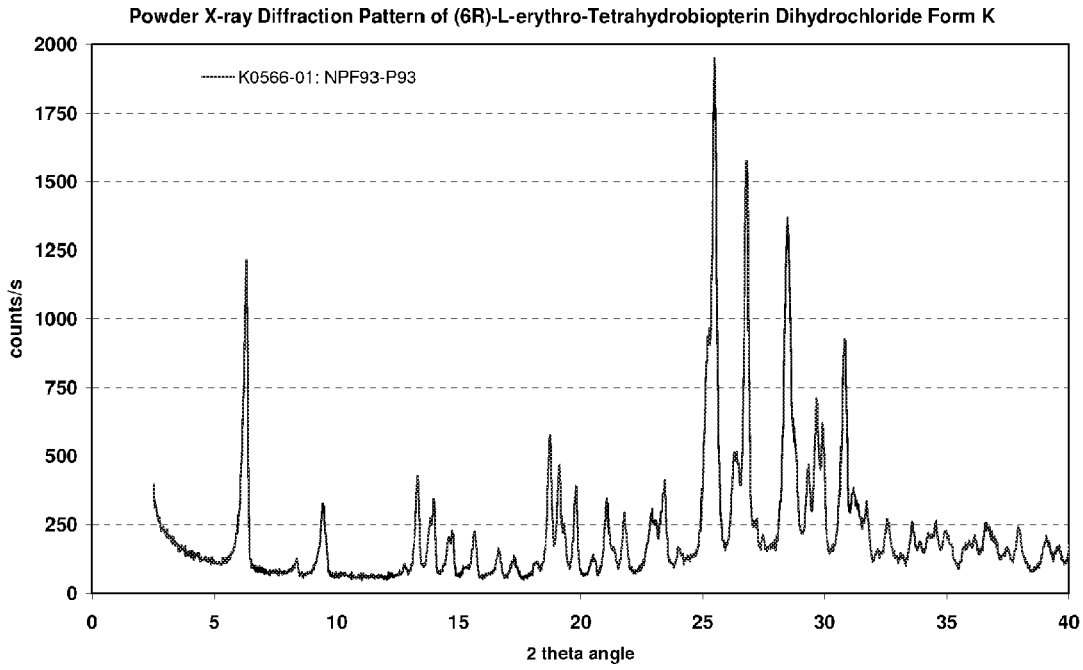
FIG. 5 is a graph of the characteristic X-ray diffraction pattern exhibited by form K of (6R)-L-erythro-tetrahydrobiopterin dihydrochloride.

Form K exhibits a characteristic X-ray powder diffraction pattern with characteristic peaks expressed in d-values (Å) at: 14.0 (s), 9.4 (w), 6.6 (w), 6.4 (w), 6.3 (w), 6.1 (w), 6.0 (w), 5.66 (w), 5.33 (w), 5.13 (vw), 4.73 (m), 4.64 (m), 4.48 (w), 4.32 (vw), 4.22 (w), 4.08 (w), 3.88 (w), 3.79 (w), 3.54 (m), 3.49 (vs), 3.39 (m), 3.33 (vs), 3.13 (s), 3.10 (m), 3.05 (m), 3.01 (m), 2.99 (m), and 2.90 (m). FIG. 5 is a graph of the characteristic X-ray diffraction pattern exhibited by form K of (6R)-L-erythro-tetrahydrobiopterin dihydrochloride.

Polymorph K may be obtained by crystallization from mixtures of polar solvents containing small amounts of water and in the presence of small amounts of ascorbic acid. Solvents for the solvent mixture may be selected from acetic acid and an alcohol such as methanol, ethanol, n- or isopropanol. In particular, polymorph form K of (6R)-L-erythro-tetrahydrobiopterin dihydrochloride can be prepared by dissolving (6R)-L-erythro-tetrahydrobiopterin dihydrochloride in a mixture of acetic acid and an alcohol or tetrahydrofuran containing small amounts of water and a small amount of ascorbic acid at elevated temperatures, lowering temperature below room temperature to crystallize said dihydrochloride, isolating the precipitate and drying the isolated precipitate at elevated temperature optionally under vacuum. Suitable alcohols are for example methanol, ethanol, propanol and isopropanol, whereby ethanol is preferred. The ratio of acetic acid to alcohol or tetrahydrofuran may be from 2:1 to 1:2 and preferably about 1:1. Dissolution of (6R)-L-erythro-tetrahydrobiopterin dihydrochloride can be carried out in presence of a higher water content and more of the anti-solvent mixture can be added to obtain complete precipitation. The amount of water in the final composition may be from 0.5 to 5 percent by weight and the amount of ascorbic acid may be from 0.01 to 0.5 percent by weight, both by reference to the solvent mixture. The temperature for dissolution may be in the range from 30 to 100 and preferably 35 to 70° C. and the drying temperature may be in the range from 30 to 50° C. The precipitate may be washed with an alcohol such as ethanol after isolation, e.g., filtration. The polymorph K can easily be converted in the most stable form B by phase equilibration in e.g., isopropanol and optionally seeding with form B crystals at above room temperature such as temperatures from 30 to 40° C.

Hydrate Forms of (6R) L-Tetrahydrobiopterin Dihydrochloride Salt

As further described below, it has been found that (6R)-L-erythro-tetrahydrobiopterin dihydrochloride exists as a number of crystalline hydrate, which shall be described and defined herein as forms C, D, E, H, and O. These hydrate forms are useful as a stable form of BH4 for the pharmaceutical preparations described herein and in the preparation of compositions including stable crystal polymorphs of BH4.

Hydrate Form C

It has been found that a hydrate crystal form of (6R)-L-erythro-tetrahydrobiopterin dihydrochloride is a stable preferred form of BH4 for use in a pharmaceutical preparation described herein, which shall be referred to herein as "form C," or "hydrate C." The hydrate form C is slightly hygroscopic and has a water content of approximately 5.5 percent by weight, which indicates that form C is a monohydrate. The hydrate C has a melting point near 94° C. ($\Delta H_f$ is about 31 J/g) and hydrate form C is especially suitable as intermediate and starting material to produce stable polymorphic forms. Polymorph form C can be prepared as a solid powder with desired medium particle size range which is typically ranging from 1 μm to about 500 μm.

Figure 6:
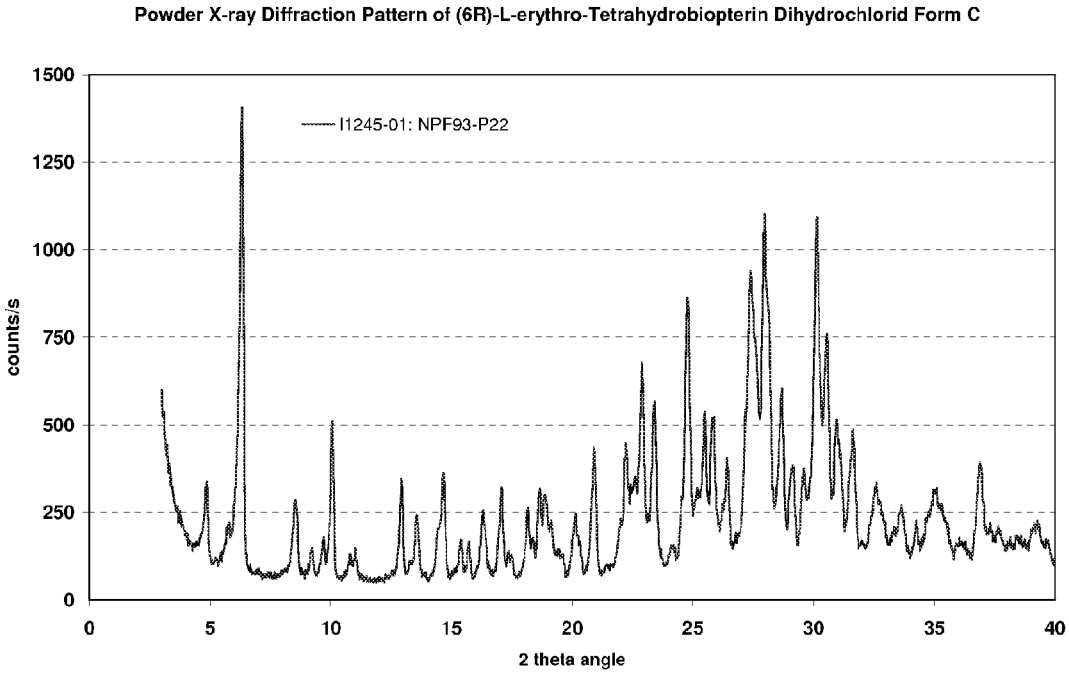
FIG. 6 is a graph of the characteristic X-ray diffraction pattern exhibited by hydrate form C of (6R)-L-erythro-tetrahydrobiopterin dihydrochloride.

Form C exhibits a characteristic X-ray powder diffraction pattern with characteristic peaks expressed in d-values (Å) at: 18.2 (m), 15.4 (w), 13.9 (vs), 10.4 (w), 9.6 (w), 9.1 (w), 8.8 (m), 8.2 (w), 8.0 (w), 6.8 (m), 6.5 (w), 6.05 (m), 5.77 (w), 5.64 (w), 5.44 (w), 5.19 (w), 4.89 (w), 4.76 (w), 4.70 (w), 4.41 (w), 4.25 (m), 4.00 (m), 3.88 (m), 3.80 (m), 3.59 (s), 3.50 (m), 3.44 (m), 3.37 (m), 3.26 (s), 3.19 (vs), 3.17 (s), 3.11 (m), 3.06 (m), 3.02 (m), 2.97 (vs), 2.93 (m), 2.89 (m), 2.83 (m), and 2.43 (m). FIG. 6 is a graph of the characteristic X-ray diffraction pattern exhibited by hydrate form C of (6R)-L-erythro-tetrahydrobiopterin dihydrochloride.

Hydrate form C may be obtained by phase equilibration at ambient temperatures of a polymorph form such as polymorph B suspension in a non-solvent, which contains water in an amount of preferably about 5 percent by weight, by reference to the solvent. Hydrate form C of (6R)-L-erythro-tetrahydrobiopterin dihydrochloride cab be prepared by suspending (6R)-L-erythro-tetrahydrobiopterin dihydrochloride in a non-solvent such as, heptane, C1-C4-alcohols such as methanol, ethanol, 1- or 2-propanol, acetates, such as ethyl acetate, acetonitrile, acetic acid or ethers such as terahydrofuran, dioxane, tertiary-butyl methyl ether, or binary or ternary mixtures of such non-solvents, to which sufficient water is added to form a monohydrate, and stirring the suspension at or below ambient temperatures (e.g., 0 to 30° C.) for a time sufficient to form a monohydrate. Sufficient water may mean from 1 to 10 and preferably from 3 to 8 percent by weight of water, by reference to the amount of solvent. The solids may be filtered off and dried in air at about room temperature. The solid can absorb some water and therefore possess a higher water content than the theoretical value of 5.5 percent by weight. Hydrate form C is unstable with respect to forms D and B, and easily converted to polymorph form B at temperatures of about 40° C. in air and lower relative humidity. Form C can be transformed into the more stable hydrate D by suspension equilibration at room temperature.

Hydrate Form D

It has been found that another hydrate crystal form of (6R)-L-erythro-tetrahydrobiopterin dihydrochloride is a stable preferred form of BH4 for use in a pharmaceutical preparation described herein, which shall be referred to herein as "form D," or "hydrate D." The hydrate form D is slightly hygroscopic and may have a water content of approximately 5.0 to 7.0 percent by weight, which suggests that form D is a monohydrate. The hydrate D has a melting point near 153° C. ($\Delta H_f$ is about 111 J/g) and is of much higher stability than form C and is even stable when exposed to air humidity at ambient temperature. Hydrate form D can therefore either be used to prepare formulations or as intermediate and starting material to produce stable polymorph forms. Polymorph form D can be prepared as a solid powder with desired medium particle size range which is typically ranging from 1 μm to about 500 μm.

Figure 7:
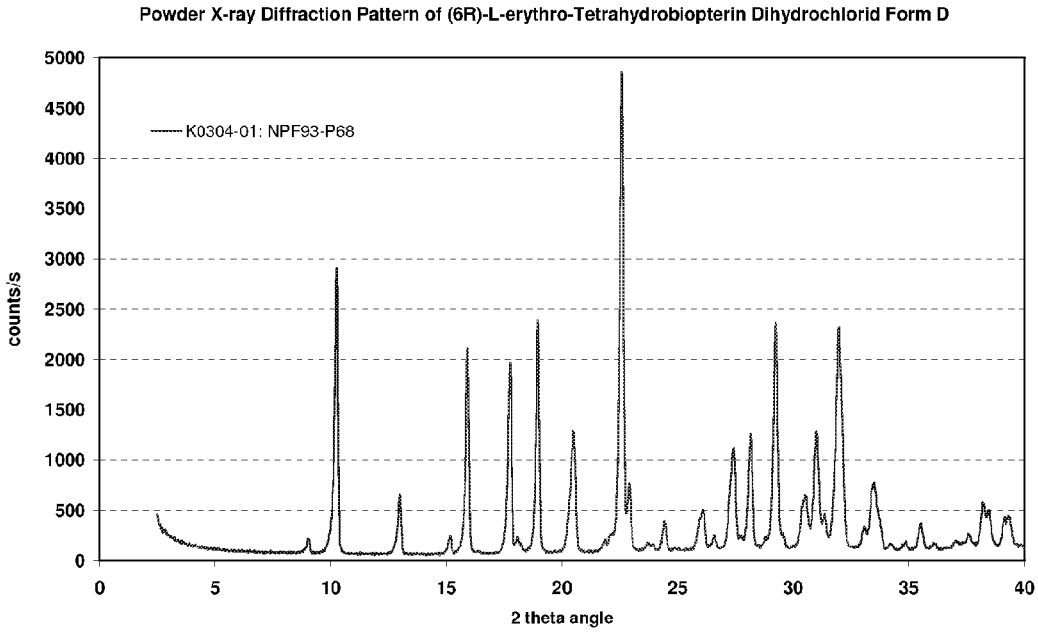
FIG. 7 is a graph of the characteristic X-ray diffraction pattern exhibited by hydrate form D of (6R)-L-erythro-tetrahydrobiopterin dihydrochloride.

Form D exhibits a characteristic X-ray powder diffraction pattern with characteristic peaks expressed in d-values (Å) at: 8.6 (s), 6.8 (w), 5.56 (m), 4.99 (m), 4.67 (s), 4.32 (m), 3.93 (vs), 3.88 (w), 3.64 (w), 3.41 (w), 3.25 (w), 3.17 (m), 3.05 (s), 2.94 (w), 2.92 (w), 2.88 (m), 2.85 (w), 2.80 (w), 2.79 (m), 2.68 (w), 2.65 (w), 2.52 (vw), 2.35 (w), 2.34 (w), 2.30 (w), and 2.29 (w). FIG. 7 is a graph of the characteristic X-ray diffraction pattern exhibited by hydrate form D of (6R)-L-erythro-tetrahydrobiopterin dihydrochloride.

Hydrate form D may be obtained by adding at about room temperature concentrated aqueous solutions of (6R)-L-erythro-tetrahydrobiopterin dihydrochloride to an excess of a non-solvent such as hexane, heptane, dichloromethane, 1- or 2-propanol, acetone, ethyl acetate, acetonitrile, acetic acid or ethers such as terahydrofuran, dioxane, tertiary-butyl methyl ether, or mixtures of such non-solvents, and stirring the suspension at ambient temperatures. The crystalline solid can be filtered off and then dried under dry nitrogen at ambient temperatures. A preferred non-solvent is isopropanol. The addition of the aqueous solution may carried out drop-wise to avoid a sudden precipitation. Hydrate form D of (6R)-L-erythro-tetrahydrobiopterin dihydrochloride can be prepared by adding at about room temperature a concentrated aqueous solutions of (6R)-L-erythro-tetrahydrobiopterin dihydrochloride to an excess of a non-solvent and stirring the suspension at ambient temperatures. Excess of non-solvent may mean a ratio of aqueous to the non-solvent from 1:10 to 1:1000. Form D contains a small excess of water, related to the monohydrate, and it is believed that it is absorbed water due to the slightly hygroscopic nature of this crystalline hydrate. Hydrate form D is deemed to be the most stable one under the known hydrates at ambient temperatures and a relative humidity of less than 70%. Hydrate form D may be used for formulations prepared under conditions, where this hydrate is stable. Ambient temperature may mean 20 to 30° C.

Hydrate Form E

It has been found that another hydrate crystal form of (6R)-L-erythro-tetrahydrobiopterin dihydrochloride is a stable preferred form of BH4 for use in a pharmaceutical preparation described herein, which shall be referred to herein as "form E," or "hydrate E." The hydrate form E has a water content of approximately 10 to 14 percent by weight, which suggests that form E is a dihydrate. The hydrate E is formed at temperatures below room temperature. Hydrate form E is especially suitable as intermediate and starting material to produce stable polymorph forms. It is especially suitable to produce the water-free form J upon drying under nitrogen or optionally under vacuum. Form E is non-hygroscopic and stable under rather high relative humidities, i.e., at relative humidities above about 60% and up to about 85%. Polymorph form E can be prepared as a solid powder with desired medium particle size range which is typically ranging from 1 μm to about 500 μm.

Figure 8:
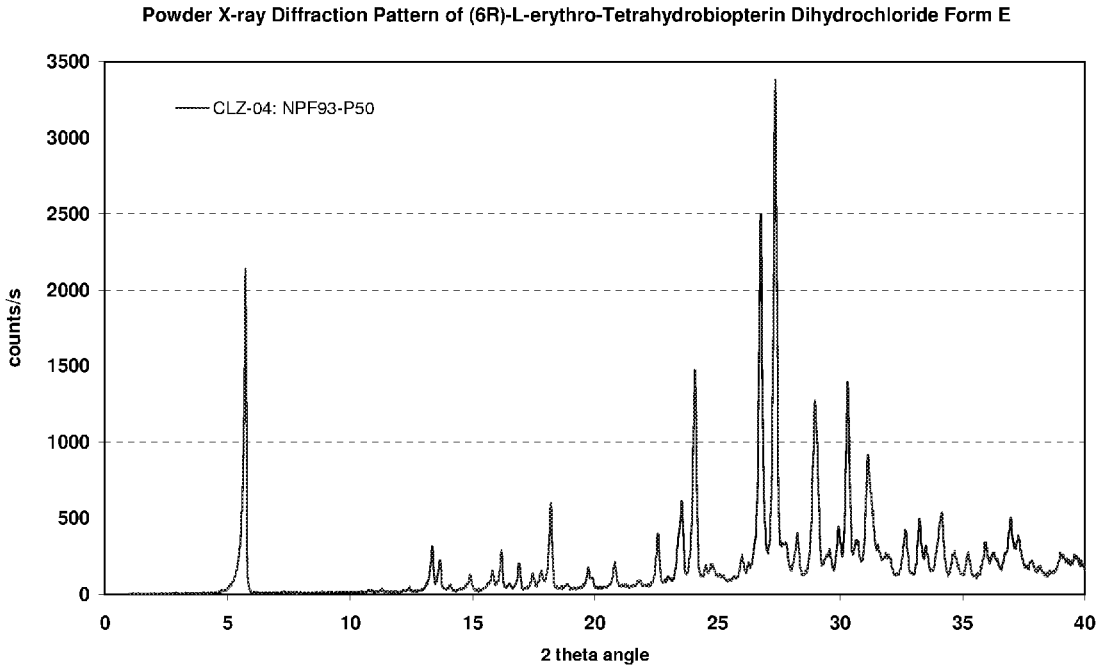
FIG. 8 is a graph of the characteristic X-ray diffraction pattern exhibited by hydrate form E of (6R)-L-erythro-tetrahydrobiopterin dihydrochloride.

Form E exhibits a characteristic X-ray powder diffraction pattern with characteristic peaks expressed in d-values (Å) at: 15.4 (s), 6.6 (w), 6.5 (w), 5.95 (vw), 5.61 (vw), 5.48 (w), 5.24 (w), 4.87 (w), 4.50 (vw), 4.27 (w), 3.94 (w), 3.78 (w), 3.69 (m), 3.60 (w), 3.33 (s), 3.26 (vs), 3.16 (w), 3.08 (m), 2.98 (w), 2.95 (m), 2.91 (w), 2.87 (m), 2.79 (w), 2.74 (w), 2.69 (w), and 2.62 (w). FIG. 8 is a graph of the characteristic X-ray diffraction pattern exhibited by hydrate form E of (6R)-L-erythro-tetrahydrobiopterin dihydrochloride.

Hydrate form E may be obtained by adding concentrated aqueous solutions of (6R)-L-erythro-tetrahydrobiopterin dihydrochloride to an excess of a non-solvent cooled to temperatures from about 10 to −10° C. and preferably between 0 to 10° C. and stirring the suspension at said temperatures. The crystalline solid can be filtered off and then dried under dry nitrogen at ambient temperatures. Non-solvents are for example such as hexane, heptane, dichloromethane, 1- or 2-propanol, acetone, ethyl acetate, acetonitrile, acetic acid or ethers such as terahydrofuran, dioxane, tertiary-butyl methyl ether, or mixtures of such non-solvents. A preferred non-solvent is isopropanol. The addition of the aqueous solution may carried out drop-wise to avoid a sudden precipitation. Hydrate form E of (6R)-L-erythro-tetrahydrobiopterin dihydrochloride can be prepared by adding a concentrated aqueous solutions of (6R)-L-erythro-tetrahydrobiopterin dihydrochloride to an excess of a non-solvent, which is cooled to temperatures from about 10 to −10° C., and stirring the suspension at ambient temperatures. Excess of non-solvent may mean a ratio of aqueous to the non-solvent from 1:10 to 1:1000. A preferred non-solvent is tetrahydrofuran. Another preparation process comprises exposing polymorph form B to an air atmosphere with a relative humidity of 70 to 90%, preferably about 80%. Hydrate form E is deemed to be a dihydrate, whereby some additional water may be absorbed. Polymorph form E can be transformed into polymorph J upon drying under vacuum at moderate temperatures, which may mean between 20° C. and 50° C. at pressures between 0 and 100 mbar. Form E is especially suitable for formulations in semi solid forms because of its stability at high relative humidities.

Hydrate Form H

It has been found that another hydrate crystal form of (6R)-L-erythro-tetrahydrobiopterin dihydrochloride is a stable preferred form of BH4 for use in a pharmaceutical preparation described herein, which shall be referred to herein as "form H," or "hydrate H." The hydrate form H has a water content of approximately 5.0 to 7.0 percent by weight, which suggests that form H is a hygroscopic monohydrate. The hydrate form H is formed at temperatures below room temperature. Hydrate form H is especially suitable as intermediate and starting material to produce stable polymorph forms. Polymorph form H can be prepared as a solid powder with desired medium particle size range which is typically ranging from 1 μm to about 500 μm.

Figure 9:
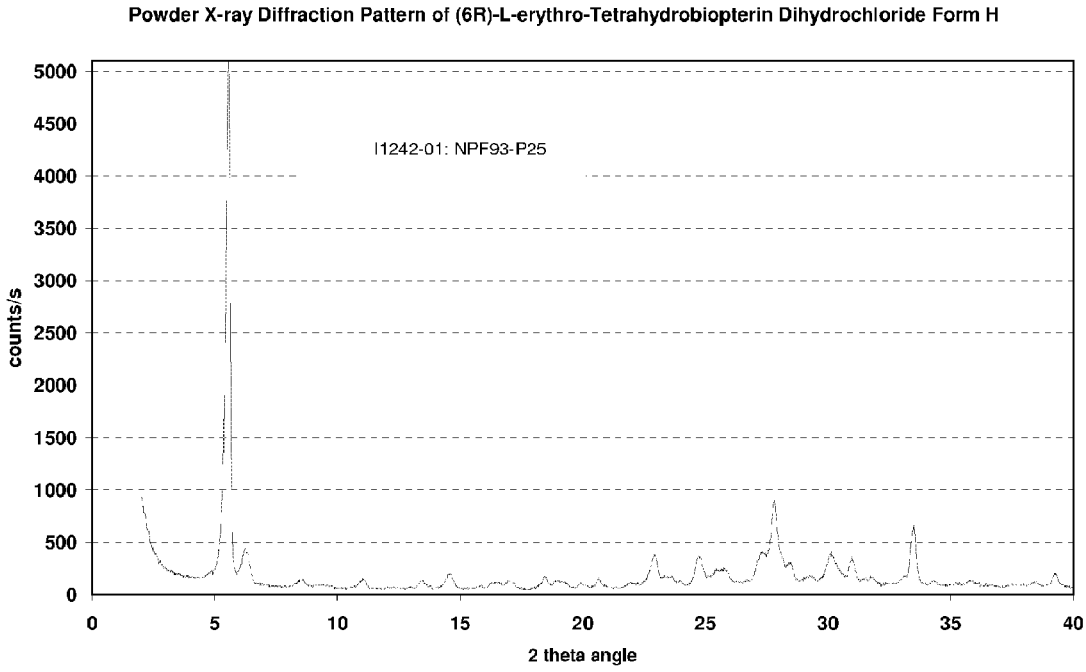
FIG. 9 is a graph of the characteristic X-ray diffraction pattern exhibited by hydrate form H of (6R)-L-erythro-tetrahydrobiopterin dihydrochloride.

Form H exhibits a characteristic X-ray powder diffraction pattern with characteristic peaks expressed in d-values (Å) at: 8.6 15.8 (vs), 10.3 (w), 8.0 (w), 6.6 (w), 6.07 (w), 4.81 (w), 4.30 (w), 3.87 (m), 3.60 (m), 3.27 (m), 3.21 (m), 3.13 (w), 3.05 (w), 2.96 (m), 2.89 (m), 2.82 (w), and 2.67 (m). FIG. 9 is a graph of the characteristic X-ray diffraction pattern exhibited by hydrate form H of (6R)-L-erythro-tetrahydrobiopterin dihydrochloride.

Hydrate form H may be obtained by dissolving at ambient temperatures (6R)-L-erythro-tetrahydrobiopterin dihydrochloride in a mixture of acetic acid and water, adding then a non-solvent to precipitate a crystalline solid, cooling the obtained suspension and stirring the cooled suspension for a certain time. The crystalline solid is filtered off and then dried under vacuum at ambient temperatures. Non-solvents are for example such as hexane, heptane, dichloromethane, 1- or 2-propanol, acetone, ethyl acetate, acetonitril, acetic acid or ethers such as terahydrofuran, dioxane, tertiary-butyl methyl ether, or mixtures of such non-solvents. A preferred non-solvent is tetrahydrofuran. Hydrate form H of (6R)-L-erythro-tetrahydrobiopterin dihydrochloride can be by prepared by dissolving at ambient temperatures (6R)-L-erythro-tetrahydrobiopterin dihydrochloride in a mixture of acetic acid and a less amount than that of acetic acid of water, adding a non-solvent and cooling the obtained suspension to temperatures in the range of −10 to 10° C., and preferably −5 to 5° C., and stirring the suspension at said temperature for a certain time. Certain time may mean 1 to 20 hours. The weight ratio of acetic acid to water may be from 2:1 to 25:1 and preferably 5:1 to 15:1. The weight ratio of acetic acid/water to the non-solvent may be from 1:2 to 1:5. Hydrate form H seems to be a monohydrate with a slight excess of water absorbed due to the hygroscopic nature.

Hydrate Form O

It has been found that another hydrate crystal form of (6R)-L-erythro-tetrahydrobiopterin dihydrochloride is a stable preferred form of BH4 for use in a pharmaceutical preparation described herein, which shall be referred to herein as "form O," or "hydrate O." The hydrate form O is formed at temperatures near room temperature. Hydrate form O is especially suitable as intermediate and starting material to produce stable polymorph forms. Polymorph form O can be prepared as a solid powder with desired medium particle size range which is typically ranging from 1 μm to about 500 μm.

Figure 10:
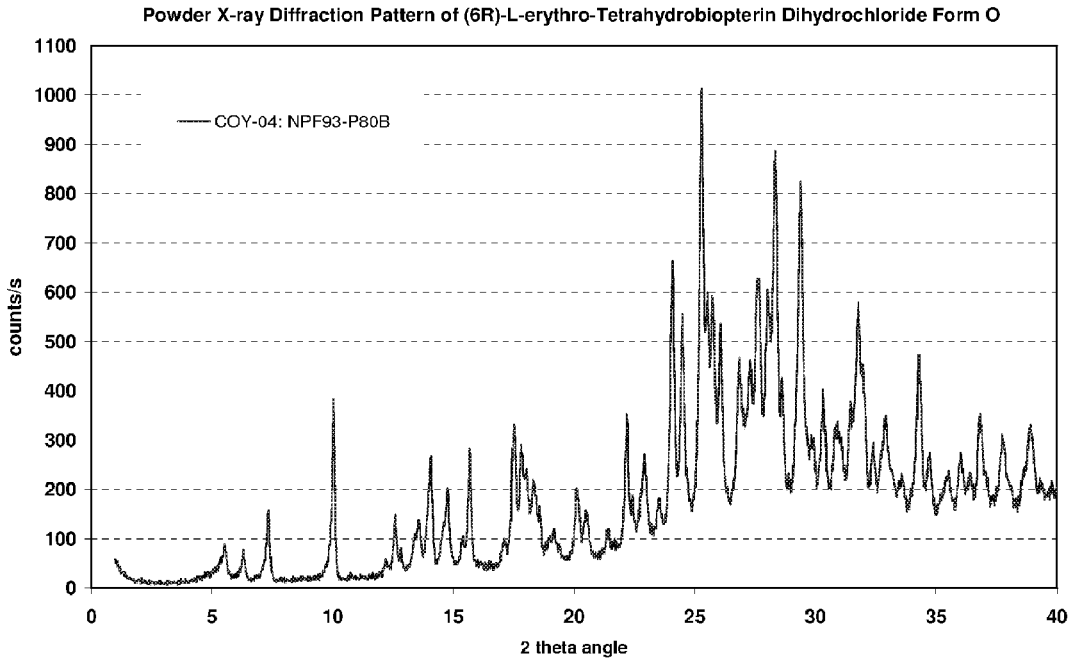
FIG. 10 is a graph of the characteristic X-ray diffraction pattern exhibited by hydrate form O of (6R)-L-erythro-tetrahydrobiopterin dihydrochloride.

Form O exhibits a characteristic X-ray powder diffraction pattern with characteristic peaks expressed in d-values (Å) at: 15.9 (w), 14.0 (w), 12.0 (w), 8.8 (m), 7.0 (w), 6.5 (w), 6.3 (m), 6.00 (w), 5.75 (w), 5.65 (m), 5.06 (m), 4.98 (m), 4.92 (m), 4.84 (w), 4.77 (w), 4.42 (w), 4.33 (w), 4.00 (m), 3.88 (m), 3.78 (w), 3.69 (s), 3.64 (s), 3.52 (vs), 3.49 (s), 3.46 (s), 3.42 (s), 3.32 (m), 3.27 (m), 3.23 (s), 3.18 (s), 3.15 (vs), 3.12 (m), 3.04 (vs), 2.95 (m), 2.81 (s), 2.72 (m), 2.67 (m), and 2.61 (m). FIG. 10 is a graph of the characteristic X-ray diffraction pattern exhibited by hydrate form 0 of (6R)-L-erythro-tetrahydrobiopterin dihydrochloride.

Hydrate form O can be prepared by exposure of polymorphic form F to a nitrogen atmosphere containing water vapor with a resulting relative humidity of about 52% for about 24 hours. The fact that form F, which is a slightly hygroscopic anhydrate, can be used to prepare form O under 52% relative humidity suggests that form O is a hydrate, which is more stable than form F under ambient temperature and humidity conditions.

Solvate Forms of (6R) L-Tetrahydrobiopterin Dihydrochloride Salt

As further described below, it has been found that (6R)-L-erythro-tetrahydrobiopterin dihydrochloride exists as a number of crystalline solvate forms, which shall be described and defined herein as forms G, I, L, M, and N. These solvate forms are useful as a stable form of BH4 for the pharmaceutical preparations described herein and in the preparation of compositions including stable crystal polymorphs of BH4.

Solvate Form G

It has been found that an ethanol solvate crystal form of (6R)-L-erythro-tetrahydrobiopterin dihydrochloride is a stable preferred form of BH4 for use in a pharmaceutical preparation described herein, which shall be referred to herein as "form G," or "hydrate G." The ethanol solvate form G has a ethanol content of approximately 8.0 to 12.5 percent by weight, which suggests that form G is a hygroscopic mono ethanol solvate. The solvate form G is formed at temperatures below room temperature. Form G is especially suitable as intermediate and starting material to produce stable polymorph forms. Polymorph form G can be prepared as a solid powder with a desired medium particle size range which is typically ranging from 1 μm to about 500 μm.

Figure 11:
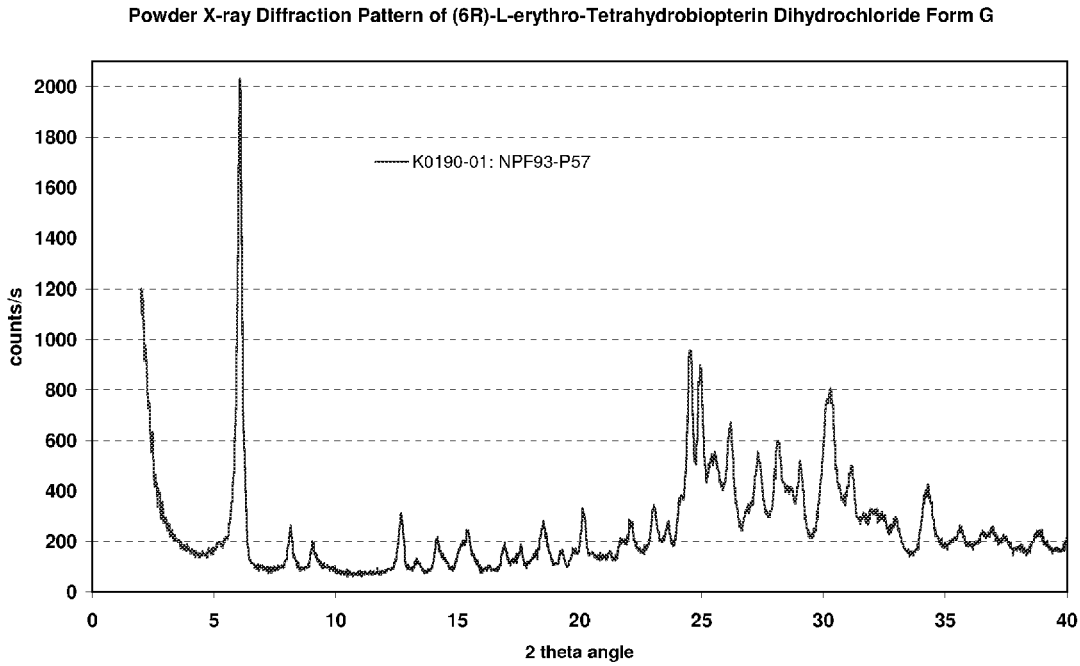
FIG. 11 is a graph of the characteristic X-ray diffraction pattern exhibited by solvate form G of (6R)-L-erythro-tetrahydrobiopterin dihydrochloride.

Form G exhibits a characteristic X-ray powder diffraction pattern with characteristic peaks expressed in d-values (Å) at: 14.5 (vs), 10.9 (w), 9.8 (w), 7.0 (w), 6.3 (w), 5.74 (w), 5.24 (vw), 5.04 (vw), 4.79 (w), 4.41 (w), 4.02 (w), 3.86 (w), 3.77 (w), 3.69 (w), 3.63 (m), 3.57 (m), 3.49 (m), 3.41 (m), 3.26 (m), 3.17 (m), 3.07 (m), 2.97 (m), 2.95 (m), 2.87 (w), and 2.61 (w). FIG. 11 is a graph of the characteristic X-ray diffraction pattern exhibited by solvate form G of (6R)-L-erythro-tetrahydrobiopterin dihydrochloride.

Ethanol solvate form G may be obtained by crystallization of L-erythro-tetrahydrobiopterin dihydrochloride dissolved in water and adding a large excess of ethanol, stirring the obtained suspension at or below ambient temperatures and drying the isolated solid under air or nitrogen at about room temperature. Here, a large excess of ethanol means a resulting mixture of ethanol and water with less than 10% water, preferably about 3 to 6%. Ethanolate form G of (6R)-L-erythro-tetrahydrobiopterin dihydrochloride can be prepared by dissolving at about room temperature to temperatures of 75° C. (6R)-L-erythro-tetrahydrobiopterin dihydrochloride in water or in a mixture of water and ethanol, cooling a heated solution to room temperature and down to 5 to 10° C., adding optionally ethanol to complete precipitation, stirring the obtained suspension at temperatures of 20 to 5° C., filtering off the white, crystalline solid and drying the solid under air or a protection gas such as nitrogen at temperatures about room temperature. The process may be carried out in a first variant in dissolving (6R)-L-erythro-tetrahydrobiopterin dihydrochloride at about room temperature in a lower amount of water and then adding an excess of ethanol and then stirring the obtained suspension for a time sufficient for phase equilibration. In a second variant, (6R)-L-erythro-tetrahydrobiopterin dihydrochloride may be suspended in ethanol, optionally adding a lower amount of water, and heating the suspension and dissolute (6R)-L-erythro-tetrahydrobiopterin dihydrochloride, cooling down the solution to temperatures of about 5 to 15° C., adding additional ethanol to the suspension and then stirring the obtained suspension for a time sufficient for phase equilibration.

Solvate Form I

It has been found that an acetic acid solvate crystal form of (6R)-L-erythro-tetrahydrobiopterin dihydrochloride is a stable preferred form of BH4 for use in a pharmaceutical preparation described herein, which shall be referred to herein as "form I," or "hydrate I." The acetic acid solvate form I has an acetic acid content of approximately 12.7 percent by weight, which suggests that form I is a hygroscopic acetic acid mono solvate. The solvate form I is formed at temperatures below room temperature. Acetic acid solvate form I is especially suitable as intermediate and starting material to produce stable polymorph forms. Polymorph form I can be prepared as a solid powder with desired medium particle size range which is typically ranging from 1 μm to about 500 μm.

Figure 12:
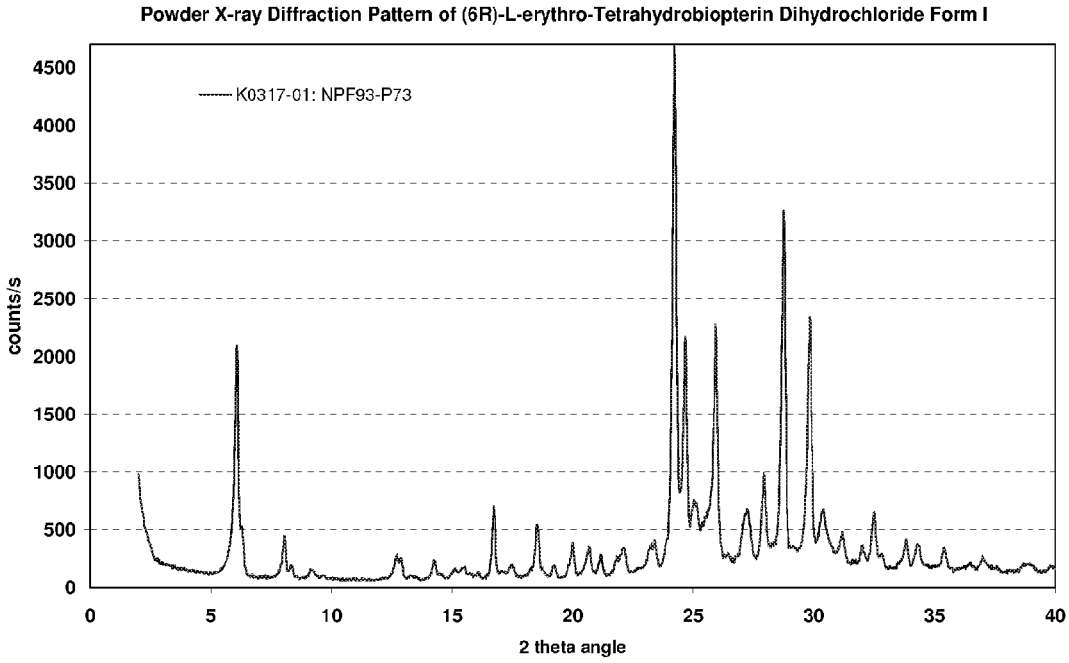
FIG. 12 is a graph of the characteristic X-ray diffraction pattern exhibited by solvate form I of (6R)-L-erythro-tetrahydrobiopterin dihydrochloride.

Form I exhibits a characteristic X-ray powder diffraction pattern with characteristic peaks expressed in d-values (Å) at: 14.5 (m), 14.0 (w), 11.0 (w), 7.0 (vw), 6.9 (vw), 6.2 (vw), 5.30 (w), 4.79 (w), 4.44 (w), 4.29 (w), 4.20 (vw), 4.02 (w), 3.84 (w), 3.80 (w), 3.67 (vs), 3.61 (m), 3.56 (w), 3.44 (m), 3.27 (w), 3.19 (w), 3.11 (s), 3.00 (m), 2.94 (w), 2.87 (w), and 2.80 (w). FIG. 12 is a graph of the characteristic X-ray diffraction pattern exhibited by solvate form I of (6R)-L-erythro-tetrahydrobiopterin dihydrochloride.

Acetic acid solvate form I may be obtained by dissolution of L-erythro-tetrahydrobiopterin dihydrochloride in a mixture of acetic acid and water at elevated temperature, adding further acetic acid to the solution, cooling down to a temperature of about 10° C., then warming up the formed suspension to about 15° C., and then stirring the obtained suspension for a time sufficient for phase equilibration, which may last up to 3 days. The crystalline solid is then filtered off and dried under air or a protection gas such as nitrogen at temperatures about room temperature.

Solvate Form L

It has been found that a mixed ethanol solvate/hydrate crystal form of (6R)-L-erythro-tetrahydrobiopterin dihydrochloride is a stable preferred form of BH4 for use in a pharmaceutical preparation described herein, which shall be referred to herein as "form L," or "hydrate L." Form L may contain 4% but up to 13% ethanol and 0% to about 6% of water. Form L may be transformed into form G when treated in ethanol at temperatures from about 0° C. to 20° C. In addition form L may be transformed into form B when treated in an organic solvent at ambient temperatures (10° C. to 60° C.). Polymorph form L can be prepared as a solid powder with desired medium particle size range which is typically ranging from 1 μm to about 500 μm.

Figure 13:
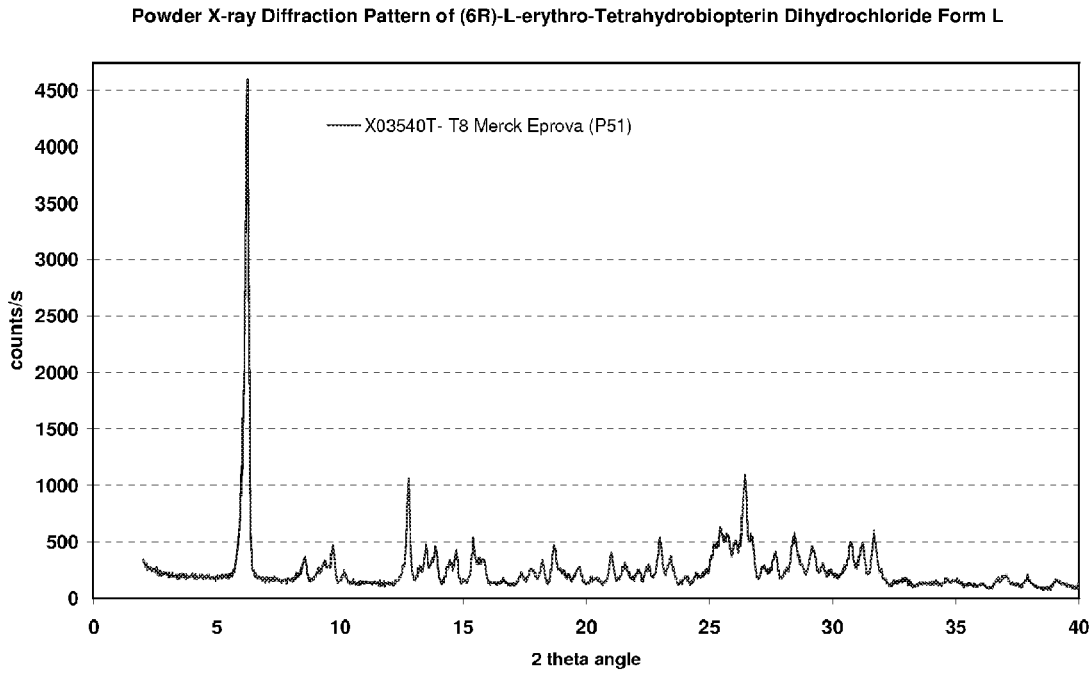
FIG. 13 is a graph of the characteristic X-ray diffraction pattern exhibited by solvate form L of (6R)-L-erythro-tetrahydrobiopterin dihydrochloride.

Form L exhibits a characteristic X-ray powder diffraction pattern with characteristic peaks expressed in d-values (Å) at: 14.1 (vs), 10.4 (w), 9.5 (w), 9.0 (vw), 6.9 (w), 6.5 (w), 6.1 (w), 5.75 (w), 5.61 (w), 5.08 (w), 4.71 (w), 3.86 (w), 3.78 (w), 3.46 (m), 3.36 (m), 3.06 (w), 2.90 (w), and 2.82 (w). FIG. 13 is a graph of the characteristic X-ray diffraction pattern exhibited by solvate form L of (6R)-L-erythro-tetrahydrobiopterin dihydrochloride.

Form L may be obtained by suspending hydrate form E at room temperature in ethanol and stirring the suspension at temperatures from 0 to 10° C., preferably about 5° C., for a time sufficient for phase equilibration, which may be 10 to 20 hours. The crystalline solid is then filtered off and dried preferably under reduced pressure at 30° C. or under nitrogen. Analysis by TG-FTIR suggests that form L may contain variable amounts of ethanol and water, i.e., it can exist as an polymorph (anhydrate), as a mixed ethanol solvate/hydrate, or even as a hydrate.

Solvate Form M

It has been found that an ethanol solvate crystal form of (6R)-L-erythro-tetrahydrobiopterin dihydrochloride is a stable preferred form of BH4 for use in a pharmaceutical preparation described herein, which shall be referred to herein as "form M," or "hydrate M." Form M may contain 4% but up to 13% ethanol and 0% to about 6% of water, which suggests that form M is a slightly hygroscopic ethanol solvate. The solvate form M is formed at room temperature. Form M is especially suitable as intermediate and starting material to produce stable polymorph forms, since form M can be transformed into form G when treated in ethanol at temperatures between about −10° to 15° C., and into form B when treated in organic solvents such as ethanol, C3 and C4 alcohols, or cyclic ethers such as THF and dioxane. Polymorph form M can be prepared as a solid powder with desired medium particle size range which is typically ranging from 1 μm to about 500 μm.

Figure 14:
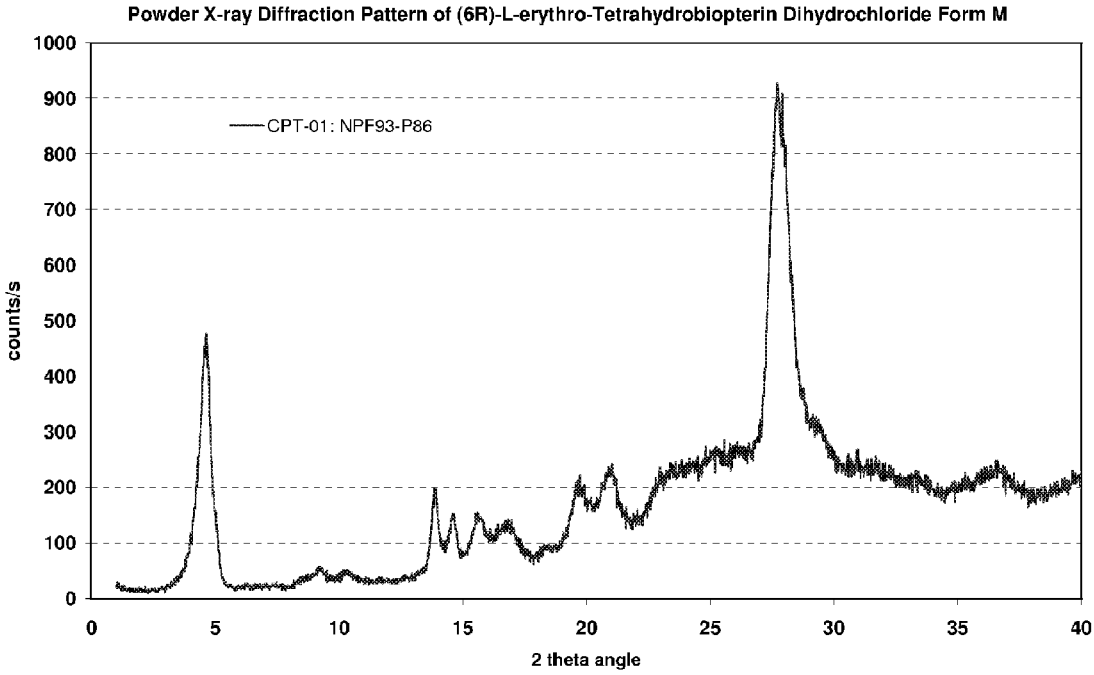
FIG. 14 is a graph of the characteristic X-ray diffraction pattern exhibited by solvate form M of (6R)-L-erythro-tetrahydrobiopterin dihydrochloride.

Form M exhibits a characteristic X-ray powder diffraction pattern with characteristic peaks expressed in d-values (Å) at: 18.9 (s), 6.4 (m), 6.06 (w), 5.66 (w), 5.28 (w), 4.50 (w), 4.23 (w), and 3.22 (vs). FIG. 14 is a graph of the characteristic X-ray diffraction pattern exhibited by solvate form M of (6R)-L-erythro-tetrahydrobiopterin dihydrochloride.

Ethanol solvate form M may be obtained by dissolution of L-erythro-tetrahydrobiopterin dihydrochloride in ethanol and evaporation of the solution under nitrogen at ambient temperature, i.e., between 10° C. and 40° C. Form M may also be obtained by drying of form G under a slight flow of dry nitrogen at a rate of about 20 to 100 ml/min. Depending on the extent of drying under nitrogen, the remaining amount of ethanol may be variable, i.e., from about 3% to 13%.

Solvate Form N

It has been found that another solvate crystal form of (6R)-L-erythro-tetrahydrobiopterin dihydrochloride is a stable preferred form of BH4 for use in a pharmaceutical preparation described herein, which shall be referred to herein as "form N," "hydrate N." Form N may contain in total up to 10% of isopropanol and water, which suggests that form N is a slightly hygroscopic isopropanol solvate. Form N may be obtained through washing of form D with isopropanol and subsequent drying in vacuum at about 30° C. Form N is especially suitable as intermediate and starting material to produce stable polymorph forms. Polymorph form N can be prepared as a solid powder with desired medium particle size range which is typically ranging from 1 μm to about 500 μm.

Figure 15:
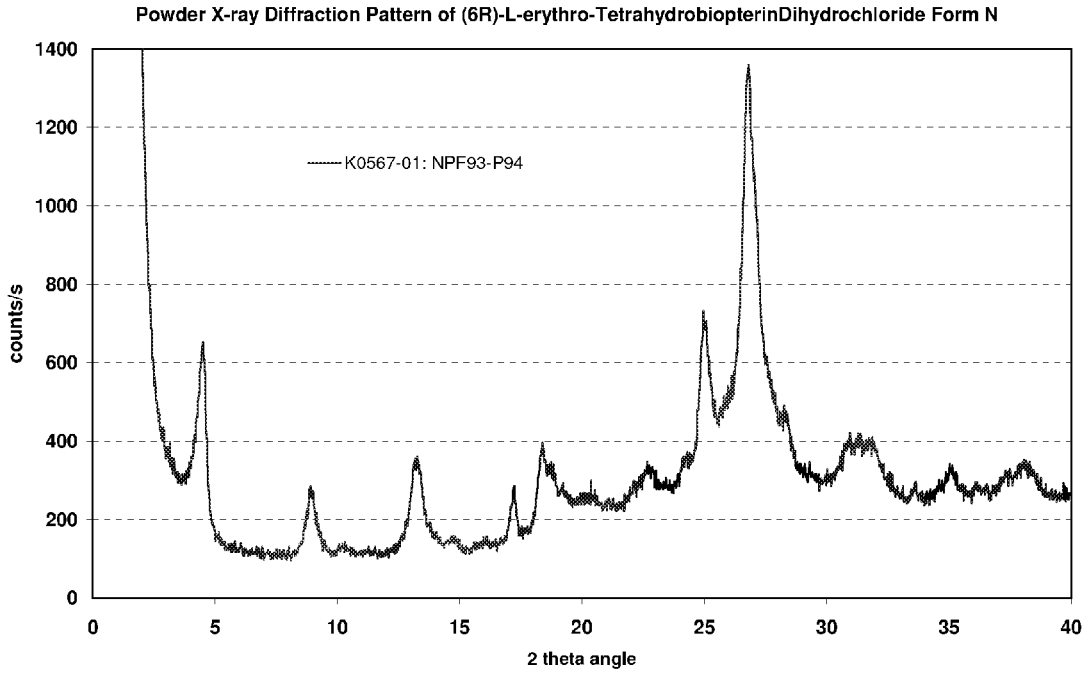
FIG. 15 is a graph of the characteristic X-ray diffraction pattern exhibited by solvate form N of (6R)-L-erythro-tetrahydrobiopterin dihydrochloride.

Form N exhibits a characteristic X-ray powder diffraction pattern with characteristic peaks expressed in d-values (Å) at: 19.5 (m), 9.9 (w), 6.7 (w), 5.15 (w), 4.83 (w), 3.91 (w), 3.56 (m), 3.33 (vs), 3.15 (w), 2.89 (w), 2.81 (w), 2.56 (w), and 2.36 (w). FIG. 15 is a graph of the characteristic X-ray diffraction pattern exhibited by solvate form N of (6R)-L-erythro-tetrahydrobiopterin dihydrochloride.

The isopropanol form N may be obtained by dissolution of L-erythro-tetrahydrobiopterin dihydrochloride in 4.0 ml of a mixture of isopropanol and water (mixing volume ratio for example 4:1). To this solution is slowly added isopropanol (IPA, for example about 4.0 ml) and the resulting suspension is cooled to 0° C. and stirred for several hours (e.g., about 10 to 18 hours) at this temperature. The suspension is filtered and the solid residue washed with isopropanol at room temperature. The obtained crystalline material is then dried at ambient temperature (e.g., about 20 to 30° C.) and reduced pressure (about 2 to 10 mbar) for several hours (e.g., about 5 to 20 hours). TG-FTIR shows a weight loss of 9.0% between 25 to 200° C., which is attributed to both isopropanol and water. This result suggests that form N can exist either in form of an isopropanol solvate, or in form of mixed isopropanol solvate/hydrate, or as an non-solvated form containing a small amount of water.

For the preparation of the polymorph forms, there may be used crystallization techniques well known in the art, such as stirring of a suspension (phase equilibration in), precipitation, re-crystallization, evaporation, solvent like water sorption methods or decomposition of solvates. Diluted, saturated or super-saturated solutions may be used for crystallization, with or without seeding with suitable nucleating agents. Temperatures up to 100° C. may be applied to form solutions. Cooling to initiate crystallization and precipitation down to −100° C. and preferably down to −30° C. may be applied. Meta-stable polymorphs or pseudo-polymorphic forms can be used to prepare solutions or suspensions for the preparation of more stable forms and to achieve higher concentrations in the solutions.

It was surprisingly found that hydrate form D is the most stable form under the hydrates and forms B and D are especially suitable to be used in pharmaceutical formulations. Forms B and D presents some advantages like an aimed manufacture, good handling due to convenient crystal size and morphology, very good stability under production conditions of various types of formulation, storage stability, higher solubility, and high bioavailability. Accordingly, one embodiment of the compositions and methods disclosed herein is pharmaceutical composition including polymorph form B and/or hydrate form D of (6R)-L-erythro-tetrahydrobiopterin dihydrochloride and a pharmaceutically acceptable carrier or diluent.

III. Pharmaceutical Formulations

The formulations described herein are preferably administered as oral formulations. Oral formulations are preferably solid formulations such as capsules, tablets, pills and troches, or liquid formulations such as aqueous suspensions, elixirs and syrups. The various form of BH4 described herein can be directly used as powder (micronized particles), granules, suspensions or solutions, or it may be combined together with other pharmaceutically acceptable ingredients in admixing the components and optionally finely divide them, and then filling capsules, composed for example from hard or soft gelatin, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be, for example, binders such as natural or synthetic polymers, excipients, lubricants, surfactants, sweetening and flavouring agents, coating materials, preservatives, dyes, thickeners, adjuvants, antimicrobial agents, antioxidants and carriers for the various formulation types. The phrase "pharmaceutically or pharmacologically acceptable" refers to molecular entities and compositions that are approved by the U.S. Food and Drug Administration or a corresponding foreign regulatory agency for administration to humans. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also can be incorporated into the compositions.

The initial amount of (6R)-L-erythro-tetrahydrobiopterin used to prepare the formulation may be, for example, in the range of about 30 wt % to about 40 wt % of the formulation, or in the range of about 32 wt % to about 35 wt %, or at about 33 wt %. Specific amounts of BH4 in a formulation contemplated herein include 80 mg, 100 mg, 200 mg, 300 mg, 400 mg, and 500 mg.

Binders assist in maintaining a solid formulation. In some cases, anhydrous binders are used to preserve the anhydrous state of polymorph forms. In some cases, the binder may act as a drying agent. Exemplary binders include anhydrous dibasic calcium phosphate and its monohydrate. Other nonlimiting examples of binders useful in a composition described herein include gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol and esters or -ethers thereof, poly-vinylimidazole, poly-vinylpyrrolidon, and natural polymers like chitosan.

Disintegration agents assist in rapid disintegration of solid formulations by absorbing water and expanding. Exemplary disintegration agents include polyvinylpyrrolidone (PVP, e.g. sold under the name POVIDONE), a cross-linked form of povidone (CPVP, e.g. sold under the name CROSPOVIDONE), a cross-linked form of sodium carboxymethylcellulose (NaCMC, e.g. sold under the name AC-DI-SOL), other modified celluloses, and modified starch. Tablets formulated with CPVP exhibited much more rapid disintegration than tablets formulated with PVP.

Antioxidants may be included and help stabilize the tetrahydrobiopterin product, especially after dissolution. Low pH aqueous solutions of API are more stable than are solutions at neutral or high pH. Antioxidants are included in a formulation described herein to prevent deterioration from oxidation. Antioxidants can generally be classified into 3 groups.

The first group is known as true antioxidants, and inhibit oxidation by reacting with free radicals blocking the chain reaction. Examples include phenolic antioxidants, including butylated hydroxyanisol (BHA), butylated hydroxytoluene (BHT), tert-butyl-hydroquinone (TBHQ), 4-hydroxymethyl-2,6-di-tert-butylphenol (HMBP), and 2,4,5-trihydroxybutyrophenone (THBP); alkygallates, including propyl gallate; gallic acid; nordihydroguaiaretic acid; and tocopherols, including alpha-tocopherol.

The second group, consisting of reducing agents, have lower redox potentials than the drug which they are intended to protect, and are therefore more readily oxidized. Reducing agents may act also by reacting with free radicals. Examples include ascorbic acid, thioglycolic acid (TGA), ascorbyl palmitate, sulfites, including potassium and sodium salts of sulphurous acid (e.g., potassium sulfite, sodium sulfite, sodium metabisulphite, and sodium bisulfite), and thioglycerol.

The third group consists of antioxidant synergists which usually have a modest antioxidant effect themselves but probably enhance the action of antioxidants in the first or second group by reacting with heavy metal ions which catalyze oxidation. Examples of such antioxidant synergists and chelating agents include citric acid, malic acid, editic acid and its salts, lecithin, and tartaric acid.

Exemplary acidic antioxidants include ascorbic acid, fatty acid esters of ascorbic acid such as ascorbyl palmitate and ascorbyl stearate, and salts of ascorbic acid such as sodium, calcium, or potassium ascorbate. Non-acidic antioxidants may also be used in the stable tablet formulations. Nonlimiting examples of non-acidic antioxidants include beta-carotene, alpha-tocopherol. Acidic additives may be added to enhance stability of the tablet formulation, including citric acid or malic acid. Small molecule anti-oxidants include but are not limited to thiols, e.g., cysteine, N-acetyl cysteine, gluthatione, etc., or thiolated polymers (polymer-SH), e.g., polycarbophil-cysteine, polymethacrylic-SH, carboxy methylcellulose-cysteine, etc. or small molecule anti-oxidants such as ascorbic acid, methionine, ascorbyl palmitate, etc. These anti-oxidants confer stability on the dosage form during transit through the GIT, particularly as the pH of the GIT increases with distance from the stomach.

In one embodiment, a combination of at least two reducing agent antioxidants is preferred. In another embodiment, a combination of at least two reducing agent antioxidants together with an acid antioxidant synergist and/or chelating agent is preferred.

Lubricants improve stability, hardness and uniformity of solid formulations. Exemplary lubricants include stearyl fumarate and magnesium stearate. Other nonlimiting examples of lubricants include natural or synthetic oils, fats, waxes, or fatty acid salts such as magnesium stearate.

Optionally the stable formulations of the invention can also comprise other excipients such as mannitol, hydroxyl propyl cellulose, microcrystalline cellulose, or other non-reducing sugars such as sucrose, trehalose, melezitose, planteose, and raffinose. Reducing sugars may react with BH4. Other nonlimiting examples of excipients useful in a composition described herein include phosphates such as dicalcium phosphate.

Surfactants for use in a composition described herein can be anionic, anionic, amphoteric or neutral. Nonlimiting examples of surfactants useful in a composition described herein include lecithin, phospholipids, octyl sulfate, decyl sulfate, dodecyl sulfate, tetradecyl sulfate, hexadecyl sulfate and octadecyl sulfate, Na oleate or Na caprate, 1 -acylamino-ethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Nonlimiting examples of sweetening agents useful in a composition described herein include sucrose, fructose, lactose or aspartame. Nonlimiting examples of flavoring agents for use in a composition described herein include peppermint, oil of wintergreen or fruit flavors such as cherry or orange flavor. Nonlimiting examples of coating materials for use in a composition described herein include gelatin, wax, shellac, sugar or other biological degradable polymers. Nonlimiting examples of preservatives for use in a composition described herein include methyl or propylparabens, sorbic acid, chlorobutanol, phenol and thimerosal.

The BH4 form may also be formulated as effervescent tablet or powder, which disintegrate in an aqueous environment to provide a drinking solution. Slow release formulations may also be prepared in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The BH4 used in a composition described herein is preferably formulated as a dihydrochloride salt, however, it is contemplated that other salt forms of BH4 possess the desired biological activity, and consequently, other salt forms of BH4 can be used. Specifically, BH4 salts with inorganic or organic acids are preferred. Nonlimiting examples of alternative BH4 salts forms includes BH4 salts of acetic acid, citric acid, oxalic acid, tartaric acid, fumaric acid, and mandelic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N' dibenzylethylenediamine, chloroprocaine, choline, diethanolamine, dicyclohexylamine, ethylenediamine, N methylglucamine, and procaine.

Pharmaceutically acceptable acid addition salts include inorganic or organic acid salts. Examples of suitable acid salts include the hydrochlorides, acetates, citrates, salicylates, nitrates, phosphates. Other suitable pharmaceutically acceptable salts are well known to those skilled in the art and include, for example, acetic, citric, oxalic, tartaric, or mandelic acids, hydrochloric acid, hydrobromic acid, sulfuric acid or phosphoric acid; with organic carboxylic, sulfonic, sulfo or phospho acids or N substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4 aminosalicylic acid, 2 phenoxybenzoic acid, 2 acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2 hydroxyethanesulfonic acid, ethane 1,2 disulfonic acid, benzenesulfonic acid, 4 methylbenzenesulfoc acid, naphthalene 2 sulfonic acid, naphthalene 1,5 disulfonic acid, 2 or 3 phosphoglycerate, glucose 6 phosphate, N cyclohexylsulfamic acid (with the formation of cyclamates), or with other acid organic compounds, such as ascorbic acid.

Exemplary stable oral formulations contain one or more of the following additional ingredients that improve the stability or other characteristics of the formulation: binder, disintegration agent, acidic antioxidant, or lubricant or combinations thereof. Exemplary stable tablet formulations include a binder and disintegration agent, optionally with an acidic antioxidant, and optionally further including a lubricant. Exemplary concentrations of binder are between about 1 wt % to about 5 wt %, or between about 1.5 and 3 wt %; an exemplary weight ratio of binder to BH4 is in the range of about 1:10 to about 1:20. Exemplary concentrations of disintegration agent are between about 1 wt % to about 20 wt %; an exemplary weight ratio of disintegration agent to BH4 is in the range of about 1:5 to about 1:10. Exemplary concentrations of antioxidant are between about 1 wt % and about 3 wt %; an exemplary weight ratio of antioxidant to BH4 is in the range of about 1:5 to 1:30. In one example, ascorbic acid is the antioxidant and is used at a ratio to BH4 of less than 1:1, e.g. 1:2 or less, or 1:10 or less. Exemplary concentrations of lubricant in a stable tablet formulation of the present invention are between about 0.1 wt % and about 2 wt %; an exemplary weight ratio of lubricant to BH4 is in the range of about 1:25 to 1:65.

The stable solid formulation may optionally include other therapeutic agents suitable for the condition to be treated, e.g. folates, including folate precursors, folic acids, or folate derivatives; and/or arginine; and/or vitamins, such as vitamin C and/or vitamin B2 (riboflavin) and/or vitamin B12; and/or neurotransmitter precursors such as L-dopa or carbidopa; and/or 5-hydroxytryptophan.

Exemplary folates, including folate precursors, folic acids, or folate derivatives, are disclosed in U.S. Pat. Nos. 6,011,040 and 6,544,994, both of which are incorporated herein by reference, and include folic acid (pteroylmonoglutamate), dihydrofolic acid, tetrahydrofolic acid, 5-methyltetrahydrofolic acid, 5,10-methylenetetrahydrofolic acid, 5,10-methenyltetrahydrofolic acid, 5,10-formiminotetrahydrofolic acid, 5-formyltetrahydrofolic acid (leucovorin), 10-formyltetrahydrofolic acid, 10-methyltetrahydrofolic acid, one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or pharmaceutically compatible salts thereof, or a combination of two or more thereof. Exemplary tetrahydrofolates include 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid, and pharmaceutically acceptable salts thereof. Exemplary salts include sodium, potassium, calcium or ammonium salts.

Exemplary relative weight ratios of BH4 to folates to arginine may be from about 1:10:10 to about 10:1:1.

The stable formulations of the invention may be provided, e.g. as tablets or pills or capsules in HDPE bottles provided with a dessicant capsule or pouch; or in foil-on-foil blister packaging, or in blister packaging comprising see-through polymer film, if commercially desirable.

IV. Treatment Of Bh4-Responsive Diseases

Hyperphenylalaninemia, Neuropsychological or Neuropsychiatric Disorders

The methods of the invention may be used for treatment of conditions associated with elevated phenylalanine levels or decreased tyrosine or tryptophan levels, which may be caused, for example, by reduced phenylalanine hydroxylase, tyrosine hydroxylase, or tryptophan hydroxylase activity. Conditions associated with elevated phenylalanine levels specifically include phenylketonuria, both mild and classic, and hyperphenylalaninemia as described herein, and exemplary patient populations include the patient subgroups described herein as well as any other patient exhibiting phenylalanine levels above normal.

Conditions associated with decreased tyrosine or tryptophan levels include neurotransmitter deficiency, neurological and psychiatric disorders such as Parkinson's, dystonia, spinocerebellar degeneration, pain, fatigue, depression, other affective disorders and schizophrenia. NO overproduction by nNOS has been implicated in strokes, migraine headaches, Alzheimer's disease, and with tolerance to and dependence on morphine. BH4 may be administered for any of these conditions. Other exemplary neuropsychiatric disorders for which BH4 may be administered include Parkinson's disease, Alzheimer's disease, schizophrenia, schizophreniform disorder, schizoaffective disorder, brief psychotic disorder, delusional disorder, shared psychotic disorder, psychotic disorder due to a general medical condition, substance-induced psychotic disorder, other psychotic disorders, tardive dyskinesia, Machado-Joseph disease, spinocerebellar degeneration, cerebellar ataxia, dystonia, chronic fatigue syndrome, acute or chronic depression, chronic stress syndrome, fibromyalgia, migraine, attention deficit hyperactivity disorder, bipolar disease, and autism.

The stable formulations may also be used for treating patients suffering from BH4 deficiency, e.g., due to a defect in the pathway for its synthesis, including but not limited to dopa-responsive dystonia (DRD), sepiapterin reductase (SR) deficiency, or dihydropteridine reductase (DHPR) deficiency.

Suitable subjects for treatment with the stable formulations of the invention include subjects with an elevated plasma Phe concentration in the absence of the therapeutic, e.g. greater than 1800 μM/L, or greater than 1600 μM, greater than 1400 μM, greater than 1200 μM, greater than 1000 μM, greater than 800 μM, or greater than 600 μM, greater than 420 μM, greater than 300 μM, greater than 200 μM, or greater than 180 μM. Mild PKU is generally classified as plasma Phe concentrations of up to 600 μM/L, moderate PKU as plasma Phe concentrations of between 600 μM/L to about 1200 μM/L and classic or severe PKU as plasma Phe concentrations that are greater than 1200 μM/L. Preferably treatment with the stable formulations alone or with protein-restricted diet decreases the plasma phenylalanine concentration of the subject to less than 600 μM, or less than 500 μM, or 360 μM±15 μM or less, or less than 200 μM, or less than 100 μM. Other suitable subjects include subjects diagnosed as having a reduced phenylalanine hydroxylase (PAH) activity, atypical or malignant phenylketonuria associated with BH4 deficiency, hyperphenylalaninemia associated with liver disorder, and hyperphenylalaninemia associated with malaria. Reduced PAH activity may result from a mutation in the PAH enzyme, for example, a mutation in the catalytic domain of PAH or one or more mutations selected from the group consisting of F39L, L485, I65T, R68S, A104D, S110C, D129G, E178G, V190A, P211T, R241C, R261Q, A300S, L308F, A313T, K320N, A373T, V388M E390G, A395P, P407S, and Y414C; or subjects that are pregnant females, females of child-bearing age that are contemplating pregnancy, or infants between 0 and 3 years of age, or 0-2, 0-1.5 or 0-1; or subjects diagnosed as unresponsive within 24 hours to a single-dose BH4 loading test or a multiple dose loading test, such as a 4-dose or 7-day loading test. Exemplary patient populations and exemplary BH4 loading tests are described in Int'l. Publication No. WO 2005/049000, incorporated herein by reference in its entirety.

U.S. Pat. Nos. 4,752,573; 4,758,571; 4,774,244; 4,920,122; 5,753,656; 5,922,713; 5,874,433; 5,945,452; 6,274,581; 6,410,535; 6,441,038; 6,544,994; and U.S. Patent Publications US 20020187958; US 20020106645; US 2002/0076782; US 20030032616 (each incorporated herein by reference) each describe methods of administering BH4 compositions for non-PKU treatments. Each of those patents is incorporated herein by reference as providing a general teaching of methods of administering BH4 compositions known to those of skill in the art, that may be adapted for the treatment as described herein.

While individual needs vary, determination of optimal ranges of effective amounts of each component is within the skill of the art. Typical dosages of the BH4 comprise about 1 to about 20 mg/kg body weight per day, which will usually amount to about 5 (1 mg/kg×5 kg body weight) to 3000 mg/day (30 mg/kg×100 kg body weight). While continuous, daily administration is contemplated, for HPA it may be desirable to cease the BH4 therapy when the symptoms of Phe levels are reduced to below a certain threshold level. Of course, the therapy may be reinitiated in the event that Phe levels rise again. Appropriate dosages may be ascertained through the use of established assays for determining blood levels of Phe in conjunction with relevant dose response data.

In exemplary embodiments, it is contemplated that the methods of the present invention will provide to a patient in need thereof, a daily dose of between about 10 mg/kg to about 20 mg/kg of BH4. Of course, one skilled in the art may adjust this dose up or down depending on the efficacy being achieved by the administration. The daily dose may be administered in a single dose or alternatively may be administered in multiple doses at conveniently spaced intervals. In exemplary embodiments, the daily dose may be 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg, 24 mg/kg, 26 mg/kg, 28 mg/kg, 30 mg/kg, 32 mg/kg, 34 mg/kg, 36 mg/kg, 38 mg/kg, 40 mg/kg, 42 mg/kg, 44 mg/kg, 46 mg/kg, 48 mg/kg, 50 mg/kg, or more mg/kg.

Low Dose Regimens

In a low dose therapeutic method of the invention, low doses, e.g., doses of 0.1 to 5 mg/kg per day are contemplated, including doses of 0.1 to 2 mg/kg, or 0.1 to 3 mg/kg, or 1 mg/kg to 5 mg/kg. Doses of less than 5 mg/kg per day are preferred. According to the invention, such doses are expected to provide improvements with relevant study endpoints, and BH4 derivatives are expected to have improved biological properties relative to natural BH4 at such doses. In particular, the invention contemplates that any of the 1',2'-diacyl-(6R,S)-5,6,7,8-tetrahydro-L-biopterins or lipoidal tetrahydrobiopterins described herein exhibit improved biological properties at low doses.

The invention also specifically contemplates the use of BH4, or a precursor or derivative thereof, for treating BH4-responsive diseases at a dose in the range of 0.1 to 5 mg/kg body weight/day, via any route of administration including but not limited to oral administration, in a once daily dose or multiple (e.g. 2, 3 or 4) divided doses per day, for a duration of at least 1, 2, 3, or 4 weeks or longer, or 1, 2, 3, 4, 5, 6 months or longer. Exemplary doses include less than 5 mg/kg/day, 4.5 mg/kg/day or less, 4 mg/kg/day or less, 3.5 mg/kg/day or less, 3 mg/kg/day or less, 2.5 mg/kg/day or less, 2 mg/kg/day or less, 1.5 mg/kg/day or less, 1 mg/kg/day or less, or 0.5 mg/kg/day or less. Equivalent doses per body surface area are also contemplated.

For the person of average weight/body surface area (e.g. 70 kg), the invention also contemplates a total daily dose of less than 400 mg. Exemplary such total daily doses include 360 mg/day, 350 mg/day, 300 mg/day, 280 mg/day, 210 mg/day, 180 mg/day, 175 mg/day, 150 mg/day, or 140 mg/day. For example, 350 mg/day or 175 mg/day is easily administrable with an oral dosage formulation of 175 mg, once or twice a day. Other exemplary total daily doses include 320 mg/day or less, 160 mg/day or less, or 80 mg/day or less. Such doses are easily administrable with an oral dosage formulation of 80 or 160 mg. Other exemplary total daily doses include 45, 90, 135, 180, 225, 270, 315 or 360 mg/day or less, easily administrable with an oral dosage formulation of 45 or 90 mg. Yet other exemplary total daily doses include 60, 120, 180, 240, 300, or 360 mg/day, easily administrable with an oral dosage formulation of 60 or 120 mg. Other exemplary total daily doses include 70, 140, 210, 280, or 350 mg/day, easily administrable with an oral dosage formulation of 70 or 140 mg. Exemplary total daily doses also include 55, 110, 165, 220, 275 or 330 mg/day, easily administrable with an oral dosage formulation of 55 mg. Other exemplary total daily doses include 65, 130, 195, 260, or 325 mg/day, or 75, 150, 225, 300 or 375 mg/day, e.g. in dosage formulations of 65 mg or 75 mg.

Diseases Associated with Nitric Oxide Synthase Dysfunction

The invention further contemplates that stable formulations of the invention may be used for treatment of subjects suffering from conditions that would benefit from enhancement of nitric oxide synthase activity and patients suffering from vascular diseases, ischemic or inflammatory diseases, or insulin resistance. The treatment may, for example alleviate a deficiency in nitric oxide synthase activity or may, for example provide an increase in nitric oxide synthase activity over normal levels. It has been suggested that a patient suffering from a deficiency in nitric oxide synthase activity would benefit from co-treatment with folates, including folate precursors, folic acids, or folate derivatives.

Nitric oxide is constitutively produced by vascular endothelial cells where it plays a key physiological role in the regulation of blood pressure and vascular tone. It has been suggested that a deficiency in nitric oxide bioactivity is involved in the pathogenesis of vascular dysfunctions, including coronary artery disease, atherosclerosis of any arteries, including coronary, carotid, cerebral, or peripheral vascular arteries, ischemia-reperfusion injury, hypertension, diabetes, diabetic vasculopathy, cardiovascular disease, peripheral vascular disease, or neurodegenerative conditions stemming from ischemia and/or inflammation, such as stroke, and that such pathogenesis includes damaged endothelium, insufficient oxygen flow to organs and tissues, elevated systemic vascular resistance (high blood pressure), vascular smooth muscle proliferation, progression of vascular stenosis (narrowing) and inflammation. Thus, treatment of any of these conditions is contemplated according to methods of the invention.

It has also been suggested that the enhancement of nitric oxide synthase activity also results in reduction of elevated superoxide levels, increased insulin sensitivity, and reduction in vascular dysfunction associated with insulin resistance, as described in U.S. Pat. No. 6,410,535, incorporated herein by reference. Thus, treatment of diabetes (type I or type II), hyperinsulinemia, or insulin resistance is contemplated according to the invention. Diseases or disorders having vascular dysfunction associated with insulin resistance include those caused by insulin resistance or aggravated by insulin resistance, or those for which cure is retarded by insulin resistance, include but are not limited to abnormal vascular compliance, endothelial dysfunction and hypertension, disorders of insulin sensitivity and glucose control, abnormal peripheral perfusion such as intermittent claudication, reduced peripheral perfusion, decreased skin blood flow, defective wound healing and peripheral circulation disorder, hyperlipidemia, arteriosclerosis, coronary vasoconstrictive angina, effort angina, cerebrovascular constrictive lesion, cerebrovascular insufficiency, cerebral vasospasm, coronary arteriorestenosis following percutaneous transluminal coronary angioplasty (PTCA) or coronary artery bypass grafting (CABG), obesity, insulin-independent diabetes, hyperinsulinemia, lipid metabolism abnormality, coronary arteriosclerotic heart diseases, congestive heart failure, pulmonary hypertension with or without congestive heart failure, exercise-associated angina, coronary artery disease and related atherosclerosis; ophthalmic disease such as optic atrophy and diabetic retinal disease; and renal disease such as microalbuminuria in diabetic renal disease, renal failure and decreased glomerular filtration rate.

It is contemplated that when administered to patients with these diseases, BH4 can prevent or treat these diseases by activating the functions of NOS, increasing NO production and suppressing the production of active oxygen species to improve disorders of vascular endothelial cells.

The invention provides a method for treating a subject diagnosed as having vascular disease unrelated to diabetes selected from the group consisting of pulmonary vascular disease, hemolytic anemias, stroke and related ischemic vascular disease (such as stroke, cardiac or coronary disease, arteriosclerosis, or peripheral vascular disease), thrombosis, transplant-related endothelial dysfunction, and cardiac or coronary disease. In one embodiment, pulmonary vascular disease includes but is not limited to pulmonary tension in sickle cell anemia and other hemoglobinopathies, idiopathic pulmonary hypertension, persistent pulmonary hypertension of the newborn (PPHN). In a further embodiment, hemolytic anemias include hereditary hemolytic anemias and acquired hemolytic anemia. Hereditary hemolytic anemias include but are not limited to sickle-cell anemia, thalassemia, hemolytic anemia due to G6PD deficiency, pyruvate kinase deficiency, hereditary elliptocytosis, hereditary spherocytosis, hereditary stomatocytosis, hereditary ovalocytosis, paroxysmal nocturnal hemoglobinuria, and hemoglobin SC disease. Acquired hemolytic anemias include but are not limited to microangiopathic hemolytic anemia, idiopathic autoimmune hemolytic anemia, non-immune hemolytic anemia caused by chemical or physical agents or devices (left ventricular assist devices), mechanical heart valves and bypass devices), and secondary immune hemolytic anemia.

In another embodiment, stroke and related ischemic vascular disease includes but is not limited to vasospasm, such as post-stroke cerebrovascular spasm. Thrombosis includes but is not limited to thrombogenesis, thrombosis, clotting, and coagulation. In a further embodiment, transplant-related endothelial dysfunction includes but is not limited to vascular dysfunction after solid organ transplantation and cyclosporine A induced endothelial dysfunction. In yet another embodiment, cardiac or coronary disease includes but is not limited to congestive heart failure, vascular dysfunction and angina associated with hypercholesterolemia, and vascular dysfunction and angina associated with tobacco smoking.

BH4 can also prevent or treat other disorders associated with the overproduction of or damage related to reactive oxygen species, including but not limited to sepsis.

It is understood that the suitable dose of a composition according to the present invention will depend upon the age, health and weight of the recipient, kind of concurrent treatment, if any, frequency of treatment, and the nature of the effect desired (i.e., the amount of decrease in plasma Phe concentration desired). The frequency of dosing also is dependent on pharmacodynamic effects on Phe levels. If the effect lasts for 24 hours from a single dose. However, the most preferred dosage can be tailored to the individual subject, as is understood and determinable by one of skill in the art, without undue experimentation. This typically involves adjustment of a standard dose, e.g., reduction of the dose if the patient has a low body weight.

The frequency of BH4 dosing will depend on the pharmacokinetic parameters of the agent and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435 1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

V. Combination Therapy

Certain methods of the invention involve the combined use of the stable formulations of the invention and one or more other therapeutic agents.

In such combination therapy, administration of the stable formulations of the invention may be concurrent with or may precede or follow the administration of the second therapeutic agent, e.g. by intervals ranging from minutes to hours, so long as both agents are able to exert their therapeutic effect at overlapping time periods. Thus, the invention contemplates the stable formulations of the invention for use with a second therapeutic agent.

The invention also contemplates use of a second therapeutic agent in preparation of a medicament for administration with the stable tetrahydrobiopterin, precursor, derivative or analog formulations of the invention.

Tetrahydrobiopterin therapy may be combined with dietary protein restriction to effect a therapeutic outcome in patients with various forms of HPA. For example, one could administer to the subject the BH4 composition and a low-phenylalanine medical protein composition in a combined amount effective to produce the desired therapeutic outcome (i.e., a lowering of plasma Phe concentration and/or the ability to tolerate greater amounts of Phe/protein intake without producing a concomitant increase in plasma Phe concentrations). This process may involve administering the BH4 composition and the dietary protein therapeutic composition at the same time. This may be achieved by administering a single composition or pharmacological protein formulation that includes all of the dietary protein requirements and also includes the BH4 within said protein formulation. Alternatively, the dietary protein (supplement or normal protein meal) is taken at about the same time as a pharmacological formulation (tablet, injection or drink) of BH4.

In some embodiments, the protein-restricted diet is one which is supplemented with amino acids, such as tyrosine, valine, isoleucine and leucine. The patient may be co-administered a low-Phe protein supplement, which may include L-tyrosine, L-glutamine, L-carnitine at a concentration of 20 mg/100 g supplement, L-taurine at a concentration of 40 mg/100 g supplement and selenium. It may further comprise the recommended daily doses of minerals, e.g., calcium, phosphorus and magnesium. The supplement further may comprise the recommended daily dose of one or more amino acids selected from the group consisting of L-leucine, L-proline, L-lysine acetate, L-valine, L-isoleucine, L-arginine, L-alanine, glycine, L-asparagine monohydrate, L-tryptophan, L-serine, L-threonine, L-histidine, L-methionine, L-glutamic acid, and L-aspartic acid. In addition, the supplement may be fortified with the recommended daily dosage of vitamins A, D and E. Optionally, the supplement comprises a fat content that provides at least 40% of the energy of the supplement. Such supplements may be provided in the form of a powder supplement or in the form of a protein bar. In certain embodiments, protein-restricted diet comprises a protein supplement and the BH4 is provided in the same composition as the protein supplement.

In other alternatives, the BH4 treatment may precede or follow the dietary protein therapy by intervals ranging from minutes to hours. In embodiments where the protein and the BH4 compositions are administered separately, one would generally ensure that a significant period of time did not expire between the time of each delivery, such that the BH4 will still be able to exert an advantageously effect on the patient. In such instances, it is contemplated that one would administer the BH4 within about 2-6 hours (before or after) of the dietary protein intake, for example, with a delay time of only about 1 hour or less. In certain embodiments, it is contemplated that the BH4 therapy will be a continuous therapy where a daily dose of BH4 is administered to the patient indefinitely. In other situations, e.g., in pregnant women having only the milder forms of PKU and HPA, it may be that the BH4 therapy is only continued for as long as the woman is pregnant and/or breast feeding.

Further, in addition to therapies based solely on the delivery of BH4 and dietary protein regulation, the methods of the present invention also contemplate combination therapy with a third composition that specifically targets one or more of the symptoms of HPA. For example, it is known that the deficit in tyrosine caused by HPA results in a deficiency in neurotransmitters dopamine and serotonin. Thus, in the context of the present invention, it is contemplated that BH4 and dietary protein based methods could be further combined with administration of L-dopa, carbidopa and 5-hydroxytryptophan neurotransmitters to correct the defects that result from decreased amounts of tyrosine in the diet.

In addition, gene therapy with both PAH (Christensen et al., Mol. Gent. And Metabol. 76: 313-318, 2002; Christensen et al., Gene Therapy, 7:1971-1978, 2000) and phenylalanine ammonia-lyase (PAL Liu et al., Arts. Cells. Blood. Subs and Immob. Biotech. 30(4)243-257, 2002) has been contemplated by those of skill in the art. Such gene therapy techniques could be used in combination with the combined BH4/dietary protein restriction based therapies of the invention. In further combination therapies, it is contemplated that phenylase may be provided as an injectable enzyme to destroy lower Phe concentrations in the patient. As the administration of phenylase would not generate tyrosine (unlike administration of PAH), such treatment will still result in tyrosine being an essential amino acid for such patients. Therefore dietary supplementation with tyrosine may be desirable for patients receiving phenylase in combination with the BH4 therapy.

BH4 may be co-administered for neuropsychological or neuropsychiatric disorders according to the method of the invention with one or more other neuropsychiatric active agents, including antidepressants, neurotransmitter precursors such as tryptophan, tyrosine, serotonin, agents which activate noradrenergic systems, such as lofepramine, desipramine, reboxetine, tyrosine, agents which act preferentially on serotonin, combined inhibitors of both noradrenaline and serotonin uptake, such as venlafaxine, duloxetine or milnacipran, or drugs which are combined inhibitors of both dopamine and noradrenaline reuptake such as bupropion.

In a related embodiment, BH4 is administered with other therapeutic agents commonly used to treat diabetes, vascular disease, hyperlipidemia. Agents used to treat diabetes, include but not limited to agents that improve insulin sensitivity such as PPAR gamma ligands (thiazolidinedones, glitazones, troglitazones, rosiglitazone (Avandia), pioglitazone), stimulators of insulin secretion such as sulphonylureas (gliquidone, tolbutamide, glimepride, chlorpropamide, glipizide, glyburide, acetohexamide) and meglitinides (meglitinide, repaglinide, nateglinide) and agents that reduce liver production of glucose such as metformin. Agent used to treat vascular disease, include but not limited to endothelin receptor antagonists commonly used for the treatment of hypertension and other endothelial dysfunction-related disorders, such as bosentan, darusentan, enrasentan, tezosentan, atrasentan, ambrisentan sitaxsentan; smooth muscle relaxants such as PDE5 inhibitors (indirect-acting) and minoxidil (direct-acting); angiotensin converting enzyme (ACE) inhibitors such as captopril, enalapril, lisinopril, fosinopril, perindopril, quinapril, trandolapril, benazepril, ramipril; angiotensin II receptor blockers such as irbesartan, losartan, valsartan, eprosartan, olmesartan, candesartan, telmisartan; beta blockers such as atenolol, metoprolol, nadolol, bisoprolol, pindolol, acebutolol, betaxolol, propranolol; diuretics such as hydrochlorothiazide, furosemide, torsemide, metolazone; calcium channel blockers such as amlodipine, felodipine, nisoldipine, nifedipine, verapamil, diltiazem; alpha receptor blockers doxazosin, terazosin, alfuzosin, tamsulosin; and central alpha agonists such as clonidine. Agents used to treat hyperlipidemia, include but not limited to agents that lower LDL such as statins (atorvastatin, fluvastatin, lovastatin, pravastatin, rosuvastatin calcium, simvastatin) and nicotinic acid, cholesteryl ester transfer protein inhibitors (such as torcetrapib), agents that stimulate PPAR alpha such as fibrates, gemfibrozil, fenofibrate, bezafibrate, ciprofibrate, agents that bind and prevent readsorption of bile acids and reduce cholesterol levels such as bile acid sequestrants, cholestyramine and colestipol, and cholesterol absorption inhibitors.

BH4 may also be administered with a factor or combination of factors that enhances or normalizes the production of the vasodilator nitric oxide (NO) alone or in combination with a therapeutic agent. In one embodiment, such factor(s) enhances the activity or expression the de novo biosynthesis of BH4 and is selected from the group consisting of guanosine triphosphate cyclohydrolase I (GTPCH1), 6-pyruvoyltetrahydropterin synthase (PTPS) and sepiapterin reductase. In a preferred embodiment of the invention, BH4 synthesis is increased by increasing the expression of GTPCH1 expression by the use of any one or more cyclic adenosine monophosphate (cAMP) analogs or agonists including forskolin, 8-bromo cAMP or other agents that function to increase cAMP mediated cell signaling, for example, cytokines and growth factors including interleukin-1, interferon-gamma (IFN-$\gamma$), tumor necrosis factor alpha (TNF-$\alpha$), c-reactive protein, HMG-CoA-reductases (statins like atorvastatin) nerve growth factor (NGF), epidermal growth factor (EGF), hormons including adrenomedullin and estradiol benzoate, and other compounds such as NADPH and NADPH analogs, caffeine, cyclosporine A methyl-xanthines including 3-isobutyl-1-methyl xanthine, theophylline, reserpine, hydrogen peroxide.

One embodiment of invention therefore relates to increasing GTPCH1 levels by inhibiting the degradation of 3'5'-cyclic nucleotides using inhibitors of the eleven phosphodiesterases families (PDE1-11) including PDE1, PDE3, PDE5. The PDE inhibitors of the present invention include Viagra/sildanefil, cialis/tadalafil, vardenafil/levitra, udenafil, 8-Methoxymethyl-IBMX, UK-90234, dexamethasone, hesperetin, hesperedins, Irsogladine, vinpocetine, cilostamide, rolipram, ethyl beta-carboline-3-carboxylate (beta-CCE), tetrahydro-beta-carboline derivatives, 3-O-methylquercetin and the like.

Another embodiment of the invention relates to increasing the levels of BH4 by increasing the levels of BH4-synthesizing enzymes by gene therapy or endothelium-targeted delivery of polynucleotides of the synthetic machinery of BH4. Yet another embodiment of the invention relates to increasing the levels of BH4 by supplementation with BH4-synthesizing enzymes GTPCH1, PTPS, SR, PCD, DHPR and DHFR. It is contemplated that BH4-synthesizing enzymes encompasses all natural and unnatural forms of the enzymes including mutants of the proteins.

Another embodiment of the invention relates to increasing BH4 levels by diverting the substrate 7,8-dihydroneopterin triphosphate towards BH4 synthesizing enzyme PTPS instead of alkaline phosphatase (AP) by inhibiting AP activity. The agents or compounds that inhibit the activity of AP include phosphate analogs, levamisole, and L-Phe. Another embodiment of the invention relates to agents or compounds that inhibit alkaline phosphatase includes the small inhibitory RNA (siRNA), antisense RNA, dsDNA, small molecules, neutralizing antibodies, single chain, chimeric, humanized and antibody fragments to inhibit the synthesis of alkaline phosphatase.

Another embodiment of the invention includes agents or compounds that enhance the activity of catalysts or cofactors needed for the synthesis of enzymes of the de novo synthesis pathway of BH4 synthesis.

Another embodiment of the invention includes agents or compounds that prevent the degradation of the enzymes needed for the synthesis of BH4. Yet another embodiment of the invention includes agents or compounds that prevent the degradation of the catalysts needed for the synthesis of BH4 and its synthetic enzymes including GTPCH1, PTPS and SR.

Another embodiment of the invention relates to increasing the levels of BH4 by increasing the reduction of BH2 via the salvage pathway. In vivo, BH4 becomes oxidized to BH2. BH2 which exist as the quinoid form (qBH2) and as the 7,8-dihydropterin which is reduced to BH4 by DHPR and DHFR respectively. One embodiment of the invention relates to increasing the regeneration or salvage of BH4 from BH2 by modulating the activity and synthesis of the enzymes PCD, DHPR and DHFR using agents or compounds that pathway NADPH, thiols, perchloromercuribenzoate, hydrogen peroxide and the like.

Another embodiment of the invention relates to agents that stabilize BH4 by decreasing the oxidation of BH4 using agents or compounds such as antioxidants including ascorbic acid (vitamin C), alpha tocopherol (vitamin E), tocopherols (e.g vitamin A), selenium, beta-carotenes, carotenoids, flavones, flavonoids, folates, flavones, flavanones, isoflavones, catechins, anthocyanidins, and chalcones.

In a further embodiment, such factor(s) may increase the activity or expression of nitric oxide synthase and thereby enhance the generation of NO.

In yet another embodiment, the invention contemplates factors that inhibit the GTPCH feedback regulatory protein, GFRP. An embodiment of the invention relates to agents or compounds that inhibit the binding of BH4 to the GTPCH1/GFRP complex, thereby preventing the feedback inhibition by BH4. Agents or compounds of this invention include competitive inhibitors such as alternate forms of BH4 with altered affinities for the complex, structural analogs etc. Still another embodiment of the invention includes agents or compounds that enhance the binding of L-phenylalanine to CTPCH1/GFRP inducing the synthesis of BH4. Another embodiment of the invention includes agents or compounds that increase the levels of L-Phe such as precursors of L-Phenylalanine, which serves to inhibit the feedback inhibition of GTPCH1 by GFRP and BH4.

Yet another embodiment of the invention relates to agents or compounds that modulate the activity or the synthesis of GFRP. An embodiment of the invention includes agents or compounds that inhibit the activity of GFRP. Another embodiment of the invention includes the use of siRNA, small molecules, antibodies, antibody fragments and the like to inhibit the synthesis of GFRP.

VI. Biopterin Assays

The concentration of total biopterin and oxidized biopterin in plasma, blood and other tissues are determined based on the method of Fukishima et al (Anal. Biochem. 102:176 (1980). Biopterin has four different forms including two forms of reduced biopterin, R-tetrahydrobiopterin (BH4) and quinonoid R-dihydrobiopterin (q-BH2) and two forms of oxidized biopterin, dihydrobiopterin (BH2) and biopterin (B). Of these four forms, only the reduced forms of biopterin have coenzymatic activity. Reduced biopterin is converted to B by iodylation under acidic conditions, whereas under alkaline conditions, it is converted to pterin. Oxidized biopterin is converted to B by iodylation under acidic and alkaline conditions. By taking advantage of this property, the amount of total biopterin is determined upon iodylation under acidic conditions and that of oxidized biopterin is determined upon iodylation under alkaline conditions, so that the amount of reduced biopterin is calculated from the difference in quantity thereof. When used as a coenzyme, BH4 is converted to q-BH2. The q-BH2 is immediately converted to BH4 by dihydropterine reductase or if not reduced, it is oxidized to BH2 or DHPT. Because it is difficult for biopterin to exist in the form of q-BH2 in vivo, the reduced biopterin may well be displaced as BH4.

Plasma and whole blood samples collected are immediately subjected to oxidation with acidic oxidizing solution (0.6N HCl solution in water containing 0.6% potassium iodide (KI), 0.3% iodine (I2) and 0.6N trichloroacetic acid (TCA)) and alkaline oxidizing solution (0.7N sodium hydroxide (NaOH)). Determination of B is performed by HPLC and radioactivity is measured using a liquid scintillation counter.

Measurement of BH4 using Reverse Phase HPLC (RP) Coupled with Tandem Mass Spectrometry (LC/MS/MS): The combined use of reverse phase high performance liquid chromatography (RP) and tandem mass spectrometry (LC/MS/MS) was shown to be selective for BH4 in human plasma, sensitive for BH4 in the range of 5-1000 ng/mL. The method is associated with about 50% conversion of BH4 due to oxidation during collection and storage. Samples are stable for greater than 3 months in dipotassium salt of ethylenediaminetetraacetic acid ($K_2$EDTA) plasma. Recovery from the pretreatment steps is about 75%. The accuracy and precision of the method was determined to have coefficient of variation (CV) % below 15% (20% at the lower limit of quantitation, LLOQ).

The combined use of HPLC and tandem mass spectrometry was shown to be an improvement over HPLC alone in determining the BH4 test article because of: (1) its increased selectivity for drug-BH4 (whereas HPLC measures total biopterin), (2) broader qualitative range, (3) established conversion ration, (4) extensive characterization and proven utility in human subjects, and (5) novel and useful measurement in different species and matrices.

The improved method comprises the following steps. Samples of blood, plasma, tissue homogenates, or urine are subjected to acidic or alkaline oxidation. With acidic oxidation, (1) the samples are treated with potassium chloride (KCl), hydrochloric acid (HCl) or TCA for an hour; (2) the acid oxidized samples are then subjected to iodometry; (3) the samples are run through an ion exchange column; (4) total biopterin comprising BH4, q-BH2 (which is immediately reduced in vivo to BH4 such that the measured reduced biopterin is based mainly upon BH4), BH2, and B are measured using HPLC and tandem mass spectrometry. With alkaline oxidation, (1) the samples are treated with KI, I2 or NaOH for an hour; (2) the alkaline oxidized samples are then subjected to acidification with HCl or TCA; (3) subjected to iodometry; (4) the samples are run through an ion exchange column; (5) oxidized biopterin comprising BH2 and B are measured; (6) different species are measured using HPLC and tandem mass spectrometry; and (7) the amount of reduced biopterin (BH4+q-BH2) is calculated as the difference between total biopterins less the oxidized form.

Flow charts for biopterin measurement and assay validation summary are provided in FIGS. 16 and 17.

Optimized Assay

An HPLC method using Electrochemical Detection (ECD) and Fluorescence (FL) detection is advantageous as it allows for the measurement of each of the discrete biopterin compounds (BH4, BH2 and B) as well as analogs.

BH4 is a cofactor for the enzyme system nitric oxide synthase (NOS), which produces nitric oxide (NO). The production of NO is important for maintaining vascular homeostasis. When intracellular levels of BH4 are limited, NO production is diminished (due to decreased NOS activity) and leads to the generation of the damaging free radical superoxide ($O_2$—). Excess $O_2$— can lead to endothelial dysfunction and may contribute to the oxidation of BH4 to BH2. A low ratio of BH4 to BH2 may promote endothelial injury, whereas a high BH4 to BH2 ratio may promote endothelial health. Therefore, characterizing the BH4 to BH2 ratio may serve as a predictor of endothelial health.

The concentrations of different biopterins (BH4, BH2 and B) or analogs are determined by initially using reverse phase HPLC for separation, followed by ECD and FL detection.

BH4, which is a redox-sensitive, non-fluorescent molecule, is measured using ECD. BH4 (and analogs thereof) are measured using ECD in which BH4 (or analog) is oxidized by electrode 1 to a quinonoid dihydrobiopterin form (e.g., qBH2), a short-lived dihydrobiopterin intermediate, which is then reduced back to BH4 (or analog) at electrode 2. The detector then uses the current generated by this reduction reaction to determine the concentration of BH4 or analog thereof (endogenous qBH2 is negligible).

BH2, B, and analogs thereof can be measured in the same injection by fluorescence detection. Post-ECD oxidation of BH2 or an analog thereof using a conditioning guard cell at the optimum potential oxidizes BH2 or an analog thereof to B or the corresponding biopterin analog. This is desirable because BH2 is not fluorescently active or easily measured and must be converted to B, which is easily measured using fluorescence. Endogenous BH2, once converted to B, and endogenous B are distinguished from one another by two separate fluorescent peaks, due to the different retention times on the HPLC column for each molecule.

In total the methods can be used to measure the species BH4, BH2, and B, and analogs thereof The biopterins preferably are measured using a 2% MeOH-containing mobile phase, as described herein. Biopterin analogs, such as valine biopterin derivatives, may be better suited to higher methanol contents in the mobile phase, e.g. a 10% MeOH-containing mobile phase.

Thus, a method for detecting biopterins in a mixture of biopterin species can include (a) separating biopterin species in the mixture by reverse phase HPLC; and in the case of BH4 and analogs thereof, (b1) performing electrochemical detection by oxidizing the BH4 and analogs thereof present by a first electrode to quinonoid dihydrobiopterin forms, followed by reducing the quinonoid forms back to BH4 and analogs thereof present at a second electrode, and measuring current generated by the reduction reaction to determine the concentration of species; and/or (b2) in the case of BH2, analogs thereof, biopterin, or analogs thereof, measuring such species by fluorescence detection following post-column oxidation of BH2 species to biopterin. Preferably, the mobile phase is one disclosed herein.

In one embodiment, the preferred mobile phase includes sodium acetate, citric acid, EDTA, and 1,4-dithioerythritol (DTE) with methanol. Preferred concentrations are 50 mM sodium acetate, 5 mM citric acid, 48 μM EDTA, and 160 μM DTE with 2% methanol.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Concentration Time Curve for Biopterin in Plasma After a Single Oral Dose in the Rat The purpose of this study was to assess the pharmacokinetics of BH4 after a single oral administration in rats. Single doses of BH4 (10 and 100 mg/kg) were administered orally to male Sprague Dawley rats (6 weeks old) under fasting conditions.

Results

Figure 18:
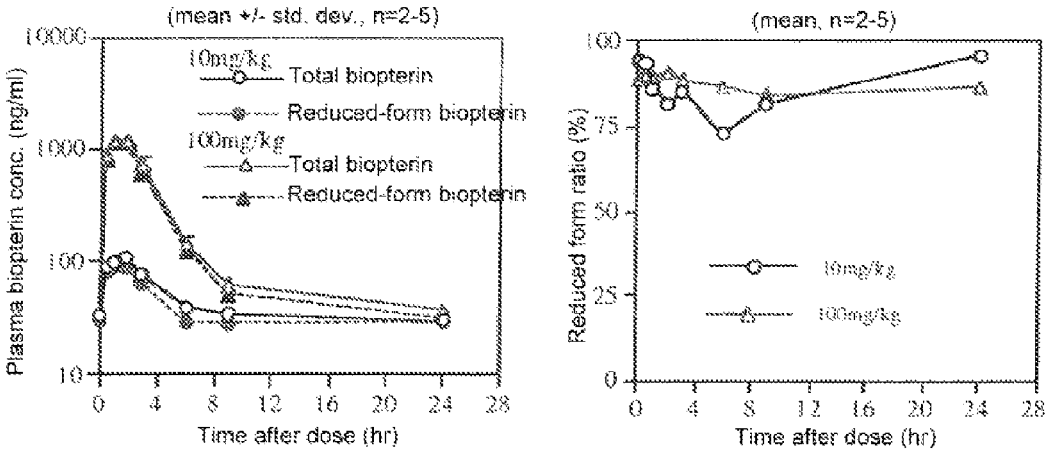
FIG. 18 is a table showing pharmacokinetic parameters of total biopterins in plasma after a single oral administration of sapropterin (BH4) to rats.

The maximum total biopterin concentrations in plasma 2 hrs and 1 hr post-dosing were 108 ng/ml (i.e., about 3× the endogenous level) and 1227 ng/ml (i.e., about 30× the endogenous level), respectively (FIG. 18). Thereafter, biopterin had an elimination half-life ($t_{1/2}$) of about 1.1 hr, returning to the endogenous level 9 hrs post-dosing for the 10 mg/kg dose and 24 hrs post-dosing for the 100 mg/kg dose (FIG. 18).

The bioavailability (F) after a 10 and 100 mg/kg oral administration were 6.8% and 11.8%, respectively, based on the area under the plasma concentration-time curve (ΔAUC) obtained by subtracting the endogenous level during a 10 mg/kg intravenous administration. Rate of GI absorption were 8.8% when measured using radioactive markers in urine. An estimate of the actual value would be approximately 10% oral bioavailability based on these data.

The ratio of reduced biopterin to total biopterins in plasma (i.e., the reduced-form ratio) was relatively static (73%-96%) (FIG. 19).

Example 2

Concentration Time Curve For Biopterin In Plasma After Single Oral Dose to Monkey The purpose of this study was to assess pharmacokinetics of sapropterin after a single oral administration in cynomolgus monkeys. A single dose of sapropterin (10 mg/kg) was administered orally to female cynomolgus monkeys (3/group) under fasting conditions.

Results

Figure 20:
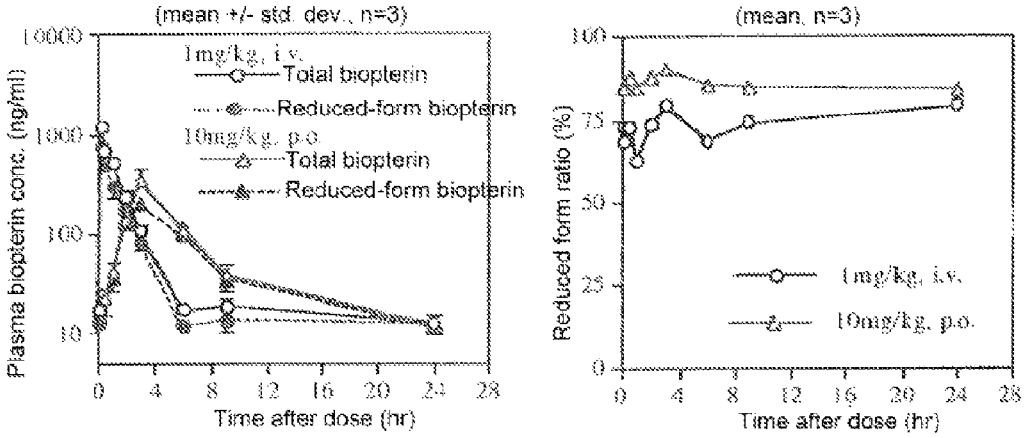
FIG. 20 shows plasma biopterin concentration and reduced-form ratio after a single-dose administration of sapropterin (BH4) in monkeys.

The total plasma biopterin concentration (ΔC) reached its maximum value 3 hrs post-dosing (344 ng/ml, approximately 20× endogenous levels) (FIG. 20). The plasma elimination half-life of biopterin was approximately 1.4 hrs, returning to the endogenous level within 24 hrs post-dosing. The ratio of reduced biopterin to total biopterins was nearly constant during the test period. The bioavailability (F) following a 10 mg/kg oral administration to female monkeys was about 9%, measured as ΔAUC oral/iv ratios (FIG. 21).

Example 3

Relative Bioavailability of Tetrahydrobiopterin (BH4) Administered After Dissolution of Tablet(s) in Water or Administered as Intact Tablet(s), and Effect of Food on Absorption in Healthy Subjects Objectives The primary objectives of the study were: (1) to evaluate the relative bioavailability of tetrahydrobiopterin (BH4, sapropterin dihydrochloride) when administered after dissolution of tablet(s) in water or administered as intact tablet(s); (2) to compare the effect of food on the bioavailability of BH4 in healthy subjects. The secondary objective of the study was to assess the safety and tolerability of single oral doses of BH4 in healthy subjects.

Methodology

This study was an open-label, randomized, three-treatment, six-sequence, three-period crossover study in which 30 subjects were to complete 3 single-dose dosing periods and were randomized to one of six sequence groups (Groups 1, 2, 3, 4, 5, and 6):

Group 1: a, b, c
Group 2: b, c, a
Group 3: c, a, b
Group 4: a, c, b
Group 5: b, a, c
Group 6: c, b, a where all dosing groups received BH4 10 mg/kg orally as follows:

a: administered after dissolution of tablet(s) in water given in fasting under fasting conditions
b: administered as intact tablet(s) given in fasting under fasting conditions
c: administered as intact tablet(s) given 30 minutes after beginning to ingest a high-calorie, high-fat meal in fed conditions Each subject received a single dose of 10 mg/kg of BH4 during each treatment period. A washout period of at least seven days separated each dose administration. A post-study assessment was performed 5-7 days after discharge of the third treatment period. Blood samples for Pharmacokinetic (PK) analysis were drawn at scheduled collection times during each study period: within 30 minutes prior to dose, and 0.5, 1.0, 1.5, 2.0, 2.5, 3.0, 3.5, 4.0, 5.0, 6.0, 8.0, 10.0, 12.0, 18.0, and 24.0 hours post-dose.

Dose and Mode of Administration

BH4 tablets were administered as 10 mg/kg dosages per treatment period. Tablets were administered by a) dissolution in water given in a fasted state, b) as intact tablets given in a fasted state, or c) as intact tablets given in a fed state.

Each dose of study drug was prepared and administered in liquid (solution) form mixed with water. The water supplied was ambient temperature tap water. Dosing solutions were prepared within 15 minutes of scheduled dose time. Dissolution of the tablet in liquid took approximately 1 to 3 minutes. The tablets were broken up or crushed in the dosing cup prior to dissolution in order to improve dissolution rate.

At the designated morning dosing time, BH4 was administered orally as the number of tablets equivalent to a 10 mg/kg dose, dissolved in 120 mL of water or orange juice. Each subject was observed closely as the entire 120 mL dose was consumed within 15 minutes of preparation. Immediately after the dose had been consumed, the dosing cup was rinsed with 60 mL of water and the subject consumed the rinse. A second 60 mL water rinse was added to the dosing cup and then the subject consumed the second rinse. The entire dosing procedure was completed in a 1-minute time period. A qualified staff person inspected the dosing cup and each subject's mouth immediately after completion of the dose to ensure that the entire dose was consumed. Alternatively, the subject swallowed a pill containing the BH4 rather than dissolving it in water. For each individual, the dosing periods occurred with a minimum of 7 days between doses.

Food Intake Schedule

A snack was served the evening of check-in. All subjects were then required to fast for at least 10 hours prior to dosing.

Fasting Conditions

Subjects receiving treatments administered under fasting conditions were dosed after they completed a minimum 10-hour overnight fast.

The subjects continued to fast for 4 hours post dose. Water was allowed ad lib during the study except for 1 hour prior through 1 hour post-dose. Standardized meals were provided at approximately 4 and 10 hours after drug administration and at appropriate times thereafter.

Non-Fasting Conditions

Subjects receiving treatments administered under non-fasting conditions were dosed after consuming a high-calorie, high-fat breakfast meal. Subjects received the following standard high-fat (approximately 50% of total caloric content of the meal), high-calorie (approximately 1000 calories) breakfast that began 30 minutes prior to scheduled administration of the dose and ended (last bite taken) within 5 minutes prior to dosing.

2 eggs fried in butter
2 strips of bacon
2 slices of toast with butter
4 ounces of hash brown potatoes
8 ounces of whole milk This meal contained approximately 150 protein calories, 250 carbohydrate calories, and 500-600 fat calories. An equivalent meal was substituted with documentation of the menu and caloric contents.

The subjects then fasted for 4 hours post dose. Water was allowed ad lib during the study except for 1 hour prior through 1 hour post-dose. Standard meals were provided at approximately 4 and 10 hours after drug administration and at appropriate times thereafter.

Duration of Treatment

Three single-dose treatment periods were each separated by a minimum of 7 days.

A follow-up visit was conducted 5 to 7 days after the last treatment visit.

Safety Variables: Evaluation and Methods

Safety was evaluated for all subjects who take at least one dose of BH4.

Efficacy and Safety Measurements Assessed and Flow Chart

Safety was evaluated by recording the incidence of adverse events, changes in 12-lead ECG parameters, vital signs and physical examination results, and changes in baseline in laboratory test values. The schedule for these assessments is shown in FIG. 22.

Physical Examinations and Vital Signs

Each subject underwent a routine physical examination by the study investigator. The physical examination included evaluation of head, eyes, ears, nose, throat, neck, heart, chest, lungs, abdomen, extremities, peripheral pulses, neurologic status, skin, and other physical conditions of note are evaluated. This study protocol did not require genitourinary examinations.

Height (in centimeters) and weight (in kilograms) were measured and body mass index (BMI) was calculated (BMI=weight (kg)/[height(m)]$^2$).

Blood pressure was measured in the sitting position according to the American Heart Association recommendations. Subjects were at rest with their feet on the floor for 5 minutes in the sitting position when blood pressure was measured.

Heart (pulse) rate was measured while the subject was in the sitting position.

A standardized 12-lead electrocardiogram (ECG) recording was taken at screening and at study discharge. ECGs were evaluated by a qualified investigator. Copies of the ECG and evaluation reports were kept as part of each subject's file.

The medical history, clinical laboratory test results and ECG tracing(s) were reviewed and evaluated by the Principal Investigator to determine clinical eligibility of each subject to participate in the study.

Clinical Laboratory Assessments

Hematology:

The following were evaluated: hemoglobin, hematocrit, total and differential leukocyte count, red blood cell (RBC) and platelet count.

In addition, blood was tested for Hepatitis B Surface Antigen, Hepatitis C Antibody and Human Immunodeficiency Virus (HIV).

Chemistry:

The following were evaluated: albumin, blood urea nitrogen (BUN), creatinine, total bilirubin, alkaline phosphatase (ALP), aspartate transaminase (AST), alanine transaminase (ALT), sodium ($Na^+$), potassium ($K^+$), chloride ($Cl^-$), lactic dehydrogenase (LDH), uric acid, and glucose.

Urinalysis:

The following were evaluated by the urine dipstick method: pH, specific gravity, protein, glucose, ketones, bilirubin, blood, nitrite, and urobilinogen. If protein, occult blood, or nitrite values are out of range, a microscopic examination is performed.

Urine samples were also tested for drugs of abuse (amphetamines, barbiturates, benzodiazepines, cannabinoids, cocaine and opiates).

Adverse Events

In this study, an adverse event (AE) was defined as any untoward medical occurrence in a subject or clinical investigation subject administered BH4, at any dose, whether or not it has a causal relationship with the event. An AE can therefore be any unfavorable and unintended sign (including an abnormal laboratory finding), symptom, or disease temporally associated with the use of BH4, whether or not related to BH4. This definition included intercurrent illnesses or injuries and exacerbation (increase in frequency, severity or specificity) of pre-existing conditions.

The reporting period for AEs began with the first administration of BH4. The reporting period for serious adverse events (SAEs) began earlier, from the time of the signing of the Informed Consent. SAEs were defined later in this section. The investigator monitored all AEs until resolution or, if the AE was determined to be chronic, a cause was identified. If an AE remained unresolved at the conclusion of the study, the PI and Medical Monitor made a clinical assessment as to whether continued follow-up of the AE was warranted, and documented the results. Assessment of severity was one of the responsibilities of the investigator in the evaluation of AEs and SAEs. The investigator was responsible for applying his or her clinical judgment to assess the causal relationship of each AE to BH4.

Serious Adverse Events

A serious adverse event (SAE) was defined as any AE that has at least one of the following outcomes:

Resulted in death

Was life-threatening, that is, placed the subjects at immediate risk of death from the event as it occurred This definition did not include a reaction that, had it occurred in a more severe form, might cause death Required inpatient hospitalization or prolongation of existing hospitalization Admission of a subject to the hospital as an inpatient as a result of an AE, even if the subject was released on the same day, qualified as hospitalization. An emergency room visit did not constitute hospitalization.

Resulted in persistent or significant disability or incapacity

An event qualified as resulting in a persistent or significant disability or incapacity if it involved a substantial disruption of the subject's ability to carry out usual life functions. This definition was not intended to include experiences of relatively minor or temporary medical significance.

Was a congenital anomaly or birth defect, that is, an AE that occurred in the child or fetus of subject exposed to study drug prior to conception or during pregnancy Was an important medical event that did not meet any of the above criteria, but could jeopardize the subject or required medical or surgical intervention to prevent one of the outcomes listed above.

More than one of the above outcomes could apply to any specific event.

Appropriateness of Measurements

The measures of safety in this study were routine physical examinations, vital signs, adverse event incidence and severity, and clinical and laboratory procedures.

Drug Concentration Measurements

Blood (plasma) pharmacokinetic (PK) characteristics were assessed after each dose of study medication. All subjects remained seated in an upright position for 4 hours post-dose. The blood samples were drawn within 30 minutes prior to dose and at 0.5, 1.0, 1.5, 2.0, 2.5, 3.0, 3.5, 4.0, 5.0, 6.0, 8.0, 10.0, 12.0, 18.0, and 24.0 hours post dose. Samples were collected in appropriately labeled 6 mL $K_2$-EDTA purple top Vacutainer® tubes. Blood samples were centrifuged at approximately 3000 rpm at 4° C. for 10 minutes. From the resulting plasma, exactly 1 mL was removed from each sample using a pipet, and placed into an aliquot tube containing 0.1% w/v dithioerythritol. The sample was capped and vortexed for approximately 10 seconds using a VWR Mini Vortexer at speed 6. After completion of these steps, the sample was flash frozen in an isopropyl/dry ice bath and placed in a −70° C. freezer pending analysis.

Approximately 80 mL of blood was drawn during each treatment period (5 mL per timepoint) for the PK analysis.

Pharmacokinetics:

Pharmacokinetic (PK) analysis of plasma BH4 concentration-time data was performed using non-compartmental methods to obtain estimates of the following PK parameters:

- Peak plasma concentration ($C_{max}$) and time to peak concentration ($T_{max}$), obtained directly from the data without interpolation;
- λz, the apparent terminal elimination rate constant, determined by log-linear regression of the terminal plasma concentrations;
- Area under the plasma concentration-time curve from time zero to the time of last measurable concentration [AUC (0-t)], calculated by the linear trapezoidal method;
- The apparent elimination half-life (t½), calculated as 0.693/λz;
- Area under the plasma concentration-time curve from time 0 to infinity [AUC(inf)] where AUC(inf)=AUC(0-t)+$C_t$/λz and $C_t$ is the last measurable concentration.

Estimation of Absorption Rate

Subjects were given a 10 mg/kg oral or intravenous dose of BH4, followed by serial measurements of plasma total biopterin concentration to determine the rate of BH4 absorption from the gastrointestinal tract from the area under the plasma total biopterin concentration increase (ΔCp)-time curve (ΔAUC). It was anticipated that a lower dose of BH4 was required when administered intravenously in comparison with BH4 administered orally to achieve the same level of bioavailability. For example, it may require 10 mg/kg of BH4 given orally to achieve the same level of bioavailability as 1 mg/kg BH4 administered intravenously. Because the manner of administration enhanced bioavailability, it may require only 5 mg/kg of BH4 to achieve the same level of bioavailability as a 1 mg/kg IV dose of BH4.

The rate of BH4 absorption from the gastrointestinal tract was estimated from the area under the plasma total biopterin concentration increase (ΔCp)-time curve (ΔAUC) after the administration BH4 using the following formulas:

Estimation from AUC

Absorption rate(%)=

(ΔAUC after p.o. dose/ΔAUC after i.v. dose)×(i.v. dose/p.o. dose×100)

Statistical Methods:

Comparison of the pharmacokinetic parameters Cmax, AUC(0-t), and AUC(inf) for BH4 was conducted using an analysis of variance (ANOVA) model with sequence, subject within sequence, treatment, and period as the classification variables using the natural logarithms of the parameters as the dependent variables. The comparisons of interest were between the dissolved and intact tablet in the fasted state and the intact tablet in the fed and fasted states.

The data from all subjects completing at least two study periods were included in the PK statistical analyses. All subjects receiving at least one dose of study drug were included in the safety analyses.

All PK and associated statistical analyses were done using SAS® for Windows® Version 9.1.3 or higher.

To provide sufficient power to meet the objectives of the study, a sample size of approximately 30 subjects, each with 3 treatment periods, was considered adequate to provide estimates of the differences comparisons of interest. No formal sample size calculation was conducted.

Results

Pharmacokinetics

Intact Versus Dissolved Tablets

Figure 23:
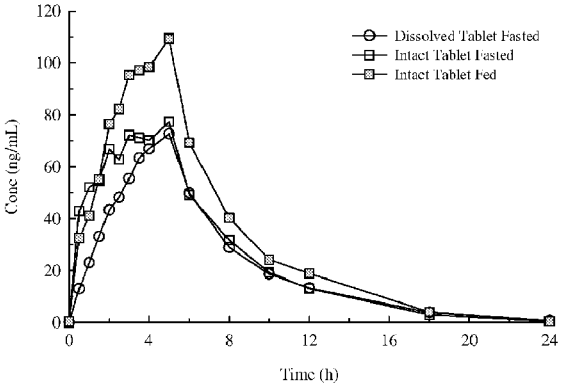
FIG. 23 shows the mean plasma concentrations of $BH_4$ after oral administration of 10 mg/kg of BH4 as dissolved and intact tablets under fasted conditions and intact tablets under fed conditions to healthy volunteers—linear axes.
Figure 24:
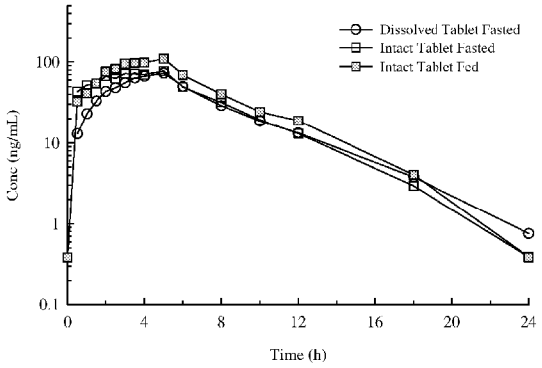
FIG. 24 shows the mean plasma concentrations of $BH_4$ after oral administration of 10 mg/kg of BH4 as dissolved and intact tablets under fasted conditions and intact tablets under fed conditions to healthy volunteers—semi-logarithmic axes.

Mean plasma concentrations of $BH_4$ were lower when BH4 was administered as a dissolved tablet compared to the intact tablet (FIGS. 23 and 24). Mean $C_{max}$ higher for the intact tablet as were mean values for AUC(0-t) and AUC(inf) (FIG. 25). The geometric mean ratios, intact-to-dissolved tablet, ranged from 118% to 121% and the upper limits of the associated 90% confidence intervals were greater than 125% (FIG. 26), indicating a statistically significant increase in absorption when the intact tablet is administered with a high-calorie, high-fat mealdifference in absorption between dissolved and intact tablet administration. The median and range for Tmax were essentially the same for the dissolved and intact tablets (FIG. 25), suggesting that the increase seen with the intact tablet was in the extent but not the rate of absorption.

Effect of High-Calorie, High-Fat Food on Drug Absorption

As expected, administration of the intact tablet with a standard high-fat high-calorie meal resulted in a substantial increase in the mean plasma $BH_4$ concentrations (FIG. 23) and mean values for Cmax, AUC(0-t), and AUC(inf) (FIG. 25). The geometric mean ratios (fed-to-fasted) ranged from 126% to 139% (FIG. 26) and, consequently, the upper limits of the associated 90% confidence intervals were greater than 125%, indicating a statistically significant difference in the effect of food on absorption compared to intact tablets. The median and range for Tmax were essentially the same under fed and fasted conditions (FIG. 25), suggesting that the increase seen with food was in the extent but not the rate of absorption of absorption.

Safety:

There were no serious adverse events (SAEs) in this study. Five (5) subjects reported a total of 9 adverse events (AE)s. Eight (8) of these 9 AEs were assessed as mild and 1 was assessed as moderate in severity. The most common AE was headache; 1 subject experienced a moderate headache which was assessed as unrelated to the study drug, and one subject experienced mild headache on two occasions, both of which were assessed as possibly related. In all, five events were judged to be unrelated and 4 were judged to be possibly related to the study drug. Study exit assessments, ECG and physical examination evaluations were completed with no clinically significant findings.

CONCLUSIONS

Administration of BH4 as an intact tablet resulted in an approximate 20% increase in the extent of absorption compared to a dissolved tablet.

Administration of BH4 as an intact tablet with a high-calorie, high-fat meal under fed conditions resulted in an approximate 30% increase in the extent of absorption compared to fasted conditions.

No clinically significant issues and safety parameters safety issues were identified in this study population. There were no AEs considered serious in this study. Among the 9 AEs reported, all but one, an instance of headache, was mild, and it was assessed to be unrelated to the study drug. Instances of fatigue and headache were the only AEs which were possibly related to the study drug, but and these were assessed as mild in severity.

Example 4

Formulation Approaches to Enhance Bioavailability of BH4

Two control formulations (BH4 intravenous formulation and BH4 tablet for oral solution) and six test formulations were selected for testing in animal studies. Each formulation prototype contained 80 mg or 100 mg of BH4.

BH4 Intravenous Formulations

Table 3 lists the composition of an intravenous formulation. BH4 was passed through a #20 mesh stainless screen before use while mannitol was used as received. This formulation was filled as a powder in a bottle and constituted with sterile water for injection prior to administration. Each bottle contained 100 mg of BH4 and 5 g of mannitol in a clear polyethylene terephthalate copolyester (PETG) bottle with a white high-density polyethylene (HDPE) screw top closure. Prior to administration, the formulation was constituted with 100 mL of sterile water for injection to yield a final concentration of 1 mg/mL. The IV formulation was supplied as a dry powder in a bottle, and each bottle contained the API and mannitol The powder was dissolved in sterile water for injection and filtered prior to administration by IV route.

TABLE 3

Composition of BH4 IV Formulation

| Ingredients | % (w/v) | mg/mL |
|---|---|---|
| BH4 | 0.1 | 1.0 |
| Mannitol (low in endotoxin), USP/Ph. Eur. | 5.0 | 50.0 |
| Sterile water for injection | qs 100 mL | qs 1 mL |

BH4 Tablet for Oral Solution

Table 4 lists the composition of an oral solution formulation. Ten (10) BH4 tablets (100 mg) were placed into a 125 mL graduated PETG bottle with a white HDPE closure. Prior to administration, the formulation was constituted with 100 mL of sterile water for injection to yield a final concentration of 10 mg/mL.

TABLE 4

Composition of BH4 Tablet, 100 mg

| Ingredients | % (w/w) | mg/tablet |
|---|---|---|
| BH4 | 33.33 | 99.99 |
| Ascorbic Acid, USP/EP | 1.67 | 5.01 |
| Crospovidone, USP/EP | 4.5 | 13.5 |
| Dicalcium Phosphate Anhydrous, USP/EP | 2.18 | 6.54 |
| Mannitol (Parteck M 200), UPS/EP | 57.06 | 171.18 |
| Riboflavin universal, USP/EP | 0.01 | 0.03 |
| Sodium Stearyl Fumarate (PRUV), NF/EP | 1.25 | 3.75 |
| Total | 100.00 | 300.00 |

Formulation Prototype to Slow Gastro-Intestinal Motility

Table 5 lists the composition of a delayed gastric emptying time prototype. BH4 was passed through a #20 mesh stainless steel screen before use. The Capmul GMO-50 was melted in a 37° C. water bath. BH4 and ascorbic acid were weighed and added slowly to the melted Capmul while stirring vigorously. The solid dispersion was added dropwise into a size #2 capsule using a pipette. Three filled capsules were placed in a 100 cc high-density polyethylene (HDPE) bottle with a heat-induction seal closure.

TABLE 5

Composition of BH4 Delayed Gastric Emptying Time Oral Capsule Formulation

| Ingredients | % (w/w) | mg/capsule |
|---|---|---|
| BH4 | 25 | 80 |
| Glyceryl mono/di-oleate (Capmul GMO-50) | 65 | 208 |
| Ascorbic acid fine powder | 10 | 32 |
| Total | 100 | 320 |

Bioadhesive Prototype

Table 6 lists the composition of a bioadhesive prototype. All materials, except for Carbopol 71G, were passed through a #20 mesh stainless steel screen. All materials were weighed and added to a plastic bag having a zip-locking closure, which was then shaken for a few minutes until the mixture appeared uniform. The powder was compressed into a tablet using a ¼" standard, round, concaved, plain-faced B tooling on a Globe Pharma MTCM-I manual press at 600 psi. Three tablets along with a silica gel desiccant canister were packaged in a 100 cc HDPE with a heat-induction seal closure.

TABLE 6

Composition of BH4 Bioadhesive Oral Tablet Formulation

| Ingredients | % (w/w) | mg/tablet |
|---|---|---|
| BH4 | 48.5 | 80.00 |
| Carbopol 71 G | 20.0 | 32.99 |
| Polycarbophil (Noveon AA1) | 20.0 | 32.99 |
| Ascorbic acid fine powder | 10.0 | 16.49 |
| Sodium stearyl fumarate (PRUV) | 1.5 | 2.47 |
| Total | 100.0 | 164.94 |

Sustained Release Prototype

Table 7 lists the composition of a sustained release prototype tested in the monkey. All materials, except for Methocel K100M Premium CR, were passed through a #20 mesh stainless steel screen. All materials were weighed and added to a plastic bag having zip-locking closure, which was then shaken for a few minutes until the mixture appeared uniform. The powder was compressed into a tablet using a ¼" standard, round, concaved, plain-faced B tooling on a Globe Pharma MTCM-I manual press at 1200 psi. The tablets along with a Silica gel desiccant canister were packaged in a 100 HDPE bottle with heat-induction seal closure.

TABLE 7

Composition of BH4 Sustained Release Tablet Formulation

| Ingredients | % (w/w) | mg/tablet |
|---|---|---|
| BH4 | 53.5 | 80.00 |
| Methocel K100M premium CR | 35.0 | 52.34 |
| Ascorbic acid fine powder | 10.0 | 14.95 |
| Sodium stearyl fumarate (PRUV) | 1.5 | 2.24 |
| Total | 100.0 | 149.53 |

Proton Donor Polymer Prototype

Table 8 lists the composition of a proton donor polymer prototype tested in the monkey. All materials, except for Eudragit L100-55 and Kollidon CL, were pre-screened using a #20 mesh stainless steel screen. All materials were weighed and added to a plastic bag having a zip-locking closure, which was then shaken for a few minutes until the mixture appeared uniform. A pre-weighed quantity of powder was filled into a size #2 capsule.

A coating solution was prepared by dissolving Eudragit L100-55 and Carbowax PEG 4600 in Ethyl Alcohol. The Eudragit L100-55 and Carbowax PEG 4600 were weighed and added to a 125 mL graduated polyethylene terephthalate copolyester bottle (PETG). The Ethyl Alcohol was added to the PETG bottle, and it was placed in a 40° C. water bath with sonication until the solution was clear.

The powder-filled capsules were manually dipped into the coating solution and allowed to dry at 40° C. for 20 minutes. The dried capsules were weighed and then rolled in Syloid FP244 to remove residual tackiness. Three capsules were packaged in a 100 cc HDPE bottle with a heat-induction seal closure.

TABLE 8

Composition of BH4 Proton Donor Capsule Formulation

| Ingredients Composition of Capsule | % (w/w) | mg/capsule |
|---|---|---|
| BH4 | 40.0 | 80 |
| Eudragit L100-55 | 44.5 | 89 |
| Crospovidone (Kollidon CL) | 4.0 | 8 |
| Ascorbic acid fine powder | 10.0 | 20 |
| Sodium stearyl fumarate (PRUV) | 1.5 | 3 |
| Total | 100.0 | 200 |
| **Ingredients Composition of Capsule Coating** | **% (w/w)** | **mg/capsule[1]** |
| Eudragit L100-55 | 5.0 | ND |
| Polyethylene glycol 4600 (Carbowax Sentry) | 5.0 | ND |
| Ethyl alcohol, 200 proof | 100 mL | ND |

[1]Following capsule coating and drying M the oven at 40° C., the capsule gains about 1 to 3% weight in polymer coating.
ND = Not Determined

Floating Delivery System

Table 9 lists the composition of a floating delivery system. All materials, except for Eudragit L100-55, were passed through a #20 mesh stainless steel screen. This tablet prototype comprised three layers; the middle layer contained the drug substance, which was sandwiched between two water-insoluble outer layers. The inner and outer materials were weighed and added separately to plastic bags having zip-locking closures, which were then shaken until the mixtures appeared uniform.

The two outer layers (12 mg each) and inner layer (14.5 mg) were weighed. One of the outer layers was added to the press, followed by the inner layer, and then the last outer layer. The layers were compressed into a tablet using a 3/16" round, beveled, plain-faced B Tooling on a Globe Pharma MTCM-I manual press at 200 psi.

A coating solution was prepared by dissolving Ethocel and PEG 4600 in an ethyl alcohol and purified water mixture. The ingredients were added to a PETG bottle, which was mixed and placed in a 40° C. water bath with sonication until the solution appeared clear.

The tablets were manually dipped in the coating solution and allowed to dry for 20 minutes at 40° C. Each tablet was re-weighed after coating. Seven (7) tablets were placed into each of the size #2 elongated capsules. Three capsules were packaged in a 100 cc HDPE bottle with a heat-induction seal closure.

TABLE 9

Composition of BH4 Floating Dosage Formulation

| Ingredients Outer Layers 1 and 3 | % (w/w) | mg/tablet |
|---|---|---|
| Eudragit L100-55 | 49.5 | 5.94 |
| Stearic acid | 49.5 | 5.94 |
| Sodium stearyl fumarate (PRUV) | 1.0 | 0.12 |
| Total | 100.0 | 12.00 |
| **Ingredients Middle Layer 2** | **% (w/w)** | **mg/tablet** |
| BH4 | 79.0 | 11.46 |
| Stearic acid | 10.0 | 1.45 |
| Ascorbic acid fine powder | 10.0 | 1.45 |
| Sodium stearyl fumarate | 1.0 | 0.15 |
| Total | 100.0 | 14.51 |
| **Ingredients 7 tablets in a Capsule** | **% (w/w)** | **mg/capsule** |
| BH4 | 29.8 | 80.19 |
| Stearic acid | 34.6 | 93.31 |
| Ascorbic acid fine powder | 3.8 | 10.15 |
| Eudragit L100-55 | 30.8 | 83.16 |
| Sodium stearyl fumarate (PRUV) | 1.0 | 2.70 |
| Total | 100.0 | 269.51 |
| **Ingredients Tablet Coating Solution** | **% (w/w)** | **mg/capsule[1]** |
| Ethocel Standard 10 FP | 5.0 | ND |
| Carbowax PEG 4600 | 5.0 | ND |
| Ethanol 200 proof | 95.0 mL | ND |
| Purified Water | 5.0 mL | ND |

[1]Following capsule coating and drying in the oven at 40° C., the capsule gains about 3 to 8% weight in polymer coating.
ND = Not Determined

Gas Generating Floating Delivery System

Table 10. lists the composition of a gas generating floating delivery system. This formulation was composed of a core tablet containing the drug substance surrounded by a gas-generating outer layer. All materials, except for sodium bicarbonate and Methocel K100M CR, were pre-screened using a #20 mesh stainless steel screen. The inner core and outer layer materials were weighed and added separately to plastic bags having zip-locking closures, which were closed and shaken until the mixture appeared uniform. The blended powder for the inner core (35 mg) was compressed into a tablet using a 1/8" round, beveled, plain faced B Tooling on a Globe Pharma MTCM-I manual press at 800 psi.

A coating solution was prepared by dissolving using Ethocel and PEG 4600 in ethyl alcohol. The inner core tablets were manually dipped in the coating solution and allowed to dry for 20 minutes at 40° C. The blended powder for the outer layer (40 mg) was weighed. One half was added to the press, followed by the inner core tablet, and then the second half of the outer layer. The tablet was compressed using a 3/16" round, beveled, plain-faced B Tooling on a Globe Pharma MTCM-I manual press at 800 psi. Four (4) tablets were placed into each size #2 capsule.

TABLE 10

Composition of BH4 Gas Generating Floating Dosage Formulation

| Ingredients<br>Inner tablet Core | % (w/w) | mg/tablet |
|---|---|---|
| BH4 | 58.3 | 20.39 |
| Ascorbic acid fine powder | 19.4 | 6.80 |
| HPMC K100MCR | 19.4 | 6.80 |
| Sodium stearyl fumarate (PRUV) | 2.9 | 1.02 |
| Total | 100 | 35.01 |
| **Ingredients<br>Outer Tablet Layer** | **% (w/w)** | **mg/tablet** |
| HPMC K100MCR | 46.1 | 18.46 |
| Citric acid anhydrous | 34.2 | 13.68 |
| Sodium bicarbonate | 17.1 | 6.84 |
| Sodium stearyl fumarate | 2.6 | 1.03 |
| Total | 100 | 40.01 |
| **Ingredients<br>Four tablets in a Capsule** | **% (w/w)** | **mg/capsule** |
| BH4 | 27.2 | 81.55 |
| Ascorbic acid fine powder | 9.1 | 27.18 |
| HPMC K100MCR | 33.7 | 101.03 |
| Citric acid anhydrous | 18.2 | 54.70 |
| Sodium bicarbonate | 9.1 | 27.35 |
| Sodium stearyl fumarate | 2.7 | 8.18 |
| Total | 100 | 299.99 |
| **Ingredients<br>Coating Solution** | **% (w/w)** | **mg/capsule[1]** |
| Ethocel Standard 10 FP | 5.0 | ND |

[1]Following capsule coating and drying in the oven at 40° C., the capsule gains weight in polymer coating.
ND = Not Determined Bioadhesive Granule Prototype Table 11 lists the composition of a bioadhesive granule prototype. All materials, except for Methocel K100M CR, were pre-screened using a #20-mesh stainless steel screen. All materials, except for the sodium stearyl fumarate (PRUV), were weighed and placed into a size #1 granulator bowl (LB Bohle Mini Granulator BMG). The powder was mixed at an impeller speed of 300 rpm and a chopper speed of 2500 rpm for five minutes until the mixture appeared uniform. Maintaining the impeller and chopper speeds, 5 mL of ethyl alcohol was added dropwise to the mixture until granules formed. The wet mass was removed from the granulation bowl and screened through an 18-mesh stainless steel screen. The granules were collected and placed in a 40° C. oven to dry for one hour. The loss on drying of the granules was determined to be 1.93% after one hour of drying. The granules were weighed and placed into a plastic bag having a zip-locking closure. Sodium stearyl fumarate (PRUV) was added to the dried granules in the bag. The bag was closed and shaken until the sodium stearyl fumarate (PRUV) appeared evenly distributed among the granules. The granules were weighed (134 mg). Size 2 elongated capsules were filled with portions of the granules alternating with drops of partially hydrogenated vegetable oil (350 μL). Three capsules were packaged in a 100 cc HDPE bottle with a heat-induction seal closure.

TABLE 11

Composition of BH4 Bioadhesive Granule Capsule Formulation

| Ingredients | % (w/w) | mg/capsule |
|---|---|---|
| BH4 | 60 | 80.00 |
| Methocel K100M CR | 19 | 25.33 |
| Carbopol 971 | 10 | 13.33 |
| Ascorbic Acid fine power | 10 | 13.33 |
| Sodium Stearyl Fumarate (PRUV) | 1 | 1.33 |
| Pureco HSC-1 oil | | 350 μL |
| Total | 100 | 133.33 |

In Vitro Drug Release

In vitro drug release testing from tablets was conducted according to the USP 27 apparatus II specifications using a Distek 2100C Dissolution Tester (Distek, Inc., North Brunswick, N.J.), along with an Agilent UV-Visible spectroscopy system (Agilent Technologies, Santa Clara, Calif.). The dissolution medium used for the release testing of BH4 was 900 mL of 0.1N HCl. During dissolution testing, the media in each vessel was maintained at 37°±0.5° C. and agitated at 50 rpm. A sample volume of 5 mL was taken at pre-determined time points. To determine the concentration of BH4 in the samples, 250 μL of each sample was diluted with 500 μL of 0.1N HCl and the absorption was measured at 265 nm using a UV spectrometer (8453 UV-Visible Spectrophotometer, Agilent Technologies, Santa Clara, Calif.). The data were collected using ChemStation software (Rev. A.09.01[76], Agilent Technologies, Santa Clara, Calif.). All dissolution tests were performed in triplicate.

Tablet Buoyancy Testing

The buoyancy of the floating prototype tablets was first determined by placing the tablets in plastic cups with 25-50 mL of 0.1N HCl. This test determined the time necessary for the tablets to float as well as the duration of their floating with no agitation. Those prototypes that floated for at least four hours were submitted for dissolution testing. During the dissolution testing, the buoyancy of the tablets was determined using the paddle method at a rotation speed of 50 rpm. The state of the tablets was checked visually at various time points.

Disintegration Testing

Disintegration testing was conducted according to the USP-27 disintegration test specifications using a Distek 3100 Series Disintegration Tester (Distek Inc., North Brunswick, N.J.). The disintegration media used was 900 mL of 0.1N HCl or 900 mL of 0.2M Potassium Phosphate pH 5.8. During the disintegration testing the media in the vessels was maintained at 37°±0.5° C. The tablets and capsules were visually inspected for disintegration.

Tablet Hardness Testing

Tablet hardness was determined using a Dr. Schleuniger Pharmatron 8M Tablet Hardness Tester (Dr. Schleuniger® Pharmatron Inc., Manchester, N.H.). The tablets were placed into the jaw of the hardness tester, and the hardness was measured in kiloponds (Kp).

Tablet Thickness

The thickness of the tablets was measured using a Mitutoyo Digimatic Indicator (Mitutoyo Absolute, Dr. Schleuniger Pharmatron Inc., Manchester, N.H.). The tablets were placed under the thickness gauge and the value indicated was recorded in millimeters (mm).

Results and Discussion

Several prototypes were developed based on three concepts: gastroretentive, proton donor polymer to change intestinal pH, and sustained release dosage forms. The sections below described the formulation development of each prototype.

Figure 27:
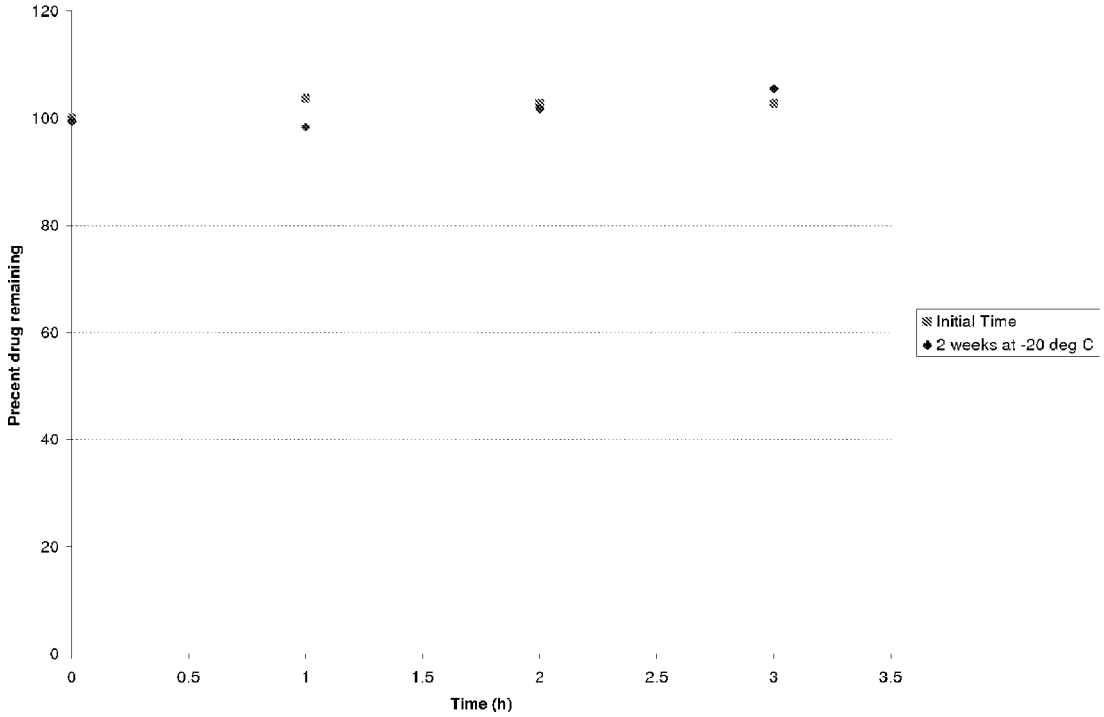
FIG. 27 shows a stability study of BH4 formulated with 5% mannitol in an aqueous solution both before and after two weeks stored at −20° C.

BH4 Intravenous Formulation—After sterile water constitution, the resulting solution was isotonic, pH 3.2 and contained 1 mg/mL of BH4, and was suitable for intravenous administration after sterile filtration through a 0.22 micron filter. Stability of the 1 mg/mL solution stored at ambient temperature was analyzed by HPLC every hour for three hours. The aged solution samples were then stored at −20° C. and analyzed by HPLC after 2 weeks. FIG. 27 indicates that the solution was stable at ambient temperature for at least 3 hours after constitution and was stable for at least 2 weeks during storage at −20° C.

BH4 Tablet for Oral Solution

Each bottle was packaged to contain ten (10) BH4 tablets, 100 mg. One-hundred (100) mL of purified water or sterile water for injection was added to the contents of each bottle. Following vigorous shaking of the bottle, the tablets rapidly disintegrated within 5 minutes. The resulting solution contained 10 mg/mL of BH4 for oral administration. Not all the ingredients in the tablet were soluble, and although the final solution appeared hazy or translucent, the active pharmaceutical ingredient was fully dissolved and the fine particulates were poorly soluble inactive ingredients.

Formulation Prototype to Slow Gastro-Intestinal Motility

Figure 28:
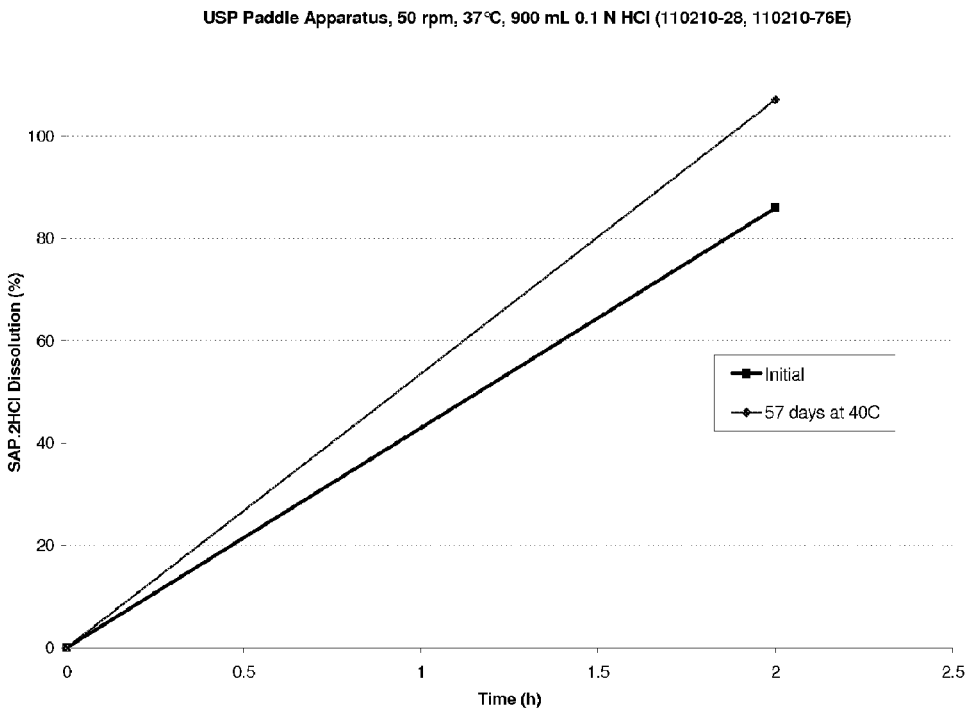
FIG. 28 shows a dissolution profile of a BH4 capsule formulation both before and after storage for 54 days at 40° C.

This capsule formulation comprised of BH4 and ascorbic acid dispersed in a semi-solid fatty acid derivative (glyceryl mono/di-oleate, melting point of 86° F. (30° C.)). Glyceryl mono/di-oleate (GMO) was also selected because GMO is chemically compatible with BH4. The dissolution profile depicted in FIG. 28 showed that over 90% of the drug was released in 2 hours and the dissolution profile remained unchanged after the capsules were stored at 40° C. for 57 days.

The drug dispersion in melted GMO, a semi-solid, was filled into hard gelatin capsules manually. The density of the semi-solid is greater than 1 g/mL, and it was possible to fill at least 80 mg dose at 25% drug loading in a size #2 capsule. It is expected that a size #0 capsule should be able to contain at least 200 mg of drug using the same formulation. Leakage of fatty acid from the capsule was observed during storage at 40° C. Preferably, capsules or softgel capsule formulations will be banded to avoid leaking of fatty acid during storage.

Bioadhesive Prototype

Many bioadhesives are made of either synthetic or natural polymers. Most of the current synthetic bioadhesive polymers are either polyacrylic acid or cellulose derivatives. Examples of polyacrylic acid-based polymers include but are not limited to carbopol, polycarbophil, polyacrylic acid (PAAc), etc. Cellulosics include but are not limited to hydroxypropyl cellulose and hydroxypropylmethyl cellulose (HPMC). Two bioadhesive prototypes were developed for testing in animal studies. The first prototype was a bioadhesive tablet formulation and the second a capsule containing bioadhesive granules.

Polycarbophil and carbomer polymers were selected for the development of the first bioadhesive tablet prototype. Carbopol 71 G is a granular form of carbomer and has good powder flow properties. All the batches of the fabricated tablets were of good quality with acceptable drug content (evident by close to 100% drug release in dissolution profiles) and acceptable hardness. Table 12 lists the representative tablet weight, thickness, and hardness of the bioadhesive prototype containing carbomer and polycarbophil.

TABLE 12

Representative Tablet Weight, Thickness and Hardness for Bioadhesive Prototype containing Carbomer and Polycarbophil

| Tablet Lot Number | Compression Pressure (psi) | Weight (mg) | Thickness (mm) | Hardness (Kp) |
|---|---|---|---|---|
| 11210-83 | 600 | 165.4 | 5.24 | 10.5 |
| 11229-4 | 600 | 166.7 | 5.64 | 10.3 |
| 11229-4 | 800 | 164.1 | 5.27 | 14.4 |
| 11229-4 | 1000 | 164.9 | 5.12 | 18 |

HPMC and carbomer polymers were used for the development of the second bioadhesive granules. HPMC was selected because it is used as low-density hydrocolloid system and controlled drug release independent of pH. Granules were selected over tablet to increase the chance of bioadhesion by increasing the surface area of the dosage form. To facilitate the separation of the granules-filled capsule in dissolution medium, the granules were coated partially with hydrogenated oil. Without the oil coating, the granules hydrated and formed a capsule-shaped matrix without disintegrating into individual granules.

Figure 29:
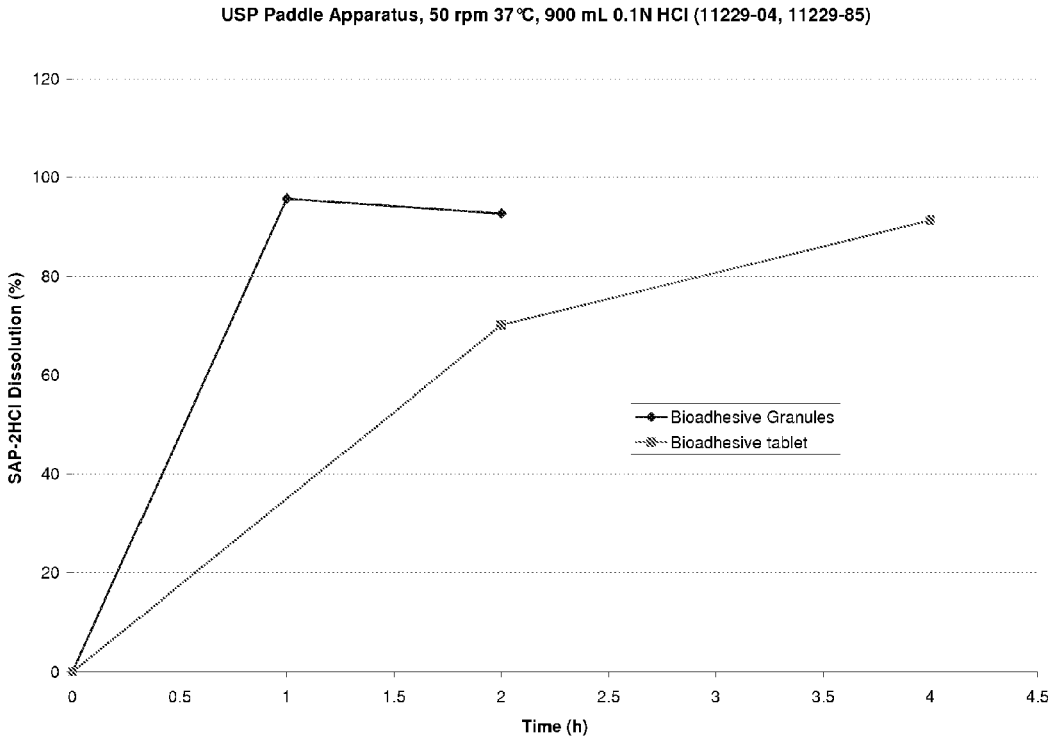
FIG. 29 shows a dissolution profile of two BH4 formulations—a BH4 bioadhesive tablet and BH4 bioadhesive granules.
Figure 30:
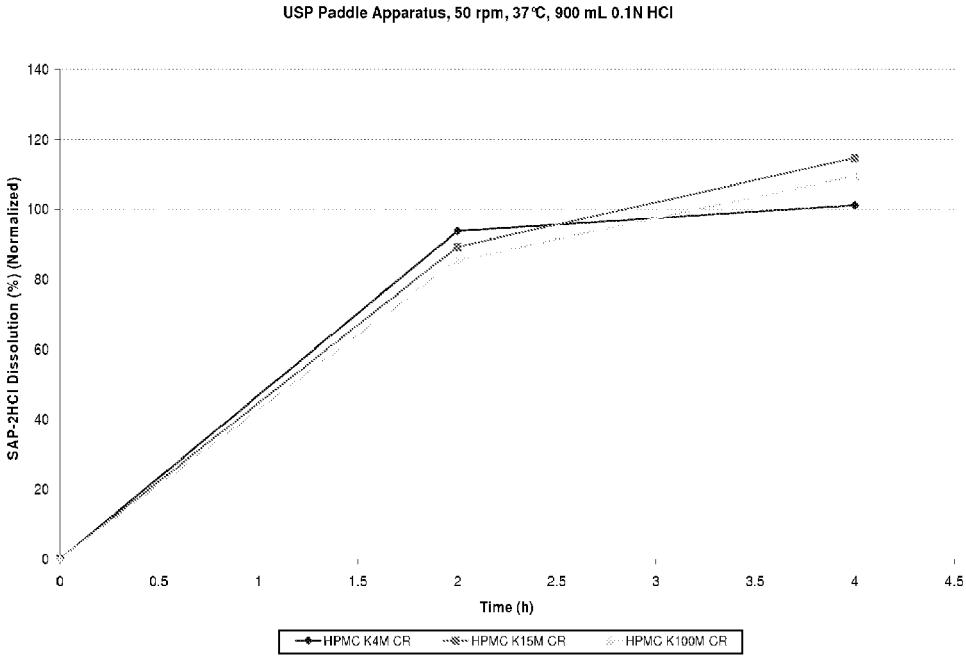
FIG. 30 shows a dissolution profile of various sustained release formulations of BH4.

The release profiles of the two bioadhesive prototypes (tablet and granules) are shown in FIG. 29, which shows that the release profile of the tablet was longer than the granules. Drug release was about 90% in four hours and 95% in one hour for the tablet and granules bioadhesive dosage forms, respectively. Upon storage at 40° C. and ambient humidity for one month without moisture protection (no heat induction seal), the tablet prototype exhibited a slowdown in drug dissolution (FIG. 29). For prototypes containing carbomer, moisture protection precaution should be taken to protect the tablet from possibly hydrating prematurely. Sustained Release Prototype Hydroxypropylmethylcellulose (HPMC) is used as a hydrophilic vehicle for the preparation of oral controlled drug delivery systems (Colombo, Adv. Drug Deliv. Rev, 1993, 11, 37). HPMC matrices are known to control the release of a variety of drugs (Chattaraj, et al. Drug Develop. Ind. Pharm., 1996, 22, 555; Pabon, et al., Drug Develop. Ind. Pharm., 1992, 18, 2163; Lee, et al., Drug Develop. Ind. Pharm., 1999, 25, 493; Basak, et al., Indian J. Pharm. Sci., 2004, 66, 827; Rajabi-Siabhoomi, et al., J. Pharm. Pharmacol., 1992, 44, 1062). Various viscosity grades of HPMC (K4M, K15M and K100 M) to control the release of BH4 were evaluated in this study. The dissolution profiles of tablets made with various grades of HPMC are shown in FIG. 30. Drug release profiles were similar at 20% HPMC regardless of viscosity grade; over 80% of the drug was released in 2 hours. When HPMC polymer was exposed to aqueous medium, it underwent rapid hydration and chain relaxation to form gel layer (Naruhashi, et al., Pharm Res. 2003, 19:1415-1421). The HPMC at 20% may not form a substantial gel barrier layer to slow the release of BH4 significantly.

Figure 31:
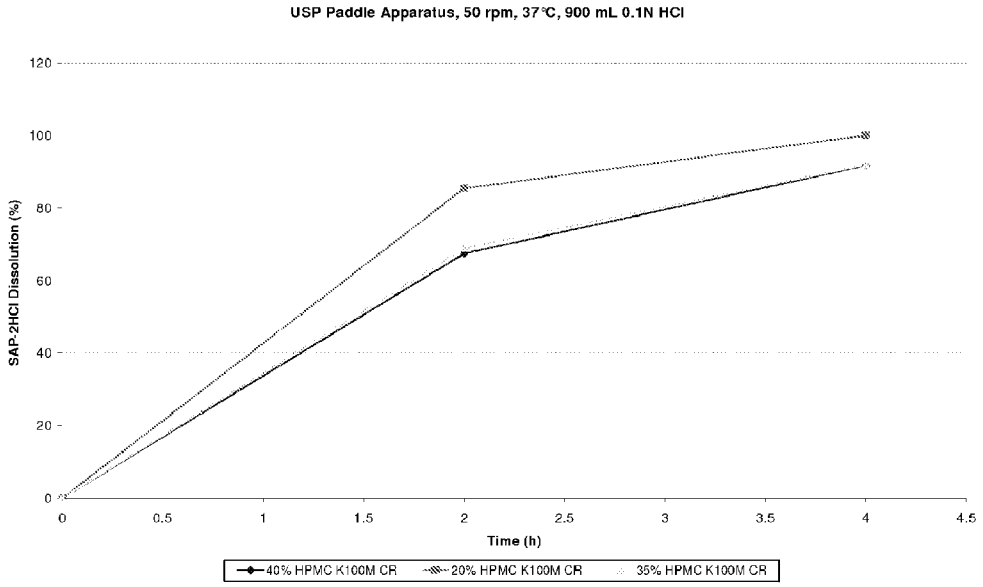
FIG. 31 shows a dissolution profile of various sustained release formulations of BH4.

The dissolution profiles of tablets produced with varying concentrations (20% to 40%) of a high viscosity grade of HPMC (Methocel K100M CR) are presented in FIG. 30. A tablet containing 35% to 40% Methocel K100M CR was found to slow drug release for up to four hours whereas 20% HPMC released drug in two hours (FIG. 31). A tablet containing 35% HPMC (Methocel K100M) was selected as the prototype for testing in animal studies because it contained the least amount of HPMC required to slow the drug release for up to four hours. As such, the tablets were of good quality with acceptable drug content as evident by close to 100% drug release in dissolution profiles.

Proton Donor Polymer Prototype

To increase the oral absorption of BH4, one approach is to stabilize the drug by decreasing the pH of the proximal small intestine. To manipulate intestinal luminal pH, Eudragit L100-55, a proton-releasing polymer commonly used for enteric coating, was selected. This polymer is not soluble under acidic conditions, and it becomes soluble and releases protons under weakly acidic (pH>5.5) to alkaline condition due to its carboxyl groups, thereby controlling the intestinal luminal pH to be acidic. Naruhashi, et al. (2003) found that pH in the lumen was decreased in a Eudragit L100-55 concentration-dependent manner and the absorption of cefadroxil and cefixime from the ileal loop was increased in the presence of the acidic polymer (Nozawa, et al., J. Pharm Sci. 2003, 92 (11), 2208-2216). Nozawa, et al (2003) showed than Eudragit decreased the pH in the intestinal loops, and increased the disappearance of both cefadroxil and cefixime from the loops.

Powder formulations containing BH4 and Eudragit L100-55 as shown in Table 8 were compressed into tablets and filled into capsules. The tablet formulation released about 27% drug in one hour in simulated gastric fluid (SGF) during dissolution testing. However, during disintegration testing, the tablet remained intact in SGF and pH 5.8 phosphate buffer (PB) for at least 2 hours. Even in the presence of a super-disintegrant (crospovidone or croscarmellose), the tablet failed to disintegrate. It is possible that the drug may be acidifying the Eudragit, creating a low micro pH environment such that the polymer remained unionized and insoluble.

The powder filled capsule drug-Eudragit formulation disintegrated rapidly in SGF. To target proton release in the proximal intestine, an enteric coat was applied to the capsule. Following capsule coating and drying in the oven at 40° C., the capsule gained about 1 to 3% weight in polymer coating. When tested using the USP dissolution apparatus II (paddle), dissolution medium 0.1 N HCl maintained at 37° C. at a rotational speed of 50 rpm, the coated capsule released about 25% of drug in one hour. Following 1 hour of acid (0.1 N HCl) pre-treatment, the coated capsule was placed in a USP disintegration Apparatus with 500 mL of pH 5.8 phosphate buffer maintained at 37° C., the coated capsule disintegrated in about 1 hour. The enteric-coated capsule prototype was selected over the tablet or the uncoated capsule because the enteric-coated capsule was more likely to deliver proton-releasing polymer to the target site.

Floating Delivery System

Figure 32:
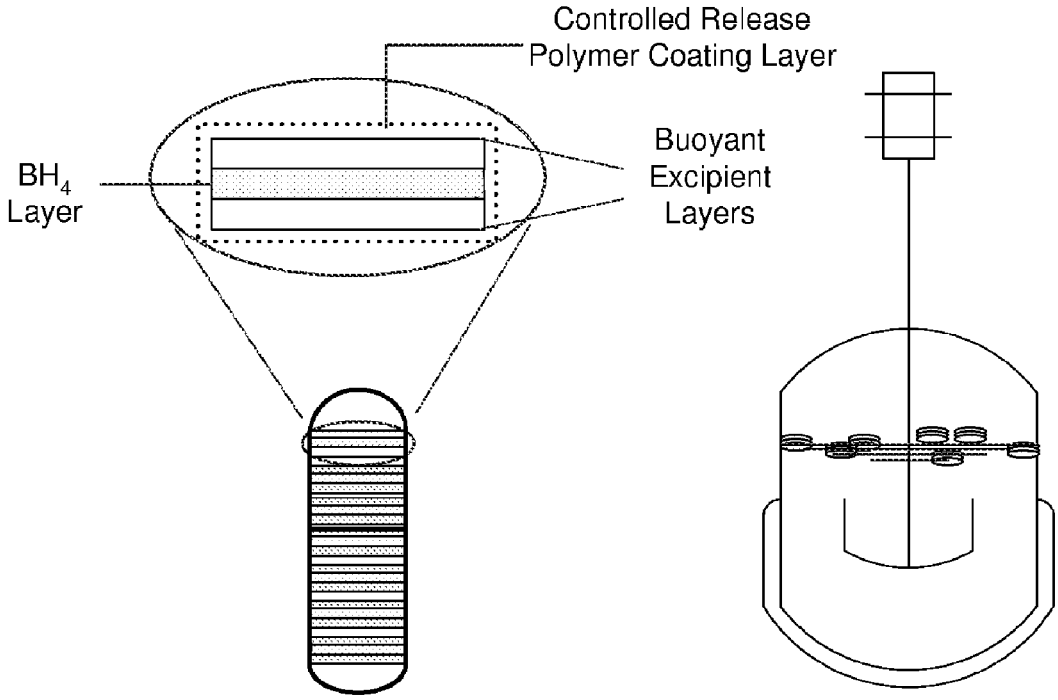
FIG. 32 shows a schematic diagram of a floating dosage formulations of BH4.

Two floating delivery systems were developed. The first prototype was a floating multiple unit dosage form; the purpose of this dosage form was to increase the chance that one of the units will remain in the gastric region and hence prolong the gastric residence time of drugs. This dosage form consisted of seven triple layer tablets in a capsule; the middle layer contained the drug substance, which was sandwiched between two water-insoluble outer layers (FIG. 32). The outer layers contained stearic acid, a hydrophobic and water-insoluble fatty acid, which provided the necessary buoyancy to the floating tablet. Each tablet was manually coated with an alcoholic solution of ethylcellulose and polyethylene glycol MW 4600 (PEG). Ethylcellulose formed a water insoluble film around the tablet and PEG, which acted as a pore former, modulated the release rate. The dissolution profiles of tablets coated with ethylcellulose and various concentrations (20% to 40%) of PEG solutions are presented in FIG. 33. It was noted that the coated triple layer tablet achieved close to zero-order release kinetics. As expected, the drug dissolution rate increased as the concentration of PEG increased. The tablets floated in simulated gastric medium for at least four hours during dissolution studies. Table 9 shows the composition of the formulation tested in animal studies.

Figure 33:
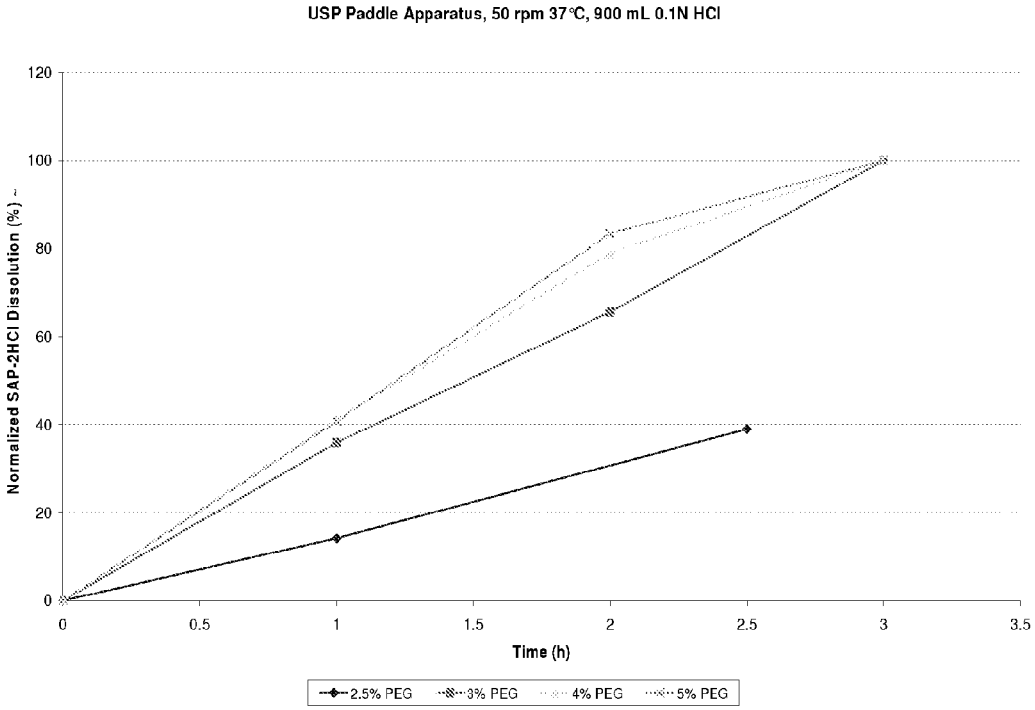
FIG. 33 shows a dissolution profile of various floating dosage formulations.
Figure 34:
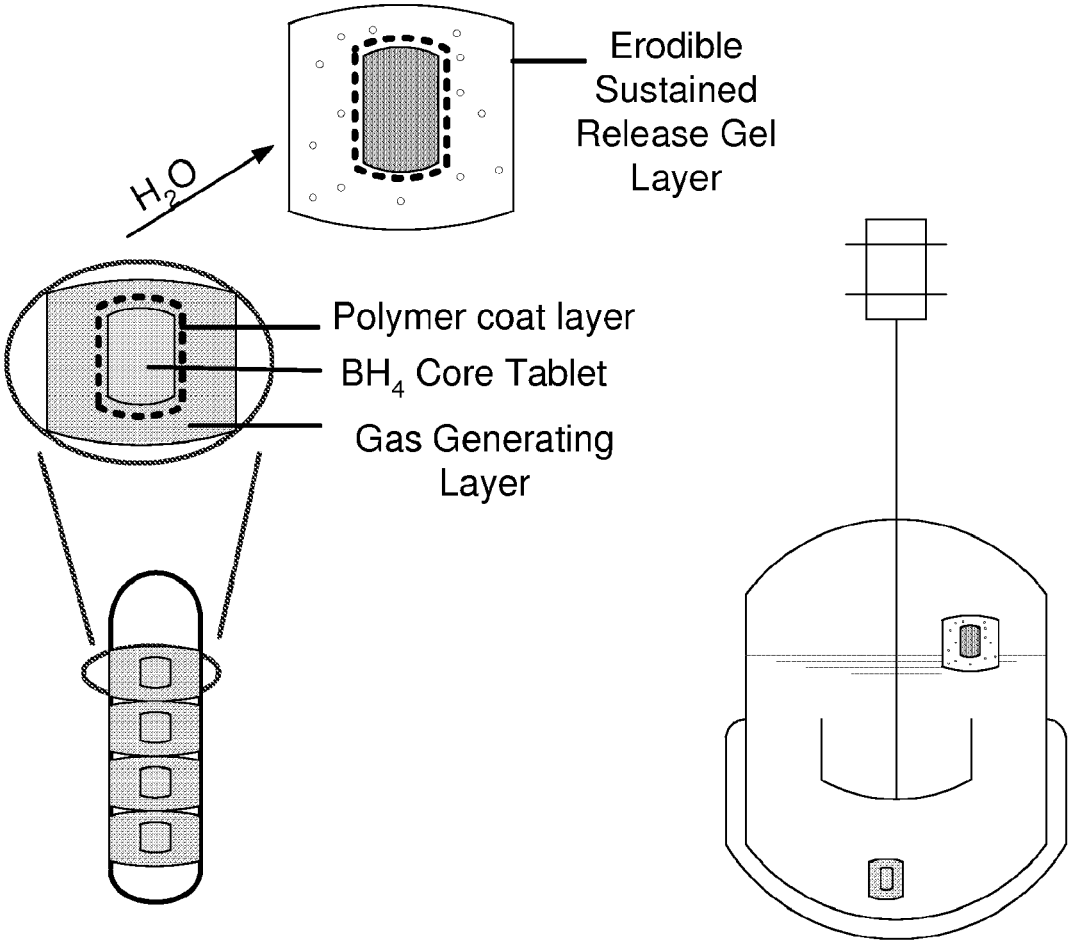
FIG. 34 shows a schematic diagram of gas generating dosage forms of BH4.

The second prototype was a gas-generating dosage form. It was formulated in such a way that when it came in contact with acidic gastric contents, carbon dioxide was liberated and got entrapped in the swollen hydrocolloids, which provided buoyancy to the dosage form (FIG. 33). This formulation floated in simulated gastric medium for at least four hours during dissolution studies. However, for such a system to work consistently, the tablets have to be produced in a low humidity environment to prevent premature acid and base reaction. There could be potential interaction between BH4 and sodium bicarbonate in the tablet during storage. For these reasons, this dosage form was not tested in animal studies.

Six prototype test formulations that incorporated various formulation approaches including proton donor polymer to decrease intestinal pH, gastroretentive dosage forms, and sustained released formulations, were developed for animal bioavailability studies.

Example 5

Bioavailability of Novel BH4 Formulations

The objective of this study was to enhance the absorption of BH4 by developing dosage forms that increase the residence time of the drug in the gastrointestinal (GI) tract.

Methods: Three healthy cynomolgus monkeys weighing 3-4 kg were used in open, 8-period non-crossover study to determine the bioavailability of seven formulations compared to a control dissolved BH4 formulation. After an overnight fast, the monkeys received, on separate occasions, a single dose of 80 mg of the same novel formulation orally or intravenously with an interval of at least a 1 week washout period between the various novel formulations studied. For intravenous administration, blood samples were collected before dosing and then at 5, 15 and 30 min and 1.0, 2.0, 4.0, 6.0, 8.0, 12 and 24 hr post dose. For oral administration, blood samples were taken before dosing and then 15 and 30 min and 1.0, 2.0, 3.0, 4.0, 6.0, 8.0, 12, and 24 hr following each dose. Following separation of the plasma by centrifugation, 200-μL aliquots of each sample were promptly transferred into individual tubes containing 0.1% DTE and frozen at −70° C. until ready for assay for total L-biopterin.

Study Formulations: The formulations administered are found in Table 13. Three of the formulations were conceptually designed to be gastroretentive via bioadhesive or floating mechanisms to increase GI residence time (carbomer-based, multi-particulate floating granules and bioadhesive granules). Other concepts were based on slowing GI motility to increase residence time of the formulation (glyceryl monooleate), reducing the pH of the small intestine and thereby enhancing BH4 chemical stability to enable absorption of intact drug (proton pump) or sustained delivery formulation to ascertain whether it will enhance absorption.

TABLE 13

| Phase | Prototype | Dosage Form | Concept | Ingredients |
|---|---|---|---|---|
| Phase I | IV Formulation | IV solution, 1 mg/mL | Control | BH4, D(−)-Mannitol |
| Phase II | Kuvan Tablets for Solution | Oral Solution, 10 mg/ml | Control | BH4 tablets manufactured by Lyne (Lot# 140651) |

TABLE 13-continued

| Phase | Prototype | Dosage Form | Concept | Ingredients |
|---|---|---|---|---|
| Phase III | Glycerol Mono Oleate | Capsule, 80 mg | Slow GI motility | BH4, Capmul GMO-50, Ascorbic Acid |
| Phase IV | Carbomer Prototype | Tablet, 80 mg | Gastro-retentive, Bioadhesive | BH4, Carbopol 71G, Noveon AA1, Ascorbic Acid, PRUV |
| Phase V | HPMC prototype | Tablet, 80 mg | Sustained release | BH4, Methocel K100M Premium CR, Ascorbic Acid, PRUV |
| Phase VI | Eudragit Prototype | Capsule, 80 mg | Proton donor polymer to lower GI pH | BH4, Eudragit L100-55, Ascorbic Acid, Kollidon CL, PRUV, Coating (Eudragit L100-55, Carbowax PEG 4600, Ethyl Alcohol 200 proof) |
| Phase VII | Multi-floating units | Multiple tablets in capsule, 80 mg | Gastro-retentive, floating | Inner Layer (BH4, Ascorbic Acid, Stearic Acid, PRUV), Outer Layer (Stearic Acid, Eudragit L100-55, PRUV), Coating (Ethocel Standard 10FP, Carbowax PEG 4600, 95% Ethanol) |
| Phase VIII | Bioadhesive Granules | Granules in capsule, 80 mg | Gastro-retentive, Bioadhesive | Intergranular (BH4, Methocel K100M Premium CR, Carbopol 971, Ascorbic Acid), Extragranular (PRUV, Pureco HSC-1 oil) |

Plasma Assay for Biopterin: BH4 concentrations in plasma were determined by using a validated, specific, reversed-phase LC/MS/MS method. The standard curve was linear over the concentration range of 50 ng/mL to 2500 ng/mL. The lower limit of quantitation for L-biopterin was 50 ng/mL with intraday precision shown by coefficients of variation less than 5%. L-biopterin is stable in frozen monkey plasma stabilized with 0.1% DTE at −70° C. until assayed. BH4 concentrations were calculated from the determined L-biopterin concentrations.

Pharmacokinetic and Statistical Analysis: Pharmacokinetic parameters were determined for plasma BH4 following the administration of the oral and intravenous formulations. The pharmacokinetic parameters are provided in Table 14.

TABLE 14

| Phase, Formulation | $AUC_{last}$ (ng-hr/mL) | $AUC_{\infty}$ (ng-hr/mL) | $C_{max}$ (ng/mL) | $C_{last}$[a] (ng/mL) | $T_{max}$ (hr) | $t_{1/2}$ (hr) |
|---|---|---|---|---|---|---|
| 2, dissolved tablet | 641 (88) | 805 (36) | 93.6 (31.3) | 9.60 (2.20) | 2.33 (0.58) | 11.7 (2.1) |
| 3, glyceryl mono-oleate | 716 (154) | 858 (317) | 133 (83) | 6.47 (3.60) | 2.00 (0) | 12.1 (10.3) |
| 4, bioahestive polymer | 593 (50.6) | 648 (114) | 108 (15) | 4.46 (3.36) | 2.67 (0.58) | 6.89 (3.51) |
| 5, sustained release | 355 (134) | 472 (36) | 86.0 (43.1) | 12.9 (12.4) | 3.33 (0.58) | 5.30 (1.73) |
| 6, proton donor | 276 (49.8) | 282 (49) | 68.3 (25.3) | 2.97 (0.71) | 3.33 (0.58) | 1.59 (0.74) |
| 7, floating dosage form | 304 (78) | b | 59.9 (31.8) | 5.90 (0.94) | 4.00 (2.00) | b |
| 8, bioadhesive granulations | 292 (79) | 366 (40.6) | 42.5 (12.6) | 5.11 (2.43) | 3.0 (0) | 15.3 (8.2) |

Results

Figure 35:
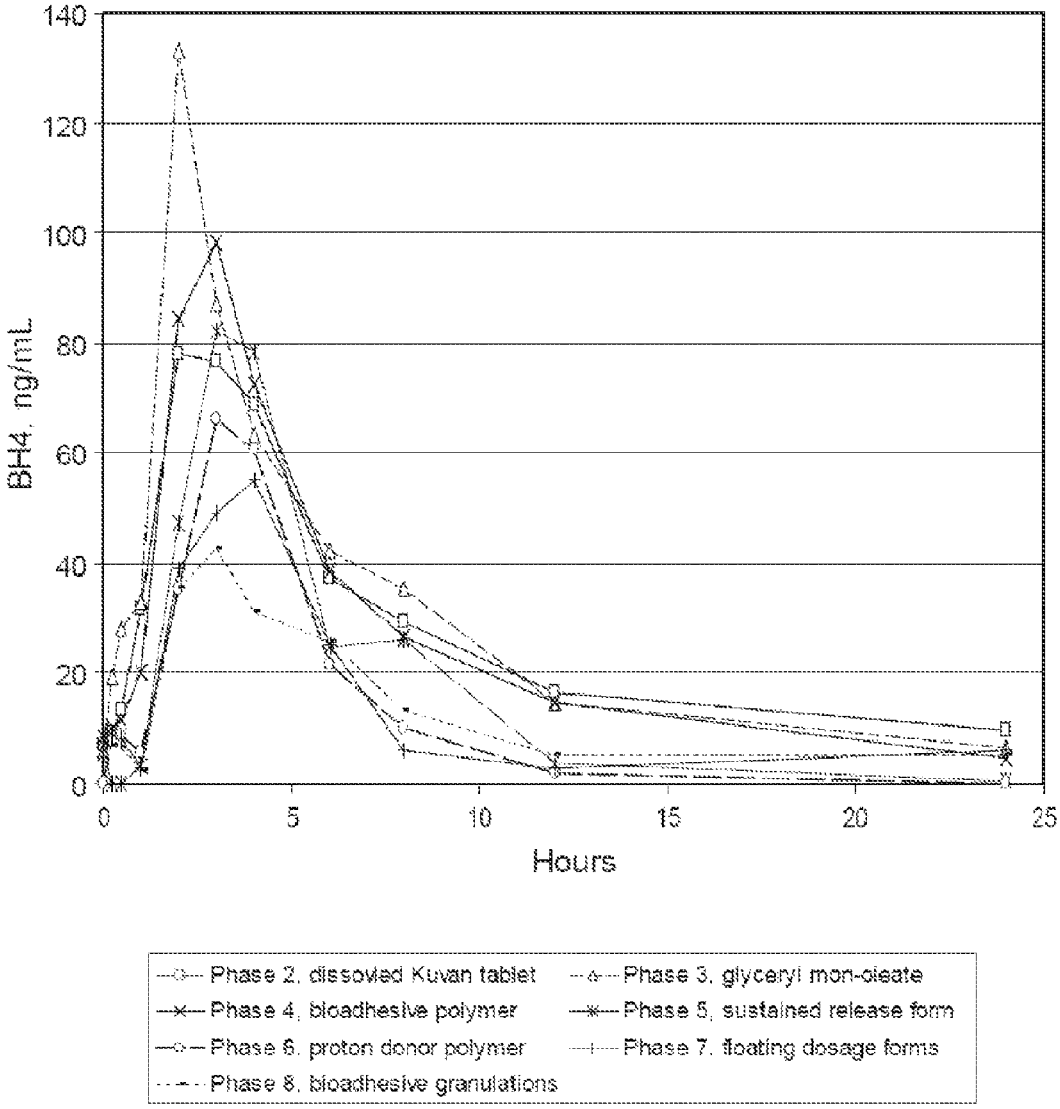
FIG. 35 shows a pharmacokinetic profile of various BH4 formulations.

The objective of this study was to identify formulations that enhance the bioavailability BH4 compared to the control dissolved tablet formulation. The mean plasma BH4 concentration-time profiles of the various dosage forms and the control formulation following the oral administration of BH4 are shown in FIG. 35, and the BH4 pharmacokinetic parameters derived from plasma drug concentration-time profiles are given in Table 14. The control formulation (phase 2) is the dissolved tablet.

As shown in FIG. 35, the glyceryl mono-oleate formulation provided the highest $AUC_{last}$ and $AUC_{\infty}$ which are 716 ng-hr/mL and 858 ng-hr/mL respectively. The control dissolved BH4 tablet formulation exhibited $AUC_{last}$ and $AUC_{\infty}$ which are 641 ng-hr/mL and 805 ng-hr/mL respectively (Table 14). The rank order of the formulations from the most to the least bioavailable is: glyceryl mono-oleate>dissolved tablet>bioadhesive polymer tablet>sustained release tablet>floating dosage forms>bioadhesive granulations capsule product>proton donor capsule product.

Example 6

Preparation of Intravenous Formulation of Tetrahydrobiopterin

Preformulation Stability Evaluation

In general, the objective of this study was to evaluate the stability of BH4 in buffer solutions ranging in pH from pH 1 to 7 (See Table 15) and in the presence and absence of antioxidants and with or without inert gas in the reaction solutions (See Table 16).

TABLE 15

Components and Composition of Buffer Solutions to be used for BH4 Preformulation Stability Studies

| Components | Quantities |
|---|---|
| pH 1.2 Buffer (0.1N HCl) | |
| Concentrated HCl (12N) | 8.33 mL |
| Sodium Chloride | 2.92 g |
| Distilled/Deionized Water qs | 1000 mL |

TABLE 15-continued

Components and Composition of Buffer Solutions to be used for BH4 Preformulation Stability Studies

| Components | Quantities |
|---|---|
| pH 2.1 Buffer (0.01N HCl) | |
| pH 1.2 (0.1N HCl) Buffer | 100 mL |
| Sodium Chloride | 7.79 g |
| Distilled/Deionized Water qs | 1000 mL |
| pH 3 Buffer | |
| Phosphoric Acid, 15M, 85% | .347 mL |
| Sodium Monobasic Phosphate, anhydrous ($NaH_2PO_4$) | 6.17 g |
| Sodium Chloride | 6.16 g |
| pH 4 Buffer | |
| Acetic Acid, Glacial, 100% | 2.38 mL |
| Sodium Acetate, Trihydrate | 1.29 g |
| Sodium Chloride | 8.22 g |
| Distilled/Deionized Water qs | 1000 mL |
| pH 5 Buffer | |
| Acetic Acid, Glacial, 100% | .87 mL |
| Sodium Acetate, Trihydrate | 4.78 g |
| Sodium Chloride | 6.72 g |
| Distilled/Deionized Water qs | 1000 mL |
| pH 6 Buffer | |
| 4-Morpholineethanesulfonic (MES) Acid Monohydrate | 4.99 g |
| MES Sodium Salt | 5.75 g |
| Sodium Chloride | 7.23 g |
| Distilled/Deionized Water qs | 1000 mL |
| pH 7 Buffer | |
| Sodium Monobasic Phosphate, Monohydrate ($NaH_2PO_4$) | 2.56 g |
| Sodium Dibasic Phosphate, anhydrous ($Na_2HPO_4$) | 4.44 g |
| Sodium Chloride | 2.18 g |
| Distilled/Deionized Water qs | 1000 mL |

TABLE 16

Composition of Buffer Solutions for Stability Studies Containing BH4 With or Without Antioxidant and whether Subjected to Gas Sparging or Not

| | Study Group Number | | | | |
|---|---|---|---|---|---|
| pH | 1 Buffer Study | 2 Buffer + Ascorbic Acid Study | 3 Buffer + L-Cysteine Study | 5 Buffer + Argon Sparging Study | 6 Buffer + Oxygen Sparging Study |
| 1 | 1 mg/mL BH4 in pH 1.2 Buffer | 1 mg/mL BH4 and 1 mg/mL Ascorbic Acid in pH 1.2 Buffer | 1 mg/mL BH4 and 1 mg/mL L-Cysteine in pH 1.2 Buffer | 1 mg/mL BH4 in pH 1.2 Buffer and Argon-Sparged and Argon blanket-Sealed | 1 mg/mL BH4 in pH 1.2 Buffer and Oxygen-Sparged and $O_2$ blanket-Sealed |
| 2 | 1 mg/mL BH4 in pH 2.1 Buffer | 1 mg/mL BH4 and 1 mg/mL Ascorbic Acid in pH 2.1 Buffer | 1 mg/mL BH4 and 1 mg/mL L-Cysteine in pH 2.1 Buffer | 1 mg/mL BH4 in pH 2.1 Buffer and Argon-Sparged and Argon blanket-Sealed | 1 mg/mL BH4 in pH 2.1 Buffer and Oxygen-Sparged and $O_2$ blanket-Sealed |
| 3 | 1 mg/mL BH4 in pH 3 Buffer | 1 mg/mL BH4 and 1 mg/mL Ascorbic Acid in pH 3 Buffer | 1 mg/mL BH4 and 1 mg/mL L-Cysteine in pH 3 Buffer | 1 mg/mL BH4 in pH 3 Buffer and Argon-Sparged and Argon blanket-Sealed | 1 mg/mL BH4 in pH 3 Buffer and Oxygen-Sparged and $O_2$ blanket-Sealed |
| 4 | 1 mg/mL BH4 in pH 4 Buffer | 1 mg/mL BH4 and 1 mg/mL Ascorbic Acid in pH 4 Buffer | 1 mg/mL BH4 and 1 mg/mL Ascorbic Acid in pH 4 Buffer | 1 mg/mL BH4 in pH 4 Buffer and Argon-Sparged and Argon blanket-Sealed | 1 mg/mL BH4 in pH 4 Buffer and Oxygen-Sparged and $O_2$ blanket-Sealed |
| 5 | 1 mg/mL BH4 in pH 5 Buffer | 1 mg/mL BH4 and 1 mg/mL Ascorbic Acid in pH 5 Buffer | 1 mg/mL BH4 and 1 mg/mL L-Cysteine in pH 5 Buffer | 1 mg/mL BH4 in pH 5 Buffer and Argon-Sparged and Argon blanket-Sealed | 1 mg/mL BH4 in pH 5 Buffer and Oxygen-Sparged and $O_2$ blanket-Sealed |
| 6 | 1 mg/mL BH4 in pH 6 Buffer | 1 mg/mL BH4 and 1 mg/mL Ascorbic Acid in pH 6 Buffer | 1 mg/mL BH4 and 1 mg/mL L-Cysteine in pH 6 Buffer | 1 mg/mL BH4 in pH 6 Buffer and Argon-Sparged and Argon blanket-Sealed | 1 mg/mL BH4 in pH 6 Buffer and Oxygen-Sparged and $O_2$ blanket-Sealed |
| 7 | 1 mg/mL BH4 in pH 7 Buffer | 1 mg/mL BH4 and 1 mg/mL Ascorbic Acid in pH 7 Buffer | 1 mg/mL BH4 and 1 mg/mL L-Cysteine in pH 7 Buffer | 1 mg/mL BH4 in pH 7 Buffer and Argon-Sparged and Argon blanket-Sealed | 1 mg/mL BH4 in pH 7 Buffer and Oxygen-Sparged and $O_2$ blanket-Sealed |

More specifically, the influence of combining two antioxidants in the presence or absence of inert gas was evaluated at pH 4 to support the formulation of a liquid product, and at a pH 7 to ascertain the contribution of instability at physiologic pH to the low bioavailability of the compound in monkeys and humans (See Tables 17 and 18). The stability of BH4 is expected to be temperature-dependent. Therefore, the compound stability was evaluated at 2-8° C., 25° C., 30° C. and 37° C. to support the determination of predictive long-term shelf lives for the compound at different temperatures. Determination of the stability of the compound at the physiologic temperature of 37° C. provides data to support the estimation of the stability lifetime of a formulated oral dosage form in the absorptive regions of the GI tract.

TABLE 17

Composition of Buffer Solutions for the pH 4 Stability Study of BH4

| pH 4 | pH 4 |
|---|---|
| Buffer + Ascorbic Acid + L-Cysteine Study 1 mg/mL BH4 and 1 mg/mL Ascorbic Acid and 1 mg/mL L-Cysteine in pH 4 Buffer | Buffer + Ascorbic Acid + L-Cysteine + Argon Sparge Study 1 mg/mL BH4 + 1 mg/mL Ascorbic Acid + 1 mg/mL L-Cysteine in pH 4 Buffer and Argon-Sparged and Argon blanket-Sealed |

TABLE 18

Composition of Buffer Solutions for the pH 7 Stability Study of BH4

| pH 7 | pH 7 |
|---|---|
| Buffer + Ascorbic Acid + L-Cysteine Study 1 mg/mL BH4 and 1 mg/mL Ascorbic Acid and 1 mg/mL L-Cysteine in pH 7 Buffer | Buffer + Ascorbic Acid + L-Cysteine + Argon Sparge Study 1 mg/mL BH4 + 1 mg/mL Ascorbic Acid + 1 mg/mL L-Cysteine in pH 7 Buffer and Argon-Sparged and Argon blanket-Sealed |

Proposed sampling times for studies to be conducted in various buffer solutions were estimated by comparing the half-life of a single study at pH 3.1 with data obtained by Davis, et al. (1988; Eur. J. Biochem. 173, 345-351, (1988)), in pH 6.8 Tris and phosphate buffers. The stability study of a pH 3.1 solution yielded an estimated $t_{1/2}$ of 17769 min (12.3 days) and the work of Davis et al yielded a $t_{1/2}$ of 10 min in phosphate pH 6.8 buffer and 14 min in pH 6.8 Tris buffer. These two studies suggest an order of magnitude reduction in half-life (i.e. an order of magnitude increase in reactivity) of BH4 for every one-fold increase in pH (see Table 19). Based on this approximation, pH 1.2 to pH 3 solutions were sampled weekly initially and sampling time corrections were made if necessary after the first 2 data points were collected. The estimated sampling times at 25° C. are provided in Table 19.

TABLE 19

Suggested Sampling Times at Various pH Based on Measured Half-life of BH4 and Theoretical Half-Lives Derived from Them

| pH | Measured $t_{1/2}$ (Min) | Estimated $t_{1/2}$ Based on $t_{1/2}$ Obtained at pH 3 (Min)[a] | Initially Suggested[c] Sampling Time |
|---|---|---|---|
| 1.0 | — | 776900.0 (1234 days) | Every 7 days |
| 2.0 | — | 177690.0 (123.4 days) | Every 7 days |
| 3.0 | 17769.0 (12.34 days) | 17769.0 (12.34 days) | Every 96 hours |
| 4.0 | — | 1776.9 (1.23 days) | Every 12 hours |
| 5.0 | — | 177.7 (0.12 days) | Every ½ Hour |
| 6.0 | — | 17.7 (0.01 days) | Every 5 minutes[d] |
| 6.8[b] | 10 (Phosphate) 14 (Tris) | | |
| 7.0 | — | 1.8 | Every ½ minutes[d] |

[a]Estimated $t_{1/2}$ is based on changing by an order of magnitude, the half-life obtained at pH 3.0 for every one-fold change in pH. pH < 3 are increased upwards while pH > 3 are decreased downwards by an order of magnitude in a stepwise fashion to roughly match the pH 6.8 data obtained by Davis et al..

[b]Data obtained from Davis, et al. 1988; Eur. J. Biochem., 173, 345-351, (1988)

[c]Sampling can be modified

Figure 36:
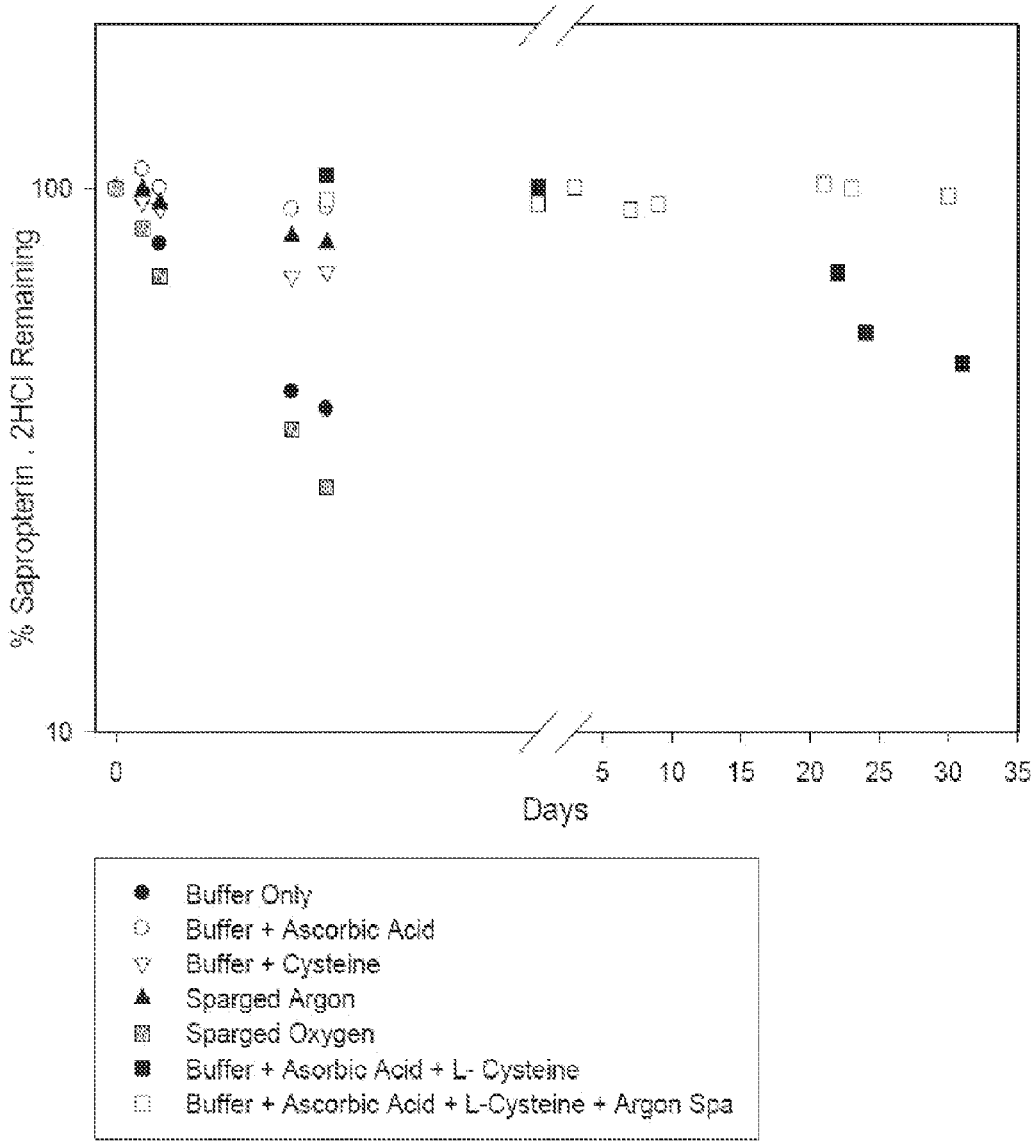
FIG. 36 shows a stability study of intravenous BH4 formulations at pH 4 over 35 days.
Figure 37:
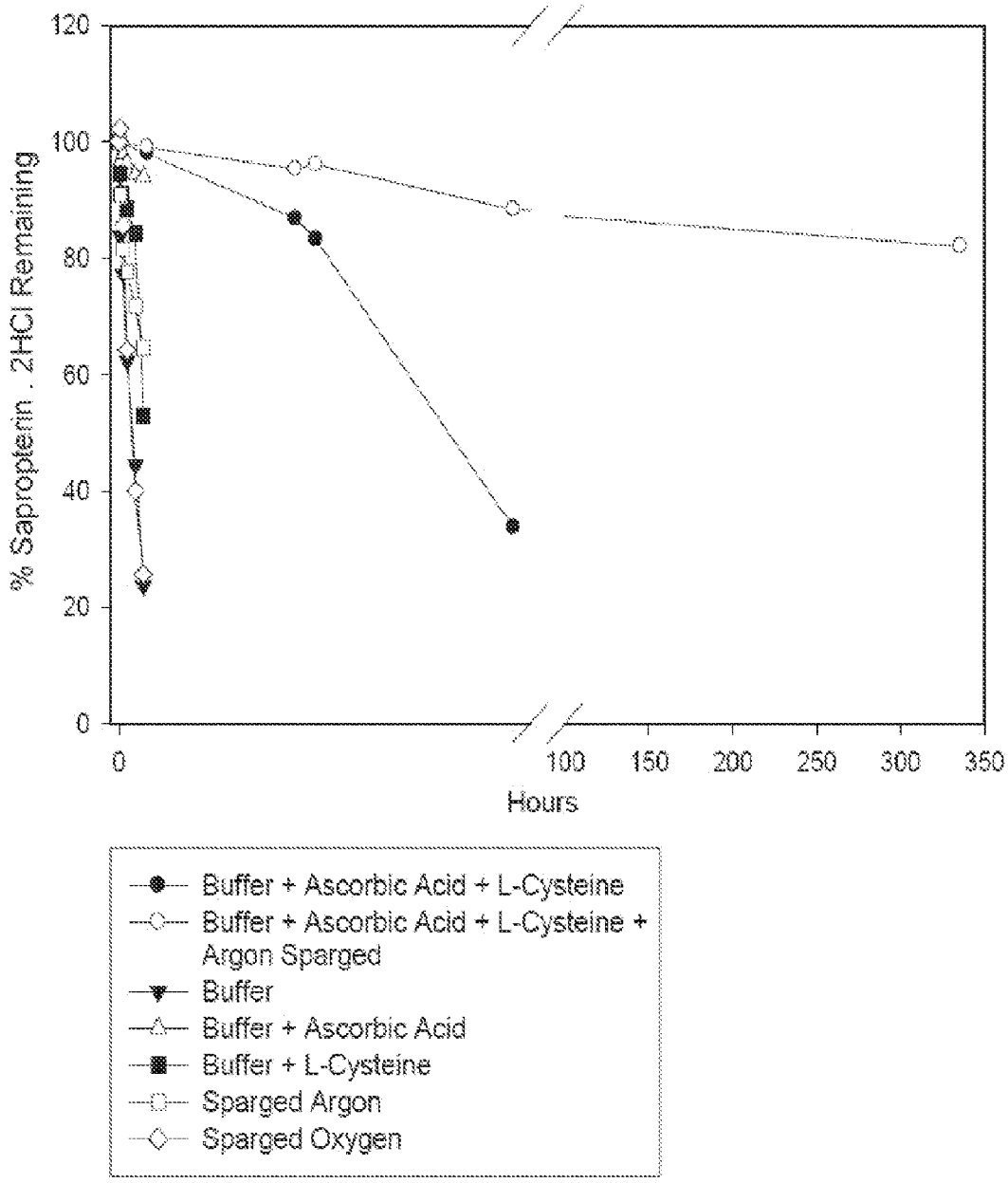
FIG. 37 shows a stability study of various intravenous BH4 formulations over 350 hours.

[d]Reaction solutions are sampled and quenched as fast as possible and require a stopwatch and 2 people, one sampling/quenching and the other accurately recording the time in a notebook in minutes and/or seconds Studies were conducted in pH 1-7 buffer solutions and at 5° C., 25° C., 30° C. and 37° C. Although these studies were conducted in non-hermetically sealed containers, anti-oxidants alone (ascorbic acid or L-cysteine) or combined together (ascorbic acid+L-cysteine) reduced the rate of loss or degradation of BH4 (see FIG. 36 and FIG. 37). Sparging a solution containing both ascorbic acid and L-cysteine substantially enhanced the stability of BH4.

Figure 38:
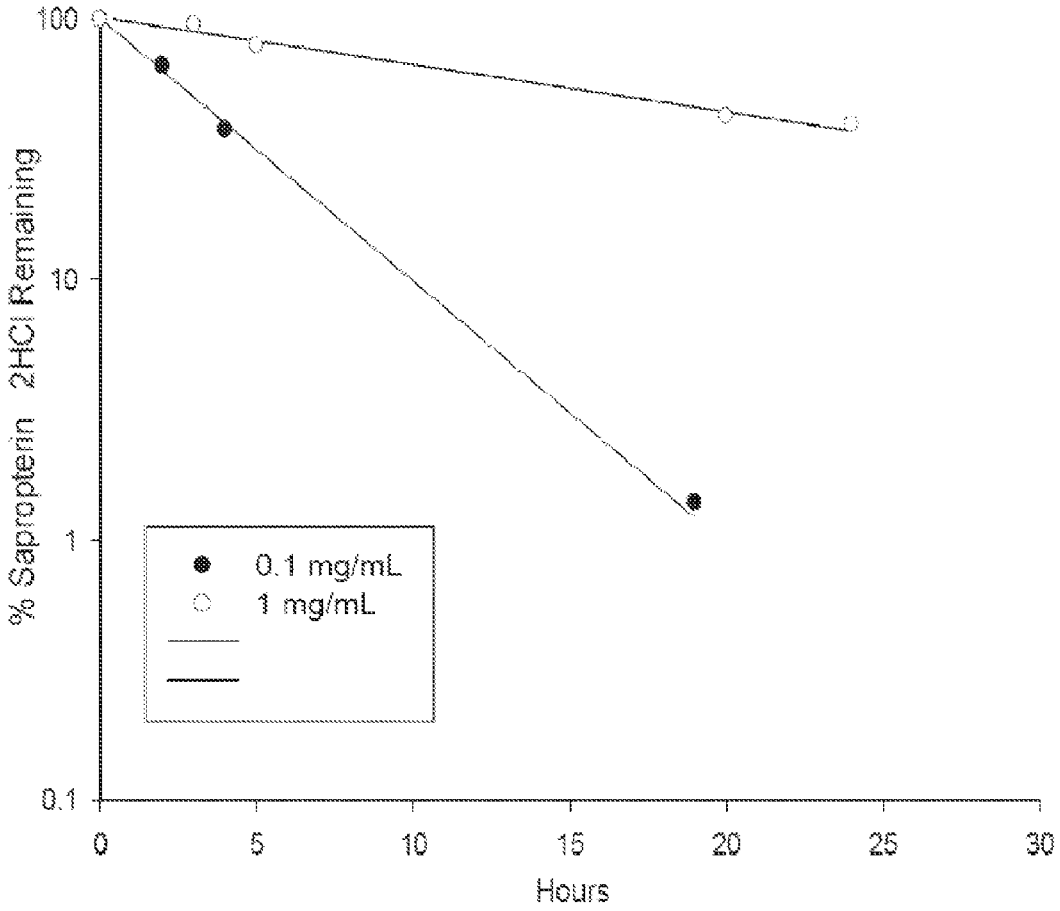
FIG. 38 shows a stability study of intravenous BH4 formulations at various BH4 concentrations.

The rate of degradation of BH4 is concentration-dependent (see FIG. 38). Therefore high dose, highly concentrated formulations of BH4 were shown to require lower concentration of stabilizers for synergistic stabilization of the formulations.

This results demonstrate that formulation of long shelf-life, stable, liquid formulations can be produced according to the methods and compositions described herein, including sterile injectable liquids, oral liquids, and lyophilized and sterile powders for constitution formulations.

Example 7

Liquid and Lyophilized Formulations of Tetrahydrobiopterin for Oral and Parenteral Use

Example Compositions of Formulations

TABLE 20

Specific formulation buffered at pH 4 having ascorbic acid as stabilizer

| Components | Amount (mg) | % Weight/Volume | Function |
|---|---|---|---|
| BH4 | 1.00 | 0.10 | Active substance |
| Ascorbic Acid | 10.00 | 1.00 | Antioxidant |
| Citric Acid | 6.56 | 0.66 | Buffering agent |
| Sodium Citrate, Dihydrate | 5.53 | 0.55 | Buffering agent |
| Water for Injection qs | 1.00 mL | 1.00 mL | Diluent |

TABLE 21

Formulation buffered at pH 4.0 containing a combination of two stabilizers: ascorbic acid and sodium metabisulfite

| Components | Amount (mg) | % Weight/Volume | Function |
|---|---|---|---|
| BH4 | 1.00 | 0.10 | Active substance |
| Ascorbic Acid | 2.50 | 0.25 | Antioxidant |
| Sodium Metabisulfite | 2.50 | 0.25 | Antioxidant |
| Citric Acid | 6.56 | 0.66 | Buffering agent |
| Sodium Citrate, Dihydrate | 5.53 | 0.55 | Buffering agent |
| Water for Injection qs | 1.00 mL | 1.00 mL | Diluent |

TABLE 22

Formulation buffered at pH 4.0 containing a combination of three stabilizers: L-cysteine, ascorbic acid and sodium metabisulfite

| Components | Amount (mg) | % Weight/Volume | Function |
|---|---|---|---|
| BH4 | 1.00 | 0.10 | Active substance |
| Ascorbic Acid | 2.00 | 0.20 | Antioxidant |
| Sodium Metabisulfite | 2.00 | 0.20 | Antioxidant |
| L-Cysteine | 4.00 | 0.40 | Antioxidant |
| Citric Acid | 6.56 | 0.66 | Buffering agent |
| Sodium Citrate, Dihydrate | 5.53 | 0.55 | Buffering agent |
| Water for Injection qs | 1.00 mL | 1.00 mL | Diluent |

TABLE 23

Formulation buffered at pH 7.0 containing only ascorbic acid only as stabilizer

| Components | Amount (mg) | % Weight/Volume | Function |
|---|---|---|---|
| BH4 | 10.00 | 1.00 | Active substance |
| Ascorbic Acid | 50.00 | 5.00 | Antioxidant |
| Sodium Monobasic Phosphate, Monohydrate | 10.24 | 0.10 | Buffering agent |
| Sodium Dibasic Phosphate | 17.76 | 0.18 | Buffering agent |
| Water for Injection qs | 1.00 mL | 1.00 mL | Diluent |

TABLE 24

Formulation buffered at pH 7.0 containing ascorbic acid sodium metabisulfite as stabilizers

| Components | Amount (mg) | % Weight/Volume | Function |
|---|---|---|---|
| BH4 | 10.00 | 1.00 | Active substance |
| Ascorbic Acid | 20.00 | 2.00 | Antioxidant |
| Sodium Metabisulfite | 15.00 | 1.50 | Antioxidant |
| Sodium Monobasic Phosphate, Monohydrate | 10.24 | 0.26 | Buffering agent |
| Sodium Dibasic Phosphate | 17.76 | 0.44 | Buffering agent |
| Water for Injection qs | 1.00 mL | 1.00 mL | Diluent |

TABLE 25

Formulation buffered at pH 7.0 containing ascorbic, sodium metabisulfite and L-Cysteine as stabilizers

| Components | Amount (mg) | % Weight/Volume | Function |
|---|---|---|---|
| BH4 | 10.00 | 1.00 | Active substance |
| Ascorbic Acid | 20.00 | 2.00 | Antioxidant |
| Sodium Metabisulfite | 15.00 | 1.50 | Antioxidant |
| L-Cysteine | 10.00 | 1.00 | Antioxidant |
| Sodium Monobasic Phosphate, Monohydrate | 10.24 | 0.26 | Buffering agent |
| Sodium Dibasic Phosphate | 17.76 | 0.44 | Buffering agent |
| Water for Injection qs | 1.00 mL | 1.00 mL | Diluent |

High Dose Liquid Formulations

TABLE 26

Formulation buffered at pH 6.0 containing ascorbic acid only as stabilizer

| Components | Amount (mg) | % Weight/Volume | Function |
|---|---|---|---|
| BH4 | 50.00 | 0.10 | Active substance |
| Ascorbic Acid | 7.50 | 0.75 | Antioxidant |
| Citric Acid | 5.30 | 0.53 | Buffering agent |
| Sodium Citrate, Dihydrate | 51.4 | 5.14 | Buffering agent |
| Water for Injection qs | 1.00 mL | 1.00 mL | Diluent |

TABLE 27

Formulation buffered at pH 6.0 containing a combination of two stabilizers: ascorbic acid and sodium metabisulfite

| Components | Amount (mg) | % Weight/Volume | Function |
|---|---|---|---|
| BH4 | 50.00 | 5.00 | Active substance |
| Ascorbic Acid | 2.50 | 0.25 | Antioxidant |
| Sodium Metabisulfite | 2.50 | 0.25 | Antioxidant |
| Citric Acid | 5.30 | 0.53 | Buffering agent |
| Sodium Citrate, Dihydrate | 51.4 | 5.14 | Buffering agent |
| Water for Injection qs | 1.00 mL | 1.00 mL | Diluent |

TABLE 28

Formulation buffered at pH 6.0 containing a combination of three stabilizers: L-cysteine, ascorbic acid and sodium metabisulfite

| Components | Amount (mg) | % Weight/Volume | Function |
|---|---|---|---|
| BH4 | 50.00 | 0.10 | Active substance |
| Ascorbic Acid | 2.00 | 0.20 | Antioxidant |
| Sodium Metabisulfite | 2.00 | 0.20 | Antioxidant |
| L-Cysteine | 1.00 | 0.10 | Antioxidant |
| Citric Acid | 5.30 | 0.53 | Buffering agent |
| Sodium Citrate, Dihydrate | 51.4 | 5.14 | Buffering agent |
| Water for Injection qs | 1.00 mL | 1.00 mL | Diluent |

TABLE 29

Oral formulation buffered at pH 3.0 citrate buffer and containing ascorbic acid only as stabilizer

| Components | Amount (mg) | % Weight/Volume | Function |
|---|---|---|---|
| BH4 | 10.00 | 1.00 | Active substance |
| Ascorbic Acid | 20.00 | 2.00 | Antioxidant |
| Sucrose | 200.00 | 20.00 | Sweetener |
| Orange Flavor | 1.00 | 0.10 | Flavoring agent |
| Citric Acid | 8.98 | 0.90 | Buffering agent |
| Sodium Citrate, Dihydrate | 2.13 | 0.21 | Buffering agent |
| Water for Injection qs | 1.00 mL | 1.00 mL | Diluent |

TABLE 30

Oral formulation buffered at pH 3.5 tartrate buffer and containing ascorbic acid and sodium metabisulfite as stabilizers

| Components | Amount (mg) | % Weight/Volume | Function |
|---|---|---|---|
| BH4 | 10.00 | 1.00 | Active substance |
| Ascorbic Acid | 20.00 | 2.00 | Antioxidant |
| Sodium Metabisulfite | 5.00 | 0.50 | Antioxidant |
| Sucrose | 200.00 | 20.00 | Sweetener |
| Grape Flavor | 1.00 | 0.10 | Flavoring agent |
| Tartaric Acid | 1.34 | 0.13 | Buffering agent |
| Sodium Tartrate Dibasic Dihydrate | 8.39 | 0.84 | Buffering agent |
| Water for Injection qs | 1.00 mL | 1.00 mL | Diluent |

TABLE 31

Oral formulation buffered at pH 3.5 in malic acid based buffer and containing ascorbic acid and sodium metabisulfite as stabilizers

| Components | Amount (mg) | % Weight/Volume | Function |
|---|---|---|---|
| BH4 | 10.00 | 1.00 | Active substance |
| Ascorbic Acid | 20.00 | 2.00 | Antioxidant |
| Sodium Metabisulfite | 15.00 | 1.50 | Antioxidant |
| Sucrose | 200.00 | 20.00 | Sweetener |
| Apple Flavor | 1.00 | 0.10 | Flavoring agent |
| Malic Acid | 3.07 | 0.31 | Buffering agent |
| Sodium Malate Dibasic | 4.91 | 0.49 | Buffering agent |
| Water for Injection qs | 1.00 mL | 1.00 mL | Diluent |

The foregoing formulated or compounded solutions are optionally sparged with an inert gas (e.g., argon or nitrogen) or carbon dioxide in the compounding tank and primary containers preferably are sealed in a blanket of inert gas or carbon dioxide to remove oxygen from the container headspace. The formulations can be scaled up to any volume by multiplying the component amounts by an appropriate scale up factor.

Example 8

LC/MS/MS Determination of Tetrahydrobiopterin (BH4) in Human Plasma by Measuring L-Biopterin Concentration upon Oxidation under Basic Conditions Tetrahydrobiopterin (BH4) is a small molecule therapeutic for the treatment of patients with phenylketonuria (PKU). It is important to have an accurate and specific method to measure BH4 concentrations in human plasma. However, it is a challenge to quantify BH4 in human plasma because of its low endogenous concentration and instability. Under basic conditions, BH4 is oxidized into dihydrobiopterin (BH2) and ultimately L-Biopterin. Furthermore, the oxidation conversion ratio of BH4 to L-Biopterin is nearly constant up to 23 weeks. Therefore, by measuring L-Biopterin concentration upon oxidation under basic condition, and applying a molar conversion ratio, we can reliably determine the BH4 concentrations in human plasma.

Published methods are based on the classical method developed by Fukushima and Nixon (Anal. Biochem., 102, 176-188 (1980)) using HPLC with fluorescence detection. In the LC/MS/MS method, the human plasma sample was stabilized with antioxidant, spiked with an internal standard (IS) solution and basified with sodium hydroxide solution, then oxidized with iodine solution. Upon incubation in dark at room temperature, ascorbic acid is added to reduce the excess iodine. Oxidized samples were extracted by protein precipitation. L-Biopterin in the reconstituted extracts was analyzed by using reversed-phase HPLC with Turbo Ion Spray® MS/MS detection. Negative ions for L-Biopterin were monitored in MRM mode. Drug-to-IS peak area ratios for the standards were used to create a linear calibration curve using $1/x^2$ weighted least-squares regression analysis.

The oxidation conversion ratio of BH4 to L-Biopterin was evaluated at multiple time-points: 0, 1, 2, 4, 8, 12 and 23 weeks, and found consistent in all the tested time-points with a nominal molar conversion ratio of 47.3% determined from the first three consecutive time-points. The difference between the conversion ratio at other time-points and the nominal value ranges from −2.3 to 6.3%. The LC/MS/MS method was validated to quantify L-Biopterin in $K_2$ EDTA human plasma in the linear calibration range of 5 to 1000 ng/mL (equivalent to 11 to 2114 ng/mL for BH4). The assay precision and accuracy was evaluated with quality control samples (QCs) and the results showed intraday precision between 4.7 to 14.5% CV; intraday accuracy between −7.1 to 7.4% nominal values; and interday precision and accuracy of 7.4 to 16.4% CV and −8.3 to 3.7% nominal values, respectively. The mean extraction recovery for L-Biopterin was 65.3%. In $K_2$ EDTA human plasma, L-Biopterin was found to be stable at room temperature for at least 4 hours and after 4 freeze thaw cycles, and at −70° C. for at least 275 days.

Example 9

Determination of BH4/BH2/B Using HPLC with Electrochemical and Fluorescence Detection A study was performed to develop a method of determining tetrahydrobiopterin (BH4), dihydrobiopterin (BH2) and biopterin (B) concentrations in human plasma using reverse phase high performance liquid chromatography(HPLC) with fluorescence detection (FD) and electrochemical detection (ECD). The method is based on Cai, et al. (Cardiovascular Research 55: 838-849, 2002).

Stock solutions of BH4 (in 20 mM HCl), BH2 and B (in DMSO) were made to a final concentration of 10 mM and stored at −80° C. Calibration standard working solutions were prepared from stock solution at 100, 10, 7.5, 5, 2.5, and 1 nM in K2 EDTA human plasma modified by 0.1% (w/v) 1,4-Dithioerythritol (DTE). Quality control working solutions of BH4, BH2 and B were prepared at 5, 8, 25 and 50 nM in K2 EDTA human plasma modified by 0.1% (w/v) DTE and stored at −80° C.

For sample processing, plasma was diluted 1:10 in resuspension buffer. To 180 μl of the diluted plasma, 20 μl of the 10× precipitation buffer was added. This process of plasma dilution and precipitation was applied to all plasma standards, plasma samples and plasma QCs. After the addition of the 10× precipitation buffer, the sample was centrifuged at maximum speed at 4° C. for 5 min to remove non-specific plasma debris. 150 mL supernatant was then be transferred to a sample vial and then placed on an autosampler for a 100 mL injection.

The mobile phase (2L) was prepared with 13.6 g sodium acetate (50 mM), 2.1 g citric acid (5 mM) 36 mg EDTA (48 mM), 49.4 mg DTE (160 mM), and 2% methanol by volume in water. The pH was adjusted to 5.22. Resuspension buffer (20 mL) was made with 20 mL of PBS pH 7.4 (50 mM), 20 uL of 1 M DTE (1 mM), and 100 mL of 100 uM EDTA. The 10× precipitation buffer (25 mL) was made fresh with 2.88 mL phosphoric acid (1M), 9.39 g trichloroacetic acid (2 M) and 20 mL 1M DTE (1 mM).

Tetrahydrobiopterin (BH4), dihydrobiopterin (BH2), and Biopterin (B) were separated using reverse phase HPLC separation. BH4 was measured using electrochemical detection in which BH4 is oxidized by electrode 1 to quinonoid dihydrobiopterin (qBH2) and then reduced back to BH4 at electrode 2. The detector then uses the current generated by this reduction reaction to determine the concentration of BH4. BH2 and B can be measured in the same injection using fluorescence detection. Post column oxidation of BH2 using a conditioning guard cell at the optimum potential, oxidizes BH2 to Biopterin.

HPLC separation was carried out on an ACE C-18 (250 mm×4.6 mm) column, 5 μM, at a flow rate of 1.3 mL/min with a run time of 13 minutes. Electrochemical detection settings were E1: +100 mV (background current +500 nA to +600 nA) and E2: −300 mV (background current −50 nA to −60 nA). Post-column oxidation was set at 900 mV. Fluorescence detection settings were excitation wavelength: 350 nM and emission wavelength: 450 nM.

Linearity and range of the method were assessed based on the precision and accuracy of the standards in plasma and buffer. The standard curve concentration was established using at least 4-6 non-zero concentrations for each analyte. The concentration of the standards was 1, 2.5, 5, 7.5, 10, and 100 nM. The results showed a linear fit from 1 to 100 nM for BH4, BH2, and B with R2 of >0.99.

Accuracy was determined by replicate analysis of quality control samples containing known amounts (2, 8, 25, and 50 nM) of the analyte and expressed as a percent accuracy. Precision is also calculated based on the data from the quality controls. Intra-assay precision and inter-assay precision were evaluated based on the CV %. On three separate experimental runs concentrations of each analyte were prepared in plasma and analyzed. In addition 10 nM of BH4, BH2, and B was "spiked" into human plasma samples to determine the accuracy and recovery. The measurements of BH4, BH2, and B at 8, 25, and 50 nM proved accurate within 112%-89% and demonstrated precision (CV %) of 2.5%-20%. Spike recovery experiments using 10 nM BH4, BH2, and B in clinical samples of human plasma demonstrated recoveries between 70%-130%. The results demonstrate that the method is accurate and precise for samples with concentrations greater than 2 nM.

To check for the presence of endogenous interference in six different lots of plasma, 10 nM BH4, BH2, and B were spiked into six different lots of plasma and the determine accuracy and precision were determined for each plasma sample. Selectivity experiments show that the six individuals had endogenous baseline BH4 levels of between below quantifiable limit to 2.48 nM. Similarly, BH2 and B concentrations ranged from 0.02 to 10 nM. The recovery of the 10 nM spiked analytes ranged from 69%-87%. The variability (CV %) across the individual plasma samples and analytes when spiked at 10 nM ranged from 23%-37%. The variability of the endogenous levels of BH4, BH2 and B ranged from 0-9.96 nM. Together, the results indicate a trend suggesting matrix interference or loss during extraction, but do not indicate strong selectivity between individuals.

To measure matrix effect standard curves prepared in plasma or buffer were compared for accuracy (recovery), linearity and correlation. Comparison of the standards prepared in plasma versus standards prepared in buffer demonstrates a modest matrix effect and generally good correlation. All three analytes had excellent linear fits for plasma and buffer. BH4 and B did not demonstrate significant matrix effects across the concentration range. However, BH2 had less recovery at the highest standard concentration (100 nM). The quality control samples prepared in buffer and plasma demonstrated good accuracy. Overall, matrix effects seem minimal, with a trend toward less recovery in buffer as compared to plasma. Because BH4 and BH2 are readily oxidized, collected plasma and sample buffers should contain antioxidants and have low pH when possible.

To test the ability to accurately dilute a plasma and buffer sample spiked with 250 nM of BH4, BH2 and B, plasma was diluted using blank plasma in a 3-fold dilution series. The diluted samples were analyzed and compared to the nominal value after the dilution factor was applied. The dilution of high concentrations of BH4, BH2, and B can be accurately made. For BH4 the observed concentrations following dilution were between 83%-104% accurate for concentrations between 83.33 nM and 3.07 nM. BH2 was 74%-80% accurate across the quantitative range (83 nM-3 nM). B was 119%-113% accurate across the quantitative range (83 nM-3 nM). Therefore, a sample that is above the quantitative limit can be diluted accurately.

Four concentrations of analytes (2, 8, 25 and 50 nM) were prepared in plasma and frozen for a minimum of 24 hours for one cycle and a minimum of 12 hours for other cycles for a minimum of three cycles. Samples were thawed unassisted at room temperature in between frozen periods. The accuracy and variability after each and all free-thaw cycles was assessed to establish the maximal number of cycles a sample could undergo. The BH4-, BH2-, and B-containing samples can undergo up to 3 freeze-thaw cycles without significant change in accuracy or precision of the measurement. Plasma samples with 8 nM-50 nM BH4 are 121%-91% accurate and CV % less than 10%. Similarly BH2 measurements were 77%-88% accurate across the quantitative range of the assay. B measurements were 98%-99% accurate across the quantitative range with precision (CV %) of 5%-8%. The 2 nM sample of BH4, BH2, and B did not prove accurate or precise following repeated freeze-thaw. Therefore, standards, quality controls and study samples may be frozen and thawed up to 3 times.

Because the analytes are sensitive to oxidation we examined long-term frozen stability to mimic expected storage conditions. Four concentration levels (2, 8, 50, and 100 nM) of BH4, BH2, and B were prepared in plasma and stored at −70° C. for 8 weeks. Stability samples were assayed fresh and at weeks 3, 5, 6, and 8. BH4 and B had good long term frozen stability. BH2 demonstrated reduced sample concentration after prolonged storage. Over the 8 weeks of storage, plasma samples with BH4 were 93%-94% accurate and had CV % between 31%-0.21%, with the most variation seen at the 2 nM concentration. BH2 measurements were 63%-85% accurate across the concentrations tested with reduced accuracy at the 2 nM and 100 nM concentrations. The precision (CV %) ranged from 37% to 18% for these samples. B measurements were 88%-101% accurate across the concentrations tested with precision (CV %) of 23%-0.14%, with the highest variability at the 2 nM concentration. Together, this data supports the recommendation to store samples for up to 8 weeks without appreciable loss of analyte concentration. BH2 seems to be the most susceptible to degradation (oxidation).

To measure the stability of BH4, BH2, and B in the autosampler, 8 nM of each analyte in reconstitution solvent stayed on the autosampler for 0.25, 4, and 11 hours. The accuracy and precision of the measurements were compared. The observed BH4 measurement was accurate within 5% of theoretical at each time point with accuracy and precision across all three measurements of 102% and 0.054% respectively. The measurement of BH2 had decreasing accuracy and increasing variability after 4 hours. After 11 hours on the autosampler about 50% of the BH2 was measured. This indicates poor autosampler stability in run buffer. The measurement of B remained accurate within 125% of theoretical after 11 hours. Therefore, run times of no more than 4 hours are recommended.

To determine injection carry-over, an extracted baseline plasma sample was inserted after the highest standard concentration 100 nM. This was done to mimic the possibility of overestimating the concentration of analyte in a low concentration sample due to carry-over. The injection carryover of BH4, BH2, and B is minimal and does not account for more than 1% of the peak area of the 100 nM upper limit of quantitation. The injection carryover accounts for approximately 5%-20% of the lower limit of quantitation, based on the average peak area obtained from the low quality control (2 nM). Therefore, preferably the samples should be ordered from lowest to high (i.e., pre-dose first, followed by post-dose samples) and additional washes to clean the column periodically during a run preferably will be made to minimize potential carryover.

A qualified method which was robust, specific, accurate and precise was developed. This method is appropriate to quantify the levels of BH4, BH2 and B in plasma for pharmacokinetic and drug studies.

All patents, publications and references cited herein are hereby fully incorporated by reference. In case of conflict between the present disclosure and incorporated patents, publications and references, the present disclosure will control.

What is claimed is:

1. A method of orally administering tetrahydrobiopterin (BH4), comprising separately administering to a human in need thereof (i) a therapeutically effective amount of BH4 or a pharmaceutically acceptable salt thereof and (ii) food, wherein the BH4 or pharmaceutically acceptable salt thereof is administered at the same time as or within 30 minutes after the food.

2. The method of claim 1, further comprising informing the human that Cmax and AUC are increased by approximately 30% when the BH4 or pharmaceutically acceptable salt thereof is administered with a high-fat, high-calorie meal compared to when the BH4 or pharmaceutically acceptable salt thereof is administered under fasting conditions.

3. The method of claim 1, wherein said BH4 is a crystalline polymorph, as a hydrochloride salt, that exhibits an X-ray powder diffraction pattern with the following characteristic peaks expressed in d-values(A): 8.7 (vs), 5.63 (m), 4.76 (m), 4.40 (m), 4.00 (s), 3.23 (s), 3.11 (vs), preferably 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), and 2.44 (w).

4. The method of claim 1, wherein the BH4 or pharmaceutically acceptable salt thereof is administered at a daily dose of at least 5 mg/kg.

5. The method of claim 1, wherein the BH4 or pharmaceutically acceptable salt thereof is administered at a daily dose of at least 20 mg/kg.

6. The method of claim 1, wherein the human has been diagnosed with hyperphenylalaninemia, a neuropsychiatric disorder, a cardiovascular disease, anemia, or a combination thereof.

7. The method of claim 1, further comprising informing said human that absorption of said BH4 or pharmaceutically acceptable salt thereof is increased when it is ingested with food, compared to when ingested without food.

8. The method of claim 1, wherein said human suffers from one or more disorders selected from the group consisting of phenylketonuria, hyperphenylalaninemia, BH4 deficiency, dopa-responsive dystonia (DRD), sepiapterin reductase (SR) deficiency, or dihydropteridine reductase (DHPR) deficiency, Parkinson's disease, dystonia, pain, fatigue, depression, an affective disorder, schizophrenia, stroke, migraine headaches, Alzheimer's disease, schizophreniform disorder, schizoaffective disorder, brief psychotic disorder, delusional disorder, shared psychotic disorder, psychotic disorder due to a general medical condition, substance-induced psychotic disorder, other psychotic disorders, tardive dyskinesia, chronic fatigue syndrome, acute or chronic depression, chronic stress syndrome, fibromyalgia, attention deficit hyperactivity disorder, bipolar disease, and autism.

9. The method of claim 1, wherein the food comprises a high fat, high calorie meal.

10. The method of claim 1 or claim 8, further comprising dissolving the BH4 or pharmaceutically acceptable salt thereof in a liquid prior to administering to the human.

11. The method of claim 1 or claim 8, wherein the BH4 or pharmaceutically acceptable salt thereof is administered as an intact tablet.

12. The method of claim 1 or claim 8, wherein the BH4 or pharmaceutically acceptable salt thereof is administered as a solid dosage form.

13. The method of claim 1, wherein the BH4 or pharmaceutically acceptable salt thereof is administered once per day.

14. The method of claim 13, wherein the human suffers from hyperphenylalaninemia.

15. The method of claim 13, wherein the human suffers from one or more disorders selected from the group consisting of BH4 deficiency, dopa-responsive dystonia (DRD), sepiapterin reductase (SR) deficiency, and dihydropteridine reductase (DHPR) deficiency.

16. The method of claim 13, wherein the human suffers from one or more disorders selected from the group consisting of Parkinson's disease, dystonia, pain, fatigue, depression, an affective disorder, schizophrenia, stroke, migraine headaches, Alzheimer's disease, schizophreniform disorder, schizoaffective disorder, brief psychotic disorder, delusional disorder, shared psychotic disorder, psychotic disorder due to a general medical condition, substance-induced psychotic disorder, other psychotic disorders, tardive dyskinesia, chronic fatigue syndrome, acute or chronic depression, chronic stress syndrome, fibromyalgia, and bipolar disease.

17. The method of claim 13, wherein the human suffers from attention deficit hyperactivity disorder or autism.

18. The method of claim 13, wherein the BH4 or pharmaceutically acceptable salt thereof is administered as a solid dosage form.

19. The method of claim 13, wherein the BH4 or pharmaceutically acceptable salt thereof is administered as an intact tablet.

20. The method of claim 13, further comprising dissolving the BH4 or pharmaceutically acceptable salt thereof in a liquid prior to administering to the human.

21. A method of orally administering tetrahydrobiopterin (BH4) to a human suffering from hyperphenylalaninemia, comprising separately administering to said human (i) a therapeutically effective amount of BH4 or pharmaceutically acceptable salt thereof, once per day, and (ii) food, wherein the BH4 or pharmaceutically acceptable salt thereof is administered at the same time as or within 30 minutes after the food.

22. The method of claim 21, wherein the human suffers from phenylketonuria.

23. The method of claim 21, wherein the therapeutically effective amount of BH4 or pharmaceutically acceptable salt thereof is at least 5 mg/kg.

24. The method of claim 21, wherein the therapeutically effective amount of BH4 or pharmaceutically acceptable salt thereof is 1 mg/kg to 30 mg/kg.

25. The method of claim 21, wherein the BH4 or pharmaceutically acceptable salt thereof is administered as a solid dosage form.

26. The method of claim 21, wherein the BH4 or pharmaceutically acceptable salt thereof is administered as an intact tablet.

27. The method of claim 21, further comprising dissolving the BH4 or pharmaceutically acceptable salt thereof in a liquid prior to administering to the human.

28. The method of claim 21, wherein the food comprises a high fat, high calorie meal.

* * * * *